(12) United States Patent
Ghobrial et al.

(10) Patent No.: US 8,394,816 B2
(45) Date of Patent: Mar. 12, 2013

(54) METHODS OF USING [3.2.0] HETEROCYCLIC COMPOUNDS AND ANALOGS THEREOF IN TREATING WALDENSTROM'S MACROGLOBULINEMIA

(76) Inventors: Irene Ghobrial, Chestnut Hill, MA (US); Aldo Roccaro, Boston, MA (US); Dharminder Chauhan, Natick, MA (US); Kenneth Anderson, Wellesley, MA (US); Michael Palladino, Olivenhain, CA (US)

(*) Notice: Subject to any disclaimer, the term of this patent is extended or adjusted under 35 U.S.C. 154(b) by 708 days.

(21) Appl. No.: 12/329,504

(22) Filed: Dec. 5, 2008

(65) Prior Publication Data

US 2009/0156469 A1    Jun. 18, 2009

Related U.S. Application Data

(60) Provisional application No. 61/012,396, filed on Dec. 7, 2007.

(51) Int. Cl.
*A61K 31/44* (2006.01)
*A61K 31/42* (2006.01)
*A61K 31/40* (2006.01)

(52) U.S. Cl. .................. 514/290; 514/375; 514/421

(58) Field of Classification Search .................. None
See application file for complete search history.

(56) References Cited

U.S. PATENT DOCUMENTS

| | | | |
|---|---|---|---|
| 5,445,829 A | 8/1995 | Paradissis et al. |
| 5,576,012 A | 11/1996 | Bauer et al. |
| 5,601,845 A | 2/1997 | Buxton et al. |
| 5,641,515 A | 6/1997 | Ramtoola |
| 5,653,987 A | 8/1997 | Modi et al. |
| 5,654,286 A | 8/1997 | Hostetler |
| 5,667,809 A | 9/1997 | Trevino et al. |
| 5,683,676 A | 11/1997 | Akehurst et al. |
| 5,688,529 A | 11/1997 | Lidgate et al. |
| 5,707,615 A | 1/1998 | Cardin et al. |
| 5,707,641 A | 1/1998 | Gertner et al. |
| 5,726,181 A | 3/1998 | Hausheer et al. |
| 5,733,888 A | 3/1998 | Carver et al. |
| 5,756,764 A | 5/1998 | Fenteany et al. |
| 5,874,443 A | 2/1999 | Kiely et al. |
| 5,886,210 A | 3/1999 | Rayle et al. |
| 5,922,683 A | 7/1999 | Or et al. |
| 6,133,308 A | 10/2000 | Soucy et al. |
| 6,147,223 A | 11/2000 | Fenteany et al. |
| 6,214,862 B1 | 4/2001 | Fenteany et al. |
| 6,271,199 B2 | 8/2001 | Brand et al. |
| 6,294,560 B1 | 9/2001 | Soucy et al. |
| 6,333,358 B1 | 12/2001 | Nakazato et al. |
| 6,335,358 B1 | 1/2002 | Fenteany et al. |
| 6,350,759 B1 | 2/2002 | Casara et al. |
| 6,458,825 B1 | 10/2002 | Fenteany et al. |
| 6,500,825 B2 | 12/2002 | Lan et al. |
| 6,506,787 B2 | 1/2003 | Fujishita et al. |
| 6,509,331 B1 | 1/2003 | Audia et al. |
| 6,566,553 B2 | 5/2003 | Soucy et al. |
| 6,645,999 B1 | 11/2003 | Schreiber et al. |
| 6,794,516 B2 | 9/2004 | Soucy et al. |
| 6,838,477 B2 | 1/2005 | Schreiber et al. |
| 6,849,743 B2 | 2/2005 | Soucy et al. |
| 7,144,723 B2 | 12/2006 | Fenical et al. |
| 7,176,232 B2 | 2/2007 | Fenical et al. |
| 7,176,233 B2 | 2/2007 | Fenical et al. |
| 7,179,834 B2 | 2/2007 | Fenical et al. |
| 7,183,417 B2 | 2/2007 | Corey |
| 7,276,530 B2 | 10/2007 | Potts et al. |
| 7,371,875 B2 | 5/2008 | Xiao et al. |
| 7,442,830 B1 | 10/2008 | Olhava et al. |
| 7,511,156 B2 | 3/2009 | Corey |
| 7,544,814 B2 | 6/2009 | Potts et al. |
| 7,572,606 B1 | 8/2009 | Lam et al. |
| 7,579,371 B2 | 8/2009 | Palladino et al. |
| 7,635,712 B2 | 12/2009 | Fenical et al. |
| 7,879,576 B2 | 2/2011 | Fenical et al. |
| 7,910,616 B2 | 3/2011 | Macherla et al. |
| 7,928,138 B2 | 4/2011 | Feling et al. |
| 2001/0002391 A1 | 5/2001 | Brand et al. |
| 2001/0051654 A1 | 12/2001 | Elliott et al. |
| 2002/0049157 A1 | 4/2002 | Wu et al. |
| 2002/0106689 A1 | 8/2002 | Faustman et al. |
| 2003/0157695 A1 | 8/2003 | Fenical et al. |
| 2004/0106539 A1 | 6/2004 | Schubert et al. |
| 2004/0138196 A1 | 7/2004 | Fenical et al. |
| 2005/0049294 A1 | 3/2005 | Palladino et al. |
| 2005/0203029 A1 | 9/2005 | Schubert et al. |
| 2005/0203162 A1 | 9/2005 | Xiao et al. |
| 2005/0239866 A1 | 10/2005 | Fenical et al. |
| 2005/0245435 A1* | 11/2005 | Smyth et al. ............ 514/7 |
| 2005/0288352 A1 | 12/2005 | Potts et al. |
| 2006/0008852 A1 | 1/2006 | Fenical et al. |
| 2006/0229353 A1 | 10/2006 | Stadler et al. |
| 2006/0264495 A1 | 11/2006 | Palladino et al. |

(Continued)

FOREIGN PATENT DOCUMENTS

| CA | 2429163 | 6/2002 |
|---|---|---|
| WO | WO 96/32105 | 10/1996 |

(Continued)

OTHER PUBLICATIONS

Jia et al., Blood (ASH Annual Meeting Abstracts) Nov. 2006;108: Abstract 4746.*
Adams, et al., "Proteasome Inhibitors: A Novel Class of Potent and Effective Antitumor Agents," Cancer Res., (1999) 59:2615-2622.
Adams, J., "Preclinical Development of Velcade (Bortezomib; formerly PS-341) for Multiple Myeloma"—MMRF Abstract, Euro. J. Haematology, (2003) 70:263 & 265.
Adams, J., "Proteasome Inhibitors as New Anticancer Drugs," Curr. Opin. Oncol., (2002) 14:628-72.
Alessandri, et al., "Mobilization of Capillary Endothelium In Vitro Induced by Effectors of Angiogenesis In Vivo," Cancer Res., (1983) 43(4):1790-1797.
Alm, et al., "Effects of Topically Applied PGF2 and its Isopropylester on Normal and Glaucomatous Human Eyes," Prog. Clin. Biol. Res., (1989) 312:447-58.

(Continued)

*Primary Examiner* — San-Ming Hui

(57) ABSTRACT

Disclosed are methods of treating Waldenstrom's Macroglobulinemia comprising administering to the animal, a therapeutically effective amount of a heterocyclic compound of Formula I.

38 Claims, 15 Drawing Sheets

U.S. PATENT DOCUMENTS

| | | |
|---|---|---|
| 2006/0287520 A1 | 12/2006 | Danishefsky et al. |
| 2007/0004676 A1 | 1/2007 | Palladino et al. |
| 2007/0155815 A1 | 7/2007 | Fenical et al. |
| 2007/0161693 A1 | 7/2007 | Corey |
| 2007/0225350 A1 | 9/2007 | Anderson et al. |
| 2007/0249693 A1 | 10/2007 | Ling et al. |
| 2008/0070273 A1 | 3/2008 | Fenical et al. |
| 2008/0070969 A1 | 3/2008 | Potts et al. |
| 2008/0280968 A1 | 11/2008 | Palladino |
| 2009/0022730 A1 | 1/2009 | Raulf et al. |
| 2009/0036390 A1 | 2/2009 | Anderson et al. |
| 2009/0062547 A1 | 3/2009 | Romo et al. |
| 2009/0069401 A1 | 3/2009 | Fenical et al. |
| 2009/0148445 A1 | 6/2009 | Bonavida et al. |
| 2009/0156469 A1 | 6/2009 | Ghobrial et al. |
| 2009/0197937 A1 | 8/2009 | Fenical et al. |
| 2009/0234137 A1 | 9/2009 | Ling et al. |
| 2009/0298906 A1 | 12/2009 | Macherla et al. |
| 2009/0318529 A1 | 12/2009 | Fenical et al. |
| 2010/0144826 A1 | 6/2010 | Fenical et al. |
| 2010/0168046 A1 | 7/2010 | Palladino et al. |

FOREIGN PATENT DOCUMENTS

| | | |
|---|---|---|
| WO | WO 98/35691 | 8/1998 |
| WO | WO 99/09006 | 2/1999 |
| WO | WO 99/15183 | 4/1999 |
| WO | WO 00/23614 | 4/2000 |
| WO | WO 02/47610 | 6/2002 |
| WO | WO 2004/043374 | 5/2004 |
| WO | WO 2004/071382 | 8/2004 |
| WO | WO 2005/002572 | 1/2005 |
| WO | WO 2005/003137 | 1/2005 |
| WO | WO 2005/094423 | 10/2005 |
| WO | WO 2005/099687 | 10/2005 |
| WO | WO 2006/005551 | 1/2006 |
| WO | WO 2006/028525 | 3/2006 |
| WO | WO 2006/060609 | 6/2006 |
| WO | WO 2006/060676 | 6/2006 |
| WO | WO 2006/060809 | 6/2006 |
| WO | WO 2006/118973 | 11/2006 |
| WO | WO 2007/021897 | 2/2007 |
| WO | WO 2007/033039 | 3/2007 |
| WO | WO 2007/130404 | 11/2007 |
| WO | WO 2007/138116 | 12/2007 |
| WO | WO 2008/124699 | 10/2008 |
| WO | WO 2008/137780 | 11/2008 |
| WO | WO 2009/134531 | 11/2009 |
| WO | WO 2009/140287 | 11/2009 |

OTHER PUBLICATIONS

Beers et al. (Eds.), "Bacterial Diseases," The Merck Manual of Diagnosis and Therapy, (1999) The Merck Research Laboratories, Whitehouse Station N.J., Section 13, Chapter 157: pp. 1157-1158.

Beers et al. (Eds.), "Parasitic Infections," The Merck Manual of Diagnosis and Therapy, (1999) The Merck Research Laboratories, Whitehouse Station N.J., Section 13, Chapter 161: pp. 1241-1252.

Beers et al. (Eds.), The Merck Manual of Diagnosis and Therapy, 17th Ed. 1999, The Merck Research Laboratories, Whitehouse Station N.J., pp. 1193-1201 & 1204.

Beers et al. (Eds.), The Merck Manual of Diagnosis and Therapy, 17th Ed. 1999, The Merck Research Laboratories, Whitehouse Station N.J., pp. 397-399, 948-949, 1916, 1917, 1974, 1975, and 1978-1983.

Beers, et al. (Eds), "The Merck Manual of Diagnosis and Therapy", 17th Ed. 1999, Merck Research Laboratories, pp. 1085-1088, 1101-1135, and 1237-1278.

Bernan, et al., "Marine Microorganisms as a Source of New Natural Products," Advances in Applied Microbiology, (1997) 43:57-90.

Bhalla, et al., "High-Dose Mitoxantrone Induces Programmed Cell Death or Apoptosis in Human Myeloid Leukemia Cells," Blood, (1993) 82(10):3133-3140.

Bicknell, et al. (Eds.), Tumour Angiogenesis, Oxford University Press, New York (1997), Table of Contents, pp. 5.

Blum, et al., "Adriamycin: A New Anticancer Drug with Significant Clinical Activity," Ann Intern Med, (1974) 80(2):249-259.

Blunt, et al., "Marine Natural Products," Nat. Prod. Rep., (2003) 20:1-48.

Bodart, et al., "Anthrax, MEK and Cancer," Cell Cycle, (2002) 1:10-15.

Bradley, et al., "Identification of the Cellular Receptor for Anthrax Toxin," Nature, (2001) 414:225-229.

Brosius, et al., "Complete nucleotide sequence of a 16S ribosomal RNA gene from *Escherichia coli*," Biochemistry, (Oct. 1978) 75(10):4801-8405.

Bull, et al., "Search and Discovery Strategies for Biotechnology: the Paradigm Shift," Microbiol. Mol. Biol. Rev., (2000) 64(3):573-606.

Carey, Francis, Organic Chemistry, 2nd ed., McGraw Hill, Inc., New York (1992), pp. 328-331.

Chauhan, et al., "A Novel Orally Available Proteasome Inhibitor NPI-0052 Induces Killing in Multiple Myeloma (MM) Cells Resistant to Conventional and Bortezomib Therapies," *Blood*, (2004) 104(11):2405.

Chauhan, et al., "A Novel Orally Active Proteasome Inhibitor Induces Apoptosis in Multiple Myeloma Cells with Mechanisms Distinct from Bortezomib," Cancer Cell, (2005) 8:407-419.

Chauhan, et al., "A Novel Proteasome Inhibitor NPI-0052 as an Anticancer Therapy," British Journal of Cancer, (2006) 95(8):961-965.

Cheng, et al., "Arenaric Acid, a New Pentacyclic Polyether Produced by a Marine Bacterium (Actinomycetales)", J. Nat. Prod., (1999) 62:605-607.

Cheng, et al., "Luisols A and B, New Aromatic Tetraols Produced by an Estuarine Marine Bacterium of the Genus *Streptomyces* (Actinomycetales)," J. Nat. Prod., (1999) 62:608-610.

Ciechanover, et al., (Eds.) "The Ubiquitin-Proteasome Proteolytic System—From Classical Biochemistry to Human Diseases" by Baumeister et al., (2002) pp. 68-70.

Claverol, et al., "Mapping and Structural Dissection of Human 20 S Proteasome Using Proteomic Approaches," Mol Cell Proteomics, (2002) 1:567-78.

Cole et al., "The Ribosomal Database Project (RDP-II): sequences and tools for high-throughput rRNA analysis", *Nucl Acids Res.*, (2005) 33(Database Issue):D294-D296 [Online Dec. 17, 2004].

Colquhoun, et al, "Rapid Characterization of Deep-Sea Actionmycetes for Biotechnology Screening Programmes", Antonie Van Leeuwenoek, (2000) 77:359-367.

Colquhoun, et al., "Novel *Rhodococci* and Other Mycolate Actinomycetes From the Deep Sea," Antonie van Leeuwenhoek, (1998) 74:27-40.

Colquhoun, et al., "Taxonomy and Biotransformation Activites of Some Deep-Sea Actinomycetes," Extremophiles, (1998) 2:269-277.

Corey et al. "The Structural Requirements for Inhibition of Proteasome Function by the Lactacystin-derived beta-lactone and Synthetic Analogs," Tetrahedron (1999) 55(11):3305-3316.

Corey, et al., "An Efficient Total Synthesis of a New and Highly Active Analog of Lactacystin," Tetrahedron Letters, (1998) 39:7475-7478.

Corey, et al., "Total Synthesis of Lactacystin," J. Am. Chem. Soc., (1992) 114(26):10677-10678.

Cragg, et al. "Chemical Diversity: A Function of Biodiversity," Trends Pharmacol. Sci., (2002) 23:404-5.

Crane, et al., "A Novel Enantioselective Synthetic Route to Omuralide Analogues with the Potential for Species Selectivity in Proteasome Inhibition," Organic Letters, (2001) 1395-1397.

Crueger, et al. (Eds.), Biotechnology: A Textbook of Industrial Microbiology, 2nd ed. (English Edition, Thomas D. Brock Ed.), Sinauer Associates Inc, Sunderland MA, (1990) Chapter 2:4-8.

Cusack et al., "Rationale for the Treatment of Solid Tumors with the Proteasome Inhibitor Bortezomib", Cancer Treat Rev., (2003) 29(Suppl 1): 21-31.

Cusack, et al., "NPI-0052 Enhances Tumoricidal Response to Conventional Cancer Therapy in a Colon Cancer Model," Clin. Cancer Res., (2006) 22:6758-6764.

Cusack, et al., "Enhanced Chemosensitivity to CPT-11 with Proteasome Inhibitor PS-341: Implications for Systemic Nuclear Factor-kB Inhibition", Cancer Res., (May 1, 2001) 61(9):3535-40.

Davidson, Bradley S., "New Dimensions in Natural Products Research: Cultured Marine Microorganisms," Current Opinion in Biotechnology, (1995) 6:284-291.

Decker, et al., "Inhibition of Caspase-3-mediated Poly(ADP-ribose) Polymerase (PARP) Apoptotic Cleavage by Human PARP Autoantibodies and Effect on Cells Undergoing Apoptosis," J. Biol. Chem., (2000) 275(12):9043-9046.

Delong, et al. "Environmental Diversity of Bacteria and Archaea," Syst. Biol., (2001) 50(4):470-478.

Developmental Therapeutics Program—NCI/NIH, "Cell Lines in the in Vitro Screen", online: http://dtp.nci.nih.gov/docs/misc/common_files/cell_list/html, accessed Oct. 27, 2009.

Developmental Therapeutics Program—NCI/NIH, "DTP Human Tumor Cell Line Screen." Screening Services. DPI. Sep. 28, 2005 http://dtp.nci.nih.gov/branches/btb/ivclsp.html.

Dick, et al., "Mechanistic Studies on the Inactivation of the Proteasome by Lactacystin," J. Biol. Chem., (1996) 271(13):7273-7276.

Ding, et al., "Proteasome Inhibition Induces Reversible Impairments in Protein Synthesis," The FASEB Journal., (2006) 20:1055-1063.

Duesbery, et al., "Proteolytic Inactivation of MAP-Kinase-Kinase by Anthrax Lethal Factor," Science, (1998) 280:734-737.

Elliott, et al., "Proteasome Inhibition: A New Anti-Inflammatory Strategy," J. Mol. Med., (2003) 81:235-245.

Elliott, et al., "The Proteasome: A New Target for Novel Drug Therapies," American Journal of Clinical Pathology, (Nov. 2001) 637-646.

Endo, et al., "Total Synthesis of Salinosporamide A," J. Am. Chem. Soc., (2005) 127(23): 8298-8299 and Supporting Information S1-S23.

Erba, et al., "Mode of Action of Thiocoraline: A Natural Marine Compound With Anti-Tumor Activity," British Journal of Cancer, (1999) 88(7):971-980.

Escuyer, et al., "Anthrax Protective Antigen Interacts with a Specific Receptor on the Surface of CHO-K1 Cells," Infect. Immun., (1991) 59(10):3381-3386.

Faulkner, D. John, "Marine Natural Products," Nat. Prod. Rep., (2001) 18(1):1-49.

Feling, et al. "Salinosporamide A: A Highly Cytotoxic Proteasome Inhibitor from a Novel Microbial Source, a Marine Bacterium of the New Genus *Salinospora*," Angew. Chem. Int. Ed., (2003) 42(3):355-357.

Fenical, et al., "Marine Microorganisms as a Biomedical Source: Are They Unculturable or Uncultured?" PowerPoint Presentation, Center for Marine Biotechnology and Biomedicine (Feb. 24, 2002).

Fenical, et al., "Marine Microorganisms as a Developing Resource for Drug Discovery," Pharmaceutical News, (2002) 9:489-494.

Fenical, et al., "*Salinospora*, a Major New Marine Actinomycete Taxon for Drug Discovery," Powerpoint Presentation, Center for Marine Biotechnology and Biomedicine (Jun. 24, 2001).

Fenical, William, "Chemical Studies of Marine Bacteria: Developing a New Resource," Chem. Rev., (1993) 93(5):1673-1683.

Fenical, William, "New Pharmaceuticals From Marine Organisms," Marine Biotechnology, (1997) 15:339-341.

Fenical, et al., "Discovery and Development of the Anticancer Agent Salinosporamide A (NPI-0052)," *Bioorganic & Med. Chem.*, (2009) 17:2175-2180.

Fenteany, et al., "Inhibition of Proteasome Activities and Subunit-Specific Amino-Terminal Threonine modification by Lactacystin," Science, (May 1995) 268:726-731.

Fenteany, et al., "Lactacystin, Proteasome Function, and Cell Fate," J. Biol. Chem. (1998) 273(15):8545-8548.

Fernandez-Chimeno, et al., "IB-96212, a Novel Cytotoxic Macrolide Produced by a Marine Micromonospora," Journal of Antibiotics, (May 2000) 53(5):474-478.

Fingl, et al., "General Principals," The Pharmaceutical Basis of Therapeutics, 5th Ed., (Goodman et al. Eds., 1975), MacMillan Publishing Co. Inc., New York, Chapter 1:1-46.

Folkman, Judah, "Angiogenesis-Dependent Diseases," Seminars in Oncology, (Dec. 2001) 28(6):536-542.

Folkman, Judah, "Tumor Angiogenesis," Adv Cancer Res., (1985) 43:175-203.

Fukuchi, et al., "Direct proteasome inhibition by clasto-lactacystin (-lactone permits the detection of ubiquitinated p21 in ML-1 Cells," Biochem. Biophys. Acta, (1999) 1451:206-210.

Gale, et al. (Eds.), The Molecular Basis of Antibiotic Action, 2nd ed., John Wiley and Sons, London (1981) Table of Contents, pp. 1-13.

Gantt, et al., "Proteasome Inhibitors Block Development of *Plasmodium* SPP", Antimicrobial Agents and Chemotherapy, (Oct. 1998) 2731-2738.

Geier, et al., "A Giant Protease with Potential to Substitute for Some Functions of the Proteasome," Science, (Feb. 1999) 283:978-981.

Gennaro, A.R. (Ed.), Remington's Pharmaceutical Sciences, 17th Ed., Mack Publishing Co., Easton, PA, (1985), Table of Contents, pp. 5.

Gennaro, A.R. (Ed.), Remington's Pharmaceutical Sciences, 18th Ed., Mack Publishing Co., Easton, PA (1990), Table of Contents, pp. 5.

Giannangeli et al., "Effect of Modifications of the Alkylpiperazine Moiety of Trazodone on 5HT2A and a1 Receptor Binding Affinity," J. Med. Chem., (Feb. 1999) 42(3):336-45.

Giovannoni, Stephen, "Oceans of Bacteria," Nature, (Jul. 29, 2004) 430:515-16.

Goldberg, et al., "Not Just Research Tools—Proteasome Inhibitors Offer Therapeutic Promise," Natural Medicine, (Apr. 2002) 8(4): 338-40.

Golub, et al., "Molecular Classification of Cancer; Class Discovery and Class Prediction by Gene Expression Monitoring", Science, (Oct. 1999) 286:531-37.

Goodfellow, et al., "Actinomycetes in Biotechnology", Okami, et al., ed., Chapter 2:"Search and Discovery of New Antibiotics", Academic Press, Harcourt Brace Jovanovich, (1988) 32-67.

Goodfellow, et al., "Actinomycetes in Marine Sediments," Biological Biochemical and Biomedical Aspects of Actinomycetes, Ortiz-Ortiz, et al., eds., Academic Press, Inc., Orlando (1984) 453-72.

Goodfellow, et al., "Ecology of Actinomycestes," Ann. Rev. Microbiol., (1983) 37:189-216.

Goodfellow, et al., "Search and Discovery of Industrially Significant Actinomycetes," Microbial Products: New Approaches, Society for General Microbiology Symposium, (1989) 44:343-83.

Grant, et al., "Intracellular Mechanisms Involved in Basement Membrane Induced Blood Vessel Differentiation In Vitro," In Vitro Cell Dev. Biol., (1991) 27A:327-36.

Grosios, et al., "Angiogenesis Inhibition by the Novel VEGF Receptor Tyrosine Kinase Inhibitor; PTK787/ZK222584, Causes Significant Anti-Arthritic Effects in Models of Rheumatoid Arthritis," Inflamm Res, (2004) 53: 133-142.

Hanna, et al., "On the Role of Macrophages in Anthrax," Proc. Natl. Acad. Sci. USA, (Nov. 1993) 90:10198-10201.

Hardt, et al., "Neomarinone, and New Cytotoxic Marinone Derivatives, Produced by a Marine Filamentous Bacterium (Actinomycetales)," Tetrahedron Letters, (2000) 41(13):2073-2076.

Harker, et al., "Multidrug Resistance in Mitoxantrone-Selected HL-60 Leukemia Cells in the Absence of P-Glycoprotein Overexpression", Cancer Res., (1989) 49(16): 4542-4549.

He, et al., "Lomaiviticins A and B, Potent Antitumor Antibiotics from *Micromonospora lomaivitiensis*," J. Am. Chem. Soc., (May 2001) 123(22):5362-5363.

Helmke, et al., "*Rhodococcus marinonascens* sp. nov.: An Actinomycete From the Sea," International J. of Systematic Bacteriology, (Apr. 1984) 34(2):127-138.

Hideshima, et al., "NF-κB as a Therapeutic Target in Multiple Myeloma," J. Biol. Chem., (2002) 277(19):16639-16647.

Higuchi, et al., "Pro-Drugs as Novel Delivery Systems," vol. 14, A.C.S. Symposium Series American Chemical Society, Atlantic City, NJ., Sep. 10, 1974, (1975) Table of Contents, pp. 3.

Hogan, et al., "Proteasome Inhibition by a Totally Synthetic β-Lactam Related to Salinosporamide A and Omuralide," J. Am. Chem. Soc., (2005) 127(44):15386-15387.

Hopwood, et al., "Genetic Manipulation of *Streptomyces* Polyketide Synthase Genes for Novel Secondary Metabolite Production," FEMS Microbiology Reviews, (1995) 16:233-234.

Horan, Ann C., "Aerobic Actinomycetes: A Continuing Source of Novel Natural Products," The Discovery of Natural Products with Therapeutic Potential (Biotechnology), Vincent P. Gullo (Ed.), Butterworth-Heinemann, Boston (1994) Chapter 1: 1-30.

Hull, et al., "Antiangiogenic Agents Are Effective Inhibitors of Endometriosis," J. Clinical Endocrinology Metabolism, (Jun. 2003) 88(6):2889-2899.

Jensen, et al., "Distribution of Actinomycetes in Near-Shore Tropical Marine Sediments," Applied and Environmental Microbiology, (Apr. 1991) 57(4):1102-1108.

Jensen, et al., "Strategies for the Discovery of Secondary Metabolites from Marine Bacteria: Ecological Perspectives," Annu. Rev. Microbiology, (1994) 48:559-584.

Jensen, et al., "The Relative Abundance and Seawater Requirements of Gram-Positive Bacteria in Near-Shore Tropical Marine Samples," Microbial Ecology, (1995) 29(3):249-257.

Jensen, et al., "Marine Microorganisms and Drug Discovery: Current Status and Future Potential," Drugs from the Sea, Nobuhiro Fusetani Ed., Krager, Basel Switzerland (2000) 6-29.

Jiang, et al., "Antinoflavoside, A Novel Flavonoid-Like Glycoside Produced by a Marine Bacterium of the Genus *Streptomyces*," Tetrahedron Letters, (1997) 38(29):5065-5068.

Johnson et al., "Relationships between drug activity in NCI preclinical in vitro and in vivo models and early clinical trials", British J Cancer, (2001) 84(11): 1424-1431.

Joseph, et al., "Laboratory Cultivation of Widespread and Previously Uncultured Soil Bacteria," Applied and Environmental Microbiology, (2003) 69(12):7210-7215.

Joshi, A., "Microparticulates for Ophthalmic Drug Delivery," J. Ocul. Pharmacol., (1994) 10:29-45.

Kalns, et al., "Delayed Treatment With Doxycycline Has Limited Effect on Anthrax Infection in BLK57/B6 Mice," Biochem. Biophys. Res. Commun., (2002) 297:506-509.

Kalns, et al., "TNF Receptor 1, IL-1 Receptor, and iNOS Genetic Knockout Mice Are Not Protected from Anthrax Infection," Biochem. Biophys. Res. Commun., (2002) 292:41-44.

Kerr, et al., "Marine Natural Products as Therapeutic Agents", Exp. Opinion on Therapeutic Patents, (1999) 9(9):1207-1222.

Kim, et al., "Sensitizing Anthrax Lethal Toxin-Resistant Macrophages to Lethal Toxin-Induced Killing by Tumor Necrosis Factor," J. Biol. Chem., (2003) 278:7413-7421.
King, et al., "How Proteolysis Drives the Cell Cycle," Science, (1996) 274:1652-1659.
Kisselev, et al., "Proteasome Inhibitors: From Research Tools to Drug Candidates," Chem. Biol., (2001) 8:739-758.
Kisselev et al., "Importance of the Different Proteolytic Sites of the Proteasome and the Efficacy of Inhibitors Varies with the Protein Substrate," J Bio Chem., (Mar. 2006) 281(13): 8582-8590.
Koch, et al., "16S Ribosomal DNA Analysis of the Genera *Micromonospora*, Actinoplanes, Catellatospora, Catenuloplanes, Dactylosporangium, and Pillimelia and Emendation or the Family Micromonosporaceae," Intl Journal of Systematic Bacteriology, (Jul. 1996) 46(3):765-768.
Kozlowski, et al., "Lactacystin Inhibits Cathepsin A Activity in Melanoma Cell Lines," Tumor Biol., (2001) 22:211-215.
Lacy, et al., "Mapping the Anthrax Protective Antigen Binding Site on the Lethal and Edema Factors," J. Biol. Chem., (2002) 277:3006-3010.
Lam, et al., "Isolation of a Bromo Analog of Rebeccamycin From *Saccharothrix aerocolonigenes*," J. Antibiotics, (Sep. 1991) 44(9):934-939.
Lam, et al., "Production, Isolation and Structure Determination of Novel Fluoroindolocarbazoles from *Saccharothrix aerocolonigenes* ATCC 39243," J. Antibiotics, (2001) 54(1):1-9.
Lawley, et al., "Induction of Morphologic Differentiation of Endothelial Cells in Culture," J. Investigative Dermatology, (Aug. 1989) 93(2 Supplement):59S-61S.
Lenz, et al., "Clinical Update: Proteasome Inhibitors in Solid Tumors", Cancer Treatment Reviews, (2003) 29 (1 Supplement):41-48.
Lightcap, et al., "Proteasome Inhibition Measurements Clinical Application," Clin. Chem., (2000) 46(5):673-683.
Lin, et al., "Cytotoxic Effects of Anthrax Lethal Toxin on Macrophage-Like Cell Line J774A.1," Curr. Microbiol., (1996) 33:224-227.
Liu, et al., "Angiogenesis Inhibitors May Regulate Adiposity," Nutr. Rev., (2003) 61:384-387.
Liu, et al., "Precursor Supply for Polyketide Biosynthesis: The Role of Crotonyl-CoA Reductase," Metab. Eng., (2001) 3:40-48.
Macherla, et al., "Structure-Activity Relationship Studies of Salinosporamide A (NPI-0052), a Novel Marine Derived Proteasome Inhibitor," J. Med. Chem., (2005) 48(11): 3684-3687.
Manchand, et al., "Syntheses of the Anti-AIDS Drug 2',3'-Dideoxycytidine from Cytidine," J. Org. Chem., (1992) 57:3473-3478.
Mayer, et al., "Efficacy of a Novel Hydrogel Formulation in Human Volunteers," Ophthalmologica, (1996) 210(2):101-103.
Mayer, et al., "Marine Pharmacology in 1999: Antitumor and Cytotoxic Compounds." Anticancer Res. (Jul./Aug. 2001) 21(4A): 2489-2500.
McMurry, John, Organic Chemistry, 5th ed., Brooks/Cole, Pacific Grove, CA. (2000), Chapter 11.5, pp. 398-408.
Meng, et al., "Eponemycin Exerts its Antitumor Effect Through the Inhibition of Proteasome Function," Cancer Res., (1999), 59(12):2798-2801.
Meng, et al., "Epoxomicin, a Potent and Selective Proteasome Inhibitor, Exhibits In Vivo Anti-Inflammatory Activity," Proc. Natl. Acad. Sci. USA, (Aug. 1999) 96:10403-10408.
Merriam-Webster Online Dictrionary, "Heteroatom", 2010, Merriam-Webster Online, accessed Jun. 16, 2010, http://merriam-webster.com/dictionary/heteroatom.
Min, et al., "Urokinase Receptor Antagonists Inhibit Angiogenesis and Primary Tumor Growth in Syngeneic Mice," Cancer Res., (May 15, 1996) 56(10):2428-2433.
Mincer, et al., "Widespread and Persistent Populations of a Major New Marine Actinomycete Taxon in Ocean Sediments," Applied and Environmental Microbiology, (Oct. 2002) 68(10):5005-5011.
Mogridge, et al., "Stoichiometry of Anthrax Toxin Complexes," Biochemistry, (2002) 41:1079-1082.
Momose, et al., "2(3H)-and 2(5H)-Furanones. VII. Chirality Transfer on the Tetronic Acid Templates," Heterocycles, (1999) 51(6):1321-1343.
Moore, B.S., "Biosynthesis of Marine Natural Products: Microorganisms and Macroalgae," Nat. Prod. Rep., (1999) 16(6):653-674.
Moran, et al., "Evidence for Indigenous *Streptomyces* Populations in Marine Environment Determined with a 16S rRNA Probe," Applied and Environmental Microbiology, (Oct. 1995) 61(10):3695-3700.
Mordenti, et al., "Intracular Pharmacokinetics and Safety of a Humanized Monoclonal Antibody in Rabbits after Intravitreal Administration of a Solution or a PLGA Microsphere Formulation," Toxicol. Sci., (1999) 52(1):101-106.
Mousa, et al., "Angiogenesis Inhibitors: Current & Future Directions," Current Pharmaceutical Design, (2004) 10:1-9.
Mulholland et al., "A Concise Total Synthesis of Salinosporamide A," Org. Biomol. Chem., (2006) 4: 2845-6.
Murray, J. Clifford (Ed.), Angiogenesis Protocols (Methods in Molecular Medicine), Humana Press, Totowa, NJ. (2001) Table of Contents, p. 4.
Mutomba, et al., "Inhibition of Proteasome Activity Blocks Cell Cycle Progression at Specific Phase Boundaries in African Trypanosomes", Mol. Biochem. Parasitology, (1997) 90:491-504.
NCBI website, sequence for AB242910, http://www.ncbi.nlm.nih.gov/entrez/viewer.fcgi?db=nucleotide&val=124300751, 2 pages, downloaded Feb. 15, 2007, 2 pages.
NCBI website, sequence for EF105548, http://www.ncbi.nlm.nih.gov/entrez/viewer.fcgi?db=nucleotide&val=118640518, 2 pages, downloaded Feb. 15, 2007, 2 pages.
NCBI website, Sequence for EF191171, http://www.ncbi.nlm.nih.gov/entrez/viewer.fcgi?db=nucleotide&val=124014014, 2 Pages, downloaded Feb. 15, 2007, 2 pages.
Nesterneko, et al., "*Rhodococcus luteus* nom. nov., and *Rhodococcus maris* nom. nov.", Int'l Journal of Systematic Bacteriology, (Jan. 1982) 32(1):1-14.
Newton. "Il fondo agli oceani potenti antibiotici e anticancro." www.newton.rcs.it/PrimoPiano/News/2003/02_Febbraio/03/Antobiotico.html. (Feb. 2, 2003) 1 page.
Nicholson, D.W., "ICE/CED 3-Like Proteases as Therapeutic Targets for the Control of Inappropriate Apoptosis," Nat. Biotechnology, (1996) 14:297-301.

Nicolaus B.J. R. "Symbiotic Approach to Drug Design," Decision Making in Drug Research, (1983) 173-186.

Nicosia, et al., "Growth of Microvessels in Serum-Free Matrix Culture of Rat Aorta: A Quantitative Assay of Angiogenesis In Vitro," Laboratory Investigation, (Jul. 1990) 63(1):115-122.

Nolan, et al., "Isolation and Screening of Actinomycetes," Actinomycetes in Biotechnology, (1988) Chapter 1:1-32.

O'Donnel, Anthony G., "Recognition of Novel Actinomycetes," Actinomycetes in Biotechnology, Academic Press, (1988) Chapter 3:69-88.

Oikawa, et al., "Angiogenic Factor of a Rat Mammary Tumor Cell Line (RMT-1) (I). Secretion of Two Distinct Angiogenic Factors into Serum-Free Conditioned Medium by RMT-1 Cells," Cancer Letters, (1991) 59:57-66.

Okami, Y., "The Search for Bioactive Metabolites from Marine Bacteria," J. Marine Biotechnology, (1993) 1: 59-65.

Omura, et al., "Lactacystin, A Novel Microbial Metabolite, Induces Neuritogenesis of Neuroblastoma Cells," J. Antibiotics, (1991) 44(1): 113-116.

O'Neil et al. eds., "The Merck Index," 13th Ed. 2001, Merck Research Laboratories, Whitehouse Station N.J., pp. THER-5-THER-7.

Online URL: Hyperlink "http://aidsinfo.nih.gov/DrugsNew/DrugDetailNT.aspx?Menultem=Drugs&Search=On&int_id=244" "blocked::http://aidsinfo.nih.gov/DrugsNew/DrugDetailNT.aspx?Menultem=Drugs&Search=On&int_id=244"; Nov. 22, 2010; pp. 1-2.

Online URL:http://en.wikipedia.org/wiki/Myeloma; pp. 1-8.

Online URL:http://en.wikipedia.org/wiki/Sarcoma; pp. 1-2.

Online URL:http://web.archive.org/web/20060117081111/hivhep.tempdomainname.com/hiv and aids/norvir effects... Nov. 22, 2010. 1 page.

Online www.netdoctor.co.uk "Isoniazid: Treatment of Tuberculosis", [accessed on Apr. 8, 2008] pp. 1-2.

Ostrowska, et al., "Lactacystin, A Specific Inhibitor of the Proteasome, Inhibits Human Platelet Lysosomal Cathepsin A-like Enzyme," Biochem. Biophys. Res. Commun., (1997) 234:729-732.

Ostrowska, et al., "Separation of Cathepsin A-like Enzyme and the Proteasome: Evidence that Lactacystin/(-Lactone is not a Specific Inhibitor of the Proteasome," Int. J. Biochem. Cell Biol., (2000) 32:747-757.

Otoguro, et al., "An intergrated method for the enrichment and selective isolation of *Actinokineospora* spp. in soil and plant litter," J. Appl. Microbiol., (2001) 92:118-130.

Pagano, et al., "Role of the Ubiquitin-Proteasome Pathway in Regulating Abundance of the Cyclin-Dependent Kinase Inhibitor p27," Science, (1995) 269(5224):682-685.

Page, Roderic D.M., "TreeView: An Application to Display Phylogenetic Trees on Personal Computers," Computer Applications in the Biosciences, (1996) 12:357-358.

Painter, Robert B., "Inhibition of DNA Replicon Initiation by 4-Nitroquinoline 1-Oxide, Adriamycin, and Ethyleneimine," Cancer Res., (1978) 38(12):4445-4449.

Palayoor, et al., "Constitutive Activation of I(B Kinase ( and NF-(B in Prostate Cancer Cells is Inhibited by Ibuprofen," Oncogene, (1999) 18:7389-7394.

Peckham et al. (Eds.), "The Oxford Textbook of Oncology," Oxford University Press, Oxford (1995) vol. 1:447-453.

Pieters et al., "Microbiology: Chemical Warfare and Mycobacterial Defense", Science, (Dec. 2003) 302:1900-1902.

Plunkett, et al., "Methods in Laboratory Investigation: An In Vivo Quantitative Angiogenesis Model Using Tumor Cells Entrapped in Alginate," Laboratory Investigation, (Apr. 1990) 62(4):510-517.

Prudhomme et al., "Marine Actinomycetes: A New Source of Compounds against the Human Malaria Parasite," Plos One, (2008) 3(6): 1-8.

Qureshi, et al., "The Proteasome as a Lipopolysaccharide-Binding Protein in Macrophages: Differential Effects of Proteasome Inhibition on Lipopolysaccharide-Induced Signaling Events," J. Immunol., (2003) 171(3):1515-1525.

Rappe, et al., "Cultivation of the Ubiquitous SAR11 Marine Bacterioplankton Clade," Nature, (Aug. 8, 2002) 418:630-633.

Reddy, et al., "A Simple Stereocontrolled Synthesis of Salinosporamide A," J. Am. Chem. Soc., (2004) 126(20):6230-6231.

Reed et al., "Salinosporamides D-J from the Marine Actinomycete *Salinispora tropica*, Bromosolinosporamide, and Thioester Derivatives Are Potent Inhibitors of the 20S Proteasome", J Nat Prod., (2007) 70: 269-276.

Riva, S., "Biocatalytic Modification of Natural Products," Curr. Opin. Chem. Biol., (2001) 5:106-111.

Roche, Edward B. (Ed.), "Bioreversible Carriers in Drug Design: Theory and Application," Pergamon Press, Elmsford, NY (1987), pp. 14-21.

Rockwell, et al., "Proteasome Inhibition in Neuronal Cells Induces a Proinflammatory Response Manifested by Upregulation of Cyclooxygenase-2, Its Accumulation as Ubiquitin Conjugates, and Production of the Prostaglandin PGE2," Arch. Biochem. And Biophysics, (2000) 374(2):325-333.

Romero, et al., "Thiocoraline, a New Depsipeptide with Antitumor Activity Produced by a Marine *Micromonospora*," J. Antibiotics, (1997) 50(9):734-737.

Rubanyi, Gabor M., "Angiogenesis in Health and Disease: Basic Mechanisms and Clinical Applications", Marcel Dekker, New York, NY (1999) pp. 6 Content Pages Only.

Ruiz, et al., "The Proteasome Inhibitor NPI-0052 is a More Effective Inducer of Apoptosis than Bortezomib in Lymphocytes from Patients with Chronic Lymphocytic Leukemia," Mol. Cancer Ther., (2006) 5(7): 1836-1843.

Sapi, et al., "Simple and Condensed (-Lactam. Part 32. Base- and Acid-Catalyzed Ring Expansions of 3-Substituted 4-Acetylazetidin-2-ones and Related Compounds". Collect. Czech. Chem. Commun. (1999) 64(2):190-202.

Saravanan, et al., "A Short, Stereocontrolled, and Practical Synthesis of (-Methylomuralide, a Potent Inhibitor of Proteasome Function," J. Org. Chem., (2003) 68(7):2760-2764.

Sausville et al., "Contributions of human tumor xenografts to anticancer drug development", Cancer Res. (2006)66(7): 3351-3354.

Schiewe, H. (Reprint) Haustedt, et al., "Rational approaches to natural-product-based drug design", Curr Opin Drug Disc Devel. (2006) 9(4):445-462.

Schnaper, et al., "Plasminogen Activators Augment Endothelial Cell Organization In Vitro by Two Distinct Pathways," J. Cell. Physiol., (1995) 165:107-118.

Shadomy, et al., "Antimycotic and Antirickettsial," Antibiotics, Chemotherapeutics, and Antibacterial Agents for Disease Control, Martin Grayson (Ed.) John Wiley and Sons, New York (1982) 371-395.

Shah, et al., "Early Clinical Experience With the Novel Proteasome Inhibitor PS-519," J. Clin. Pharmacol., (2002) 54:269-276.

Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicenter Study," Clin. Ther., (2001) 23(3):440-450.

Shimada, et al., "Contributions of Mitogen-Activated Protein Kinase and Nuclear Factor Kappa B to N-(4-hydroxyphenyl) Retinamide-Induced Apoptosis in Prostate Cancer Cells," Molecular Carcinogenesis, (2002) 35(3):127-137.

Shoemaker, R., "The NCI60 Human Tumour Cell Line Anticancer Drug Screen," Nature Reviews Cancer, (2006) 6:813-823.

Silva-Jardim, et al., "The *Leishmania chagasi* Proteasome: Role in Promastigotes Growth and Amastigotes Survival within Murine Macrophages", Acta Tropica, (2004) 91:121-130.

Silverman, Richard B., The Organic Chemistry of Drug Design and Drug Action, Academic Press, San Diego, (1992) 19-21.

Stach, et al., "New Primers for the Class Actinobacteria: Application to Marine and Terrestrial Environments," Environmental Mircrobiology, (2003) 5(10):828-841.

Stach, et al., "Statistical Approaches for Estimating Actinobacterial Diversity in Marine Sediments," Appl. Environ.I Mircrobiol., (Oct. 2003) 69(10):6189-6200.

Stackebrandt, et al., "Proposal for a New Hierarchic Classification Systems, Actinobacteria classis Nov.," Int. J. of Syst. Bacteriol., (Apr. 1997) 47(2):479-491.

Stackebrandt, et al., "Taxonomic Note: A Place for DNA-DNA Reassociation and 16S rRNA Sequence Analysis in the Present Species Definition in Bacteriology," Int. J. of Syst. Bacteriol., (Oct. 1994) 44(4):846-849.

Stadler et al., "Cinnabaramides A-G: Analogues of Lactacystin and Salinosporamide from a Terrestrial Streptomycete," J. Nat. Prod. (Feb. 2007) 70(2):246-252.

Stanford, et al., "Bortezomib Treatment for Multiple Myeloma," Ann. Pharmacother., (2003) 37:1825-1830.

Stella et al., (Ed.), "Prodrugs: Challenges and Rewards, Part 1", American Association of Pharma. Scientists (2007), p. 24.

Streitwieser et al., Introduction to Organic Chemistry, 2nd ed., Macmillan Publishing Co. Inc., New York, NY (1981) pp. 169-171.

Sunwoo, et al., "Novel Proteasome Inhibitor PS-341 Inhibits Activation of Nuclear Factor-kB, Cell Survival, Tumor Growth, and Angiogenesis in Squamous Cell Carcinoma," Clin. Cancer Res., (2001) 7:1419-1428.

Tabuchi, et al., "Application of 'Proteasome Tolerance' to Therapies for Neurodegenerative Disease," Alzheimer's and Dementia, (2006) 2(3) (1 Supplement):S628.

Takeuchi, et al., "Troglitazone Induces G1 Arrest by p27 Induction That Is Mediated by Inhibition of Proteasome in Human Gastric Cancer Cells," Jpn. J. Cancer Res., (2002) 93:774-782.

Tang, et al., "Cloning and Hererologous Expression of the Epothilong Gene Cluster," Science, (Jan. 28, 2000) 287:640-642.

Tang, et al., "Proteasome Activity is Required for Anthrax Lethal Toxin to Kill Macrophages," Infect. Immun., (1999) 67(6):3055-3060.

Tauchi, et al., "Molecular Mechanisms of Resistance of Leukemia to Imatinib Mesylate," Leukemia Research, (May 2004) 28:39-45.

Thompson, et al., "CLUSTAL W: improving the sensitivity of progressive multiple sequence alignment through sequence weighting, position-specific gap penalties and weight matrix choice," Nucleic Acids Research, (1994) 22(22):4673-4680.

Versalovic, et al., "Distribution of repetitive DNA sequences in eubacteria and application to fingerprinting of bacterial genomes," Nucleic Acids Research, (1991) 19(24):6823-6831.

Vitale, et al., "Anthrax lethal factor cleaves the N-terminus of MAPKKS and induces tyrosine/threonine phosphorylation of MAPKS in cultured macrophages," J. Applied Microbiology, (1999) 87:288.

Vitale, et al., "Susceptibility of Mitogen-Activated Protein Kinase Kinase Family Members to Proteolysis by Anthrax Lethal Factor," Biochem. J., (2000) 352:739-745.

Ward, Bess B., "How Many Species of Prokaryotes are There?" Proc. Natl. Acad. Sci. USA, (Aug. 6, 2002) 99(16):10234-10236.

Watve, et al., "How Many Antibiotics are Produced by the Genus *Streptomyces*?" Arch. Microbio., (2001) 176:386-390.

Weyland, H., "Actinomycetes in North Sea and Atlantic Ocean Sediments," Nature, (1969) 223:858.

Weyland, H., "Distribution of Actinomycetes on the Sea Floor," Actinomycetes ZBL. Bakt. Suppl., (1981) 11:185-193.

Wheelis, et al., "On the Nature of Global Classification," Proc. Natl. Acad. Sci. USA, (Apr. 1992) 89:2930-2934.

Williams et al., "New Cytotoxic Salinosporamides from the Marine Actinomycete *Salinispora tropica*," J. Org. Chem., (2005) 70(16):6196-6203.

Woese, Carl R., "Bacterial Evolution," Microbiological Rev., (Jun. 1987) 51(2):221-271.

Yew, et al., "Proteasome Inhibition by Lactacystin in Primary Neuronal Cells Induces Both Potentially Neuroprotective and Pro-Apoptotic Transcriptional Responses: a Microarray Analysis," J. Neurochem., (2005) 94(4):943-956.

Zaks, A., "Industrial Biocatalysis," Curr. Opin. Chem. Biol., (2001) 5:130-136.

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia," Stroke, (2001) 2926-2931.

Zheng, et al., "Detection of Antitumor and Antimicrobial Activities in Marine Organism Associated Actinomycetes Isolated From the Taiwan Strait, China," FEMS Microbiology Letters, (2000) 188:87-91.

International Search Report and Written Opinion dated Jul. 12, 2006 in International Application No. PCT/US2005/044091, International Filing Date: Dec. 2, 2005.

International Preliminary Report on Patentability dated Jun. 14, 2007 in International Application No. PCT/US2005/044091, International Filing Date: Dec. 2, 2005.

International Search Report and Written Opinion (corrected version) dated Jul. 8, 2005 in International Application No. PCT/US2004/019543, International Filing Date: Jun. 18, 2004.

International Preliminary Report on Patentability dated Jan. 3, 2006 in International Application No. PCT/US2004/019543, International Filing Date: Jun. 18, 2004.

International Preliminary Report on Patentability dated Mar. 14, 2005 in International Application No. PCT/US2004/019453, International Filing Date: Jun. 18, 2004.

Written Opinion dated Nov. 29, 2004 in International Application No. PCT/US2004/019453, International Filing Date: Jun. 18, 2004.

International Search Report and Written Opinion dated Dec. 29, 2006 in International Application No. PCT/US2005/014846, International Filing Date: Apr. 29, 2005.

International Preliminary Report on Patentability dated Jan. 23, 2007 in International Application No. PCT/US2005/014846, International Filing Date: Apr. 29, 2005.

International Search Report dated Aug. 2, 2002 in International Application No. PCT/US01/043758, International Filing Date: Nov. 16, 2001.

International Preliminary Report on Patentability dated Aug. 24, 2004 in International Application No. PCT/US2001/043758, International Filing Date: Nov. 16, 2001.

International Search Report and Written Opinion dated Feb. 27, 2007 in International Application No. PCT/US06/016104, International Filing Date: Apr. 27, 2006.

International Preliminary Report on Patentability dated Oct. 30, 2007 in International Application No. PCT/US2006/016104, International Filing Date: Apr. 27, 2006.

International Search Report and Written Opinion mailed Jan. 29, 2009 for corresponding International Application No. PCT/US2008/062553 International Filing Date: May 2, 2008.

International Preliminary Report on Patentability dated Nov. 19, 2009 in International Application No. PCT/US2008/062553, International Filing Date: May 2, 2008.

International Search Report and Written Opinion dated Sep. 28, 2009 for International Application No. PCT/US2009/043644, International Filing Date: May 12, 2009.

International Preliminary Report on Patentability (Chapter II) dated Aug. 6, 2010 for International Application No. PCT/US2009/043644, International Filing Date: May 12, 2009.

International Search Report and Written Opinion dated May 12, 2006 in International Application No. PCT/US2005/043668, International Filing Date: Dec. 2, 2005.

International Preliminary Report on Patentability dated Jun. 14, 2007 in International Application No. PCT/US2005/043668, International Filing Date: Dec. 2, 2005.

International Search Report and Written Opinion dated Nov. 15, 2005 in International Application No. PCT/US2005/012218, International Filing Date: Apr. 11, 2005.

International Preliminary Report on Patentability dated Oct. 11, 2006 in International Application No. PCT/US2005/012218, International Filing Date: Apr. 11, 2005.

International Search Report and Written Opinion dated Oct. 19, 2005 in International Application No. PCT/US2005/012113, International Filing Date: Apr. 11, 2005.

International Preliminary Report on Patentability dated Oct. 11, 2006 in International Application No. PCT/US2005/012113, International Filing Date: Apr. 11, 2005.

International Search Report and Written Opinion dated Jan. 10, 2007 in International Application No. PCT/US2006/031314, International Filing Date: Aug. 10, 2006.

International Preliminary Report on Patentability dated Feb. 12, 2008 in International Application No. PCT/US2006/031314, International Filing Date: Aug. 10, 2006.

International Search Report and Written Opinion dated Aug. 3, 2007 in International Application No. PCT/US2006/035196, International Filing Date: Sep. 8, 2006.
International Preliminary Report on Patentability dated Mar. 18, 2008 in International Application No. PCT/US2006/035196, International Filing Date: Sep. 8, 2006.
EFS File History of U.S. Appl. No. 09/991,518, filed Nov. 16, 2001.
EFS File History of U.S. Appl. No. 10/600,854, filed Jun. 20, 2003.
EFS File History of U.S. Appl. No. 10/821,621, filed Apr. 9, 2004.
EFS File History of U.S. Appl. No. 10/838,157, filed Apr. 30, 2004.
EFS File History of U.S. Appl. No. 10/871,368, filed Mar. 3, 2005.
EFS File History of U.S. Appl. No. 11/118,260, filed Apr. 29, 2005.
EFS File History of U.S. Appl. No. 11/147,622, filed Jun. 7, 2005.
EFS File History of U.S. Appl. No. 11/224,589, filed Sep. 12, 2005.
EFS File History of U.S. Appl. No. 11/228,416, filed Sep. 15, 2005.
EFS File History of U.S. Appl. No. 11/293,354, filed Dec. 2, 2005.
EFS File History of U.S. Appl. No. 11/412,476, filed Apr. 27, 2006.
EFS File History of U.S. Appl. No. 11/453,374, filed Jun. 15, 2006.
EFS File History of U.S. Appl. No. 11/539,648, filed Oct. 9, 2006.
EFS File History of U.S. Appl. No. 11/705,694, filed Feb. 12, 2007.
EFS File History of U.S. Appl. No. 11/841,588, filed Aug. 20, 2007.
EFS File History of U.S. Appl. No. 11/865,704, filed Oct. 1, 2007.
EFS File History of U.S. Appl. No. 11/966,787, filed Dec. 28, 2007.
EFS File History of U.S. Appl. No. 11/966,801, filed Dec. 28, 2007 as of Mar. 24, 2011].
EFS File History of U.S. Appl. No. 12/028,024, filed Feb. 8, 2008.
EFS File History of U.S. Appl. No. 12/114,449, filed May 2, 2008.
EFS File History of U.S. Appl. No. 12/136,688, filed Jun. 10, 2008 as of Jan. 20, 2011.
EFS File History of U.S. Appl. No. 12/183,007, filed Jul. 30, 2008.
EFS File History of U.S. Appl. No. 12/464,686, filed May 12, 2009.
EFS File History of U.S. Appl. No. 12/638,860, filed Dec. 15, 2009 as of May 16, 2011.
Andtbacka, et al., "The Proteasome Inhibitor NPI-0052 Sensitizes Pancreatic Cancer Cells to TRAIL In Vitro and In Vivo," Amer. Assoc. Cancer Res., (2005) 46: Abstract #1721.
Andtbacka, et al., "The Proteasome Inhibitor NPI-0052 Overcomes TRAIL Resistance in Human Pancreatic Cancer Cells In Vitro and In Vivo," Cancer Research, (2007) (under revision).
Barral, et al., "The Proteasome Inhibitor NPI-0052 Reduces Tumor Growth and Overcomes Resistance of Prostate Cancer to rhTRAIL via Inhibition of the NF-kB Pathway," Amer. Assoc. Cancer Res., (2007): abstract 1465.

Cusack, et al., "Oral proteasome inhibitor (NPI-0052) enhances sensitivity to combination Gemcitabine and Erbitux in a pancreatic cancer xenograft model," Nereus Pharmaceuticals, Inc., (Apr. 19, 2005), abstract 4943 for presentation at the American Association of Cancer Research Annual Meeting held on Apr. 19, 2005 in Orange County, CA, 1 page.
Khanbolooki, et al., "Novel NFκB inhibitors NPI-1342/NPI-1387 and proteasome inhibitor NPI-0052 overcome resistance of pancreatic carcinoma to rhTRAIL," Nereus Pharmaceuticals, Inc., (Apr. 2, 2006), abstract 780 for presentation at the American Association of Cancer Research Annual Meeting held on Apr. 2, 2006 in Washington, D.C., 1 page.
Lala et al., "Role of nitric oxide in tumor progression: lessons from experimental tumors", Cancer Metastasis Rev. (1998) 17(1):91-106.
Okami, et al., "Search and Discovery of New Antibiotics", Actinomycetes in Biotechnology, Academic Press (1988) Chapter 2:33-67.
Ogiso, et al., "Proteosome Inhibition Circumvents Solid Tumor Resistance to Topoisomerase II-directed Drugs," *Cancer Research*, (2000) 60:2429-2434.
Roccaro, et al., "Dual Targeting of the Proteasome Regulates Survival and Homing in Waldenstrom Macroglobulinemia." Blood, (Mar. 2008) 111(9): 4752-4763.
Suzuki, et al., "Chemosensitization of Drug and Rituximab-Resistant Daudi B-NHL Clones to Drug-Induced Apoptosis by the Proteasome Inhibitor NPI-0052," Blood, (2005) 106:1521 abstract.
Tomida, et al., "Drug Resistance Pathways As Targets", Anticancer Drug Development, Academic Press, (2002) Chapter 5:77-90.
Voskoglou-Nomikos, et al., "Clinical Predictive Value of the in Vitro Cell Line, Human Xenograft, and Mouse Allograft Preclinical Cancer Models", *Clin Cancer Res.*, (2003) 9:4227-4239.
EFS File History of U.S. Appl. No. 12/136,688, filed Jun. 10, 2008 as of Dec. 30, 2011.
EFS File History of U.S. Appl. No. 12/638,860, filed Dec. 15, 2009 as of Jan. 3, 2012.
EFS File History of U.S. Appl. No. 10/561,711, filed Sep. 11, 2009 as of Nov. 28, 2011.
EFS File History of U.S. Appl. No. 12/720,557, filed Mar. 9, 2010 as of Dec. 9, 2011.
EFS File History of U.S. Appl. No. 13/052,827, filed Mar. 21, 2011 as of Jan. 3, 2012.
EFS File History of U.S. Appl. No. 12/183,007, filed Jul. 30, 2008 as of Nov. 7, 2011.

* cited by examiner

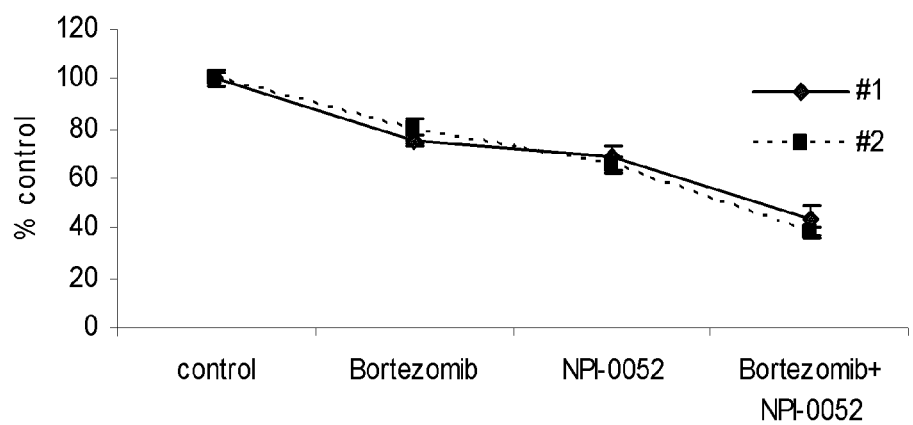
**FIG. 4E*i***
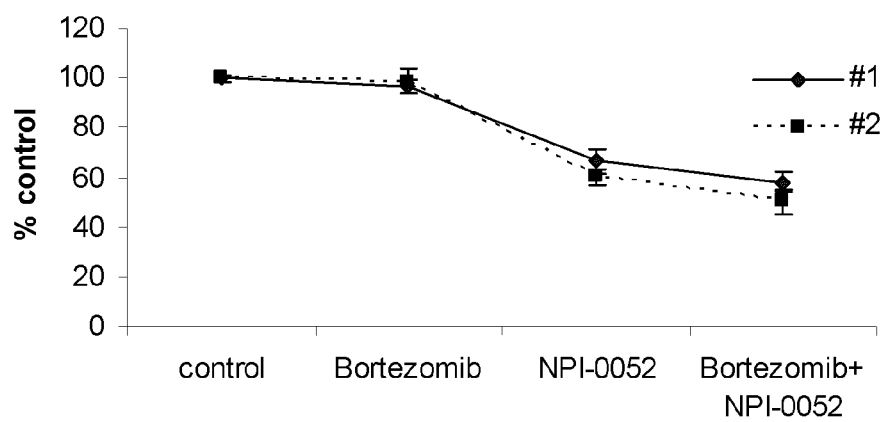
**FIG. 4E*ii***

FIG. 4E*iii*

METHODS OF USING [3.2.0] HETEROCYCLIC COMPOUNDS AND ANALOGS THEREOF IN TREATING WALDENSTROM'S MACROGLOBULINEMIA

RELATED APPLICATION

This application claims the benefit of U.S. Provisional Application No. 61/012,396, filed Dec. 7, 2007, which is incorporated herein by reference in its entirety.

BACKGROUND OF THE INVENTION

1. Field of the Invention

The present invention relates to certain compounds and to methods for the preparation and the use of certain compounds in the fields of chemistry and medicine.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Waldenström's Macroglobulinemia (WM) is a biologically unique low-grade B-cell lymphoma. WM is characterized by the presence of lymphoplasmacytic cells in the bone marrow and the secretion of IgM monoclonal protein in the serum, indicating that WM cells present a high protein turnover. WM is becoming a model low-grade lymphoma to test and validate therapeutic compounds that are specifically active in this biologically unique malignancy.

Therefore, a need exists for additional chemotherapeutic agents to treat cancer and more specifically WM. A continuing effort is being made by individual investigators, academia and companies to identify new, potentially useful chemotherapeutic agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

The embodiments disclosed herein generally relate to chemical compounds, including heterocyclic compounds and analogs thereof.

In some embodiments, the compounds are used to treat WM. Certain embodiments relate to methods of treating WM in animals. The method can include, for example, administering an effective amount of a compound to a patient in need thereof. Other embodiments relate to the use of compounds in the manufacture of a pharmaceutical or medicament for the treatment of WM.

The compounds can be administered or used in combination with treatments such as chemotherapy, radiation, and biologic therapies. In some embodiments the compounds can be administered or used with a chemotherapeutic agent. Examples of such chemotherapeutics include alkaloids, alkylating agents, antibiotics, antimetabolites, enzymes, hormones, platinum compounds, immunotherapeutics (antibodies, T-cells, epitopes), BRMs, and the like. Examples include, Vincristine, Vinblastine, Vindesine, Paclitaxel (Taxol), Docetaxel, topoisomerase inhibitors epipodophyllotoxins (Etoposide (VP-16), Teniposide (VM-26)), Camptothecin, nitrogen mustards (cyclophosphamide Cytoxan), Nitrosoureas, Carmustine, lomustine, dacarbazine, hydroxymethylmelamine, thiotepa and mitocycin C, Dactinomycin (Actinomycin D), anthracycline antibiotics (Daunorubicin, Daunomycin, Cerubidine), Doxorubicin (Adriamycin), Idarubicin (Idamycin), Anthracenediones (Mitoxantrone), Bleomycin (Blenoxane), Plicamycin (Mithramycin, Antifolates (Methotrexate (Folex, Mexate)), purine antimetabolites (6-mercaptopurine (6-MP, Purinethol) and 6-thioguanine (6-TG). The two major anticancer drugs in this category are 6-mercaptopurine and 6-thioguanine, Chlorodeoxyadenosine and Pentostatin, Pentostatin (2'-deoxycoformycin), pyrimidine antagonists, Avastin, Leucovorin, Oxaliplatin, fluoropyrimidines (5-fluorouracil (Adrucil), 5-fluorodeoxyuridine (FdUrd) (Floxuridine)), Cytosine Arabinoside (Cytosar, ara-C), Fludarabine, L-ASPARAGINASE, Hydroxyurea, glucocorticoids, antiestrogens, tamoxifen, nonsteroidal antiandrogens, flutamide, aromatase inhibitors Anastrozole (Arimidex), Cisplatin, 6-Mercaptopurine and Thioguanine, Methotrexate, Cytoxan, Cytarabine, L-Asparaginase, Steroids: Prednisone and Dexamethasone. Also, proteasome inhibitors such as bortezomib and carfilzomib (PR-171) can be used in combination with the instant compounds, for example. Examples of biologics can include agents such as TRAIL, antibodies to TRAIL and agonistic antibodies TRAIL death receptors DR4 and DR5, integrins such as alpha-V-beta-3 ($\alpha V\beta 3$) and/or other cytokine/growth factors that are involved in angiogenesis, VEGF, EGF, FGF and PDGF and antibodies to these cytokines/growth factors such as Erbitux. In some aspects, the compounds can be conjugated to or delivered with an antibody.

In other embodiments, the compounds are administered in combination with a histone deacetylase inhibitor (HDACi). In various embodiments, the HDACi is selected from the group consisting of:

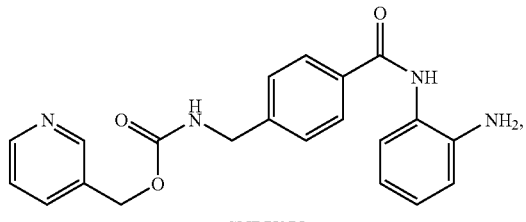

SNDX275

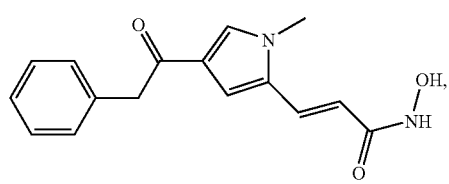

APHA compound 8

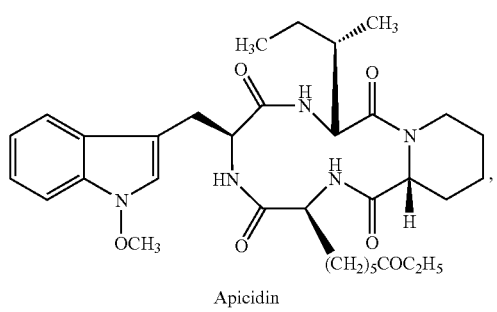

Apicidin

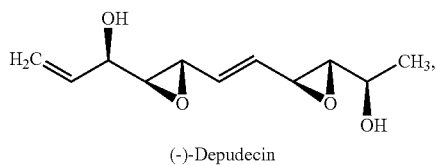

(-)-Depudecin

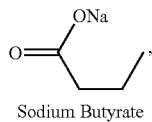

Sodium Butyrate

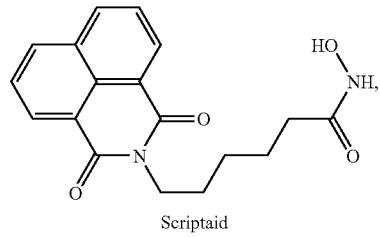

Scriptaid

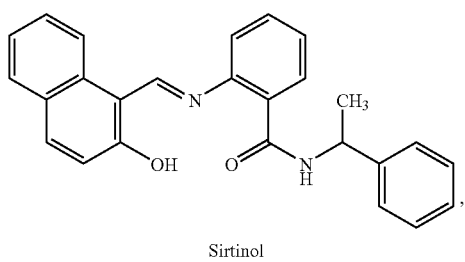

Sirtinol

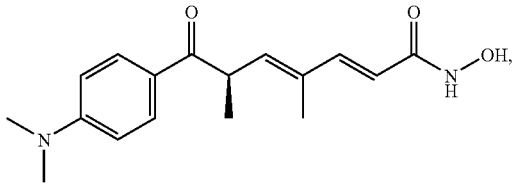

Trichostatin A

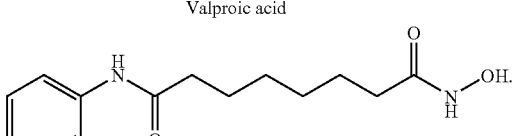

Valproic acid

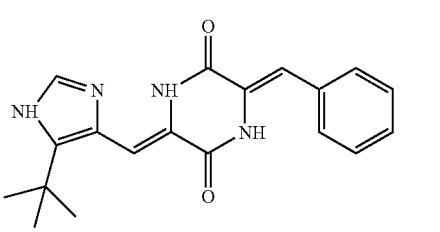

Vorinostat (suberoylanilide hydroxamic acid (SAHA))

In other embodiments, the compounds can be used in combination with vascular disrupting agents (VDA). Examples of such VDAs include combratostatin CA4P and NPI-2358. NPI-2358 is represented by the following formula:

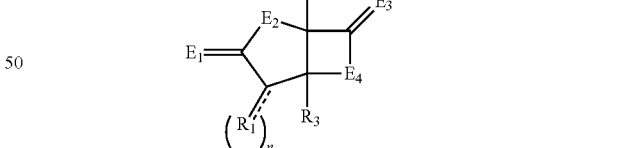

NPI-2358

Some embodiments relate to uses of a structure of Formula I, or a pharmaceutically acceptable salt or pro-drug ester thereof:

Formula I wherein $R_1$, $R_3$, and $R_4$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein m is equal to 1 or 2;

wherein n is equal to 1 or 2;

wherein each of $E_1$, $E_2$, $E_3$ and $E_4$ is a substituted or unsubstituted heteroatom; and wherein $E_5$ may include OH, O, $OR_{10}$, S, $SR_{11}$, $SO_2R_{11}$, NH, $NH_2$, NOH, NHOH, $NR_{12}$, and $NHOR_{13}$.

Other embodiments relate to methods of treating WM in an animal. The methods can include, for example, administering to the animal, a therapeutically effective amount of a compound of a formula selected from Formula I, and pharmaceutically acceptable salts and pro-drug esters thereof.

Further embodiments relate to pharmaceutical compositions which include a compound of a formula selected from Formula I.

Still further embodiments relate to methods of inhibiting the growth of a cancer cell. The methods can include, for example, contacting a cancer cell with a compound of a formula selected from Formula I and pharmaceutically acceptable salts and pro-drug esters thereof.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings.

DETAILED DESCRIPTION OF THE PREFERRED EMBODIMENT

Figure 1A:
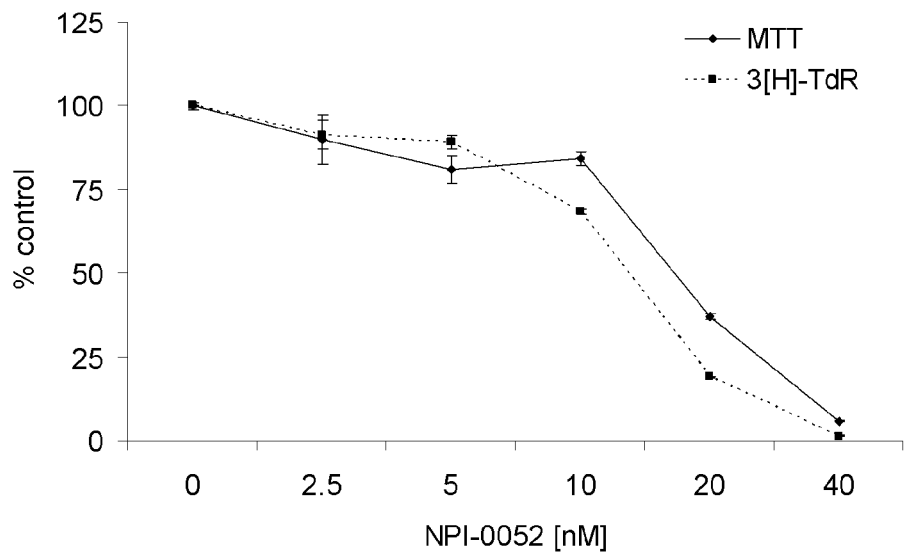
FIG. 1A is a graph showing thymidine uptake assay and cytotoxicity assessed by MTT. BCWM.1 cells were cultured with salinosporamide A (2.5-40 nM) for 48 hours.

Numerous references are cited herein. The references cited herein, including the U.S. patents cited herein, are each to be considered incorporated by reference in their entirety into this specification.

Embodiments of the invention include, but are not limited to, providing a method for the preparation of compounds, including compounds, for example, those described herein and analogs thereof, and to providing a method for producing pharmaceutically acceptable anti-cancer compositions. The methods can include the compositions in relatively high yield, wherein the compounds and/or their derivatives are among the active ingredients in these compositions. Other embodiments relate to providing novel compounds not obtainable by currently available methods. Furthermore, embodiments relate to methods of treating cancers, particularly those affecting humans. In some embodiments, one or more formulae, one or more compounds, or groups of compounds can be specifically excluded from use in any one or more of the methods of treating the conditions described herein. As one illustrative example, compounds of Formula I-16 can be excluded in some embodiments from the methods of treating cancer generally, for example, or a specific type of cancer. The methods may include, for example, the step of administering an effective amount of a member of a class of new compounds. Preferred embodiments relate to the compounds and methods of making and using such compounds disclosed herein, but not necessarily in all embodiments of the present invention, these objectives are met.

For the compounds described herein, each stereogenic carbon can be of R or S configuration. Although the specific compounds exemplified in this application can be depicted in a particular configuration, compounds having either the opposite stereochemistry at any given chiral center or mixtures thereof are also envisioned. When chiral centers are found in the derivatives of this invention, it is to be understood that the compounds encompass all possible stereoisomers.

As discussed above, WM is a biologically unique low-grade B-cell lymphoma. WM is characterized by the presence of lymphoplasmacytic cells in the bone marrow and the secretion of IgM monoclonal protein in the serum, indicating that WM cells present a high protein turnover. Protein metabolism is a tightly regulated process, and inhibition of its turnover may lead to apoptosis in malignant cells, such as with proteasome inhibitors. The major activity of proteasome inhibitors is through targeting the IL-6 and NF-κB signaling pathways. Both these pathways are critical regulators of survival and proliferation in B-cell malignancies including WM.

The multicatalytic ubiquitin-proteasome pathway is responsible for the degradation of many eukaryotic cellular proteins. This pathway also controls the activation of NF-κB by regulating the degradation of IκBα. NF-κB plays a critical role in regulating many cellular responses including immunity, inflammation, proliferation, survival, and angiogenesis. Inactive NF-κB complexes with its inhibitor, IκBα, and remains sequestered in the cytosol. A variety of stimuli trigger the phosphorylation of IκB by IκB kinase (IKK). Phosphorylated IκB is then a target for ubiquination and proteasome mediated degradation, which in turn releases NF-κB to translocate from the cytosol to the nucleus. Once in the nucleus, NF-κB stimulates transcription of numerous cytokines, chemokines, and cell adhesion molecules. NF-κB is constitutively activated in numerous hematologic malignancies, including plasma cell dyscrasias like multiple myeloma. This pathway also interacts with the PI3K/Akt pathway, a critical regulator of survival in WM cells based on our previous studies. Akt indirectly activates NF-κB through direct phosphorylation and activation of IκB kinase alpha (IKKα), thereby inducing degradation of NF-κB inhibitor alpha (IκBα) by the ubiquitin-proteasome pathway.

Bortezomib (Velcade, PS-341; Millennium Inc, Cambridge, Mass.), a proteasome inhibitor, inhibits the ubiquitin-26S proteasome pathway, which regulates the turnover of a vast number of intracellular proteins, has become an exciting target in a variety of malignancies, most notably multiple myeloma and Mantle Cell Lymphoma (MCL). The proper functioning of this system is crucial for cell cycle regulation, gene transcription, and signal transduction. Inhibition of the proteasome effectively decreases the degradation of IκBα and prevents NF-κB release and subsequent translocation to the nucleus. Based on its activity in multiple myeloma and MCL, single agent bortezomib was tested in WM in phase I trials and achieved 40-80% responses.

It has been shown that certain compounds described herein lead to inhibition of proliferation and induction of apoptosis in WM cell lines and CD19+ primary WM cells at doses achievable in vivo. In addition, the combination of certain compounds described herein and bortezomib leads to synergistic cytotoxicity on WM cell lines, IgM secreting cell lines and patient cells. These two agents lead to inhibition of nuclear translocation of p65 NF-κB, with activity on the canonical and non-canonical NF-κB pathway, and synergistic induction of caspases 3, 8 and 9 cleavage as well as PARP cleavage and induction of Smac/DIABLO.

Accordingly, some embodiments include administering a compound disclosed herein (e.g., a compound of Formula I) to a subject to treat or prevent WM. In some embodiments, the compound administered is salinosporamide A, described below. In some embodiments, a compound described herein is administered in combination with bortezomib to treat or prevent WM.

While not being bound by any particular theory, it is believed that the compounds described herein and bortezomib act synergistically through: the differential activity on the Akt pathway; and the differential activity on chymotrypsin-like, caspase-like and trypsin-like activities of the 20S proteasome. Certain compounds described herein induced cytotoxicity was completely abrogated in an Akt knockdown cell line, indicating that their major activity is mediated through the Akt pathway, while bortezomib modestly activated Akt activity. While not being bound by any particular theory, a major activity of the compounds described herein is mediated through regulation of Akt and therefore, their combination with bortezomib may overcome resistance to bortezomib in vivo.

Certain compounds described herein and bortezomib inhibit migration and adhesion of WM cells to fibronectin present in the BM microenvironment. Adhesion of WM cells to fibronectin led to NF-κB stimulation, which was abrogated by the compounds and bortezomib. In addition, the combination of these compounds and bortezomib led to inhibition of homing of WM cells in vivo in our homing model. Since IL-6 and NF-κB induction by adhesion are two major pathways regulated by the proteasome, it is believed that the compounds described herein and bortezomib overcome resistance induced by mesenchymal cells and the addition of IL-6 in a co-culture in vitro system. Finally, the combination of bortezomib and certain compounds disclosed herein does not induce cytotoxicity on hematopoietic stem cells using colony-formation assays.

The adhesion of WM cells to the bone marrow milieu induces NF-κB activation and IL-6 induces Akt activation, which were both down-regulated in the presence of certain compounds described herein either alone, and more significantly in combination with bortezomib. The combination of the two agents overcomes the protective effect of the bone marrow niches, without affecting the growth and differentiation of normal hematopoietic components. In addition, homing is a complex process that is regulated by migration and adhesion of malignant cells to their specific bone marrow niches. It is believed that the compounds described herein and bortezomib inhibit migration and adhesion of WM cells as well as their homing in vivo.

Compounds of Formula I

In some embodiments, compounds for use as described herein are represented by Formula I:

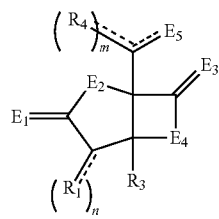

Formula I

In certain embodiments the substituent(s) $R_1$, $R_3$, and $R_4$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Further, in certain embodiments, each of $E_1$, $E_2$, $E_3$ and $E_4$ can be a substituted or unsubstituted heteroatom, for example, a heteroatom or substituted heteroatom selected from the group consisting of nitrogen, sulfur and oxygen.

In some embodiments n can be equal to 1, while in others it can be equal to 2. When n is equal to 2, the substituents can be the same or can be different. Furthermore, in some embodiments $R_3$ is not a hydrogen. m can be equal to 1 or 2, and when m is equal to 2, $R_4$ can be the same or different.

$E_5$ can be, for example, OH, O, $OR_{10}$, S, $SR_{11}$, $SO_2R_{11}$, NH, $NH_2$, NOH, NHOH, $NR_{12}$, and $NHOR_{13}$, wherein $R_{10-13}$ may separately include, for example, hydrogen, a substituted or unsubstituted of any of the following: alkyl, an aryl, a heteroaryl, and the like. Also, $R_1$ can be $CH_2CH_2X$, wherein X can be, for example, H, F, Cl, Br, and I. $R_3$ can be methyl. Furthermore, $R_4$ may include a cyclohexyl. Also, each of $E_1$, $E_3$ and $E_4$ can be O and $E_2$ can be NH. Preferably, $R_1$ can be $CH_2CH_2X$, wherein X is selected from the group consisting of H, F, Cl Br, and I; wherein $R_4$ may include a cyclohexyl; wherein $R_3$ can be methyl; and wherein each of $E_1$, $E_3$ and $E_4$ separately can be 0 and $E_2$ can be NH.

In some embodiments, $R_2$ is not cyclohex-2-enyl carbinol when one of the $R_1$ substituents is ethyl or chloroethyl and $R_3$ is methyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

For example, an exemplary compound of Formula I has the following structure I-1:

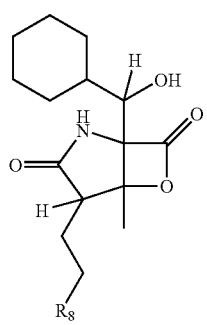

Formula I-1

$R_8$ may include, for example, hydrogen, fluorine, chlorine, bromine and iodine.

Exemplary stereochemistry can be as follows:

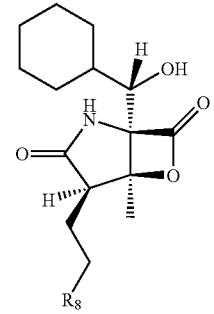

In preferred embodiments, the compound of Formula I has any of the following structures:

Formula I-2

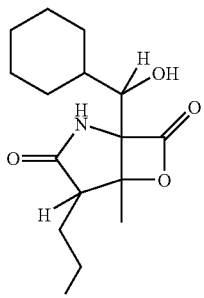

Formula I-3

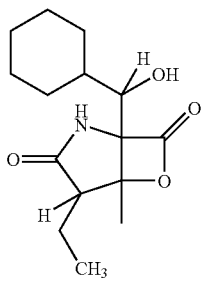

Formula I-4

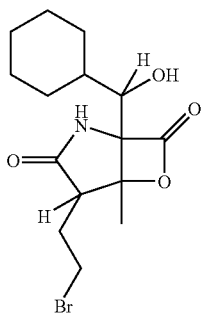

The following is exemplary stereochemistry for compounds having the structures I-2, I-3, and I-4, respectively:

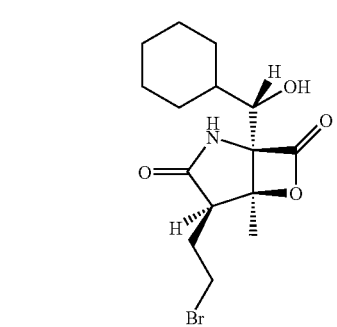

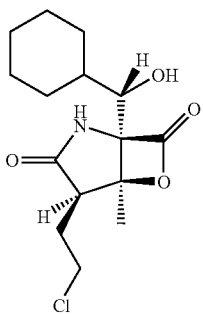

In other embodiments wherein $R_4$ may include a 7-oxa-bicyclo[4.1.0]hept-2-yl). An exemplary compound of Formula I is the following structure I-5:

Formula I-5

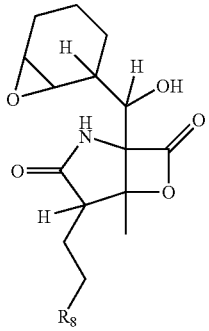

$R_8$ may include, for example, hydrogen, fluorine, chlorine, bromine and iodine.

The following are examples of compounds having the structure of Formula I-5:

FORMULAE I-5A AND I-5B

II-5A

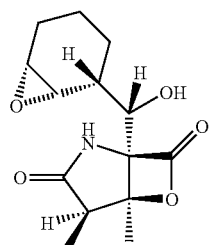

II-5B

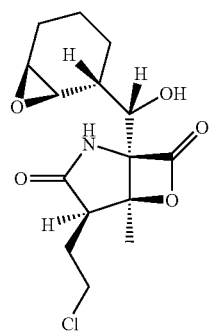

In still further embodiments, at least one $R_4$ may include a substituted or an unsubstituted branched alkyl. For example, a compound of Formula I can be the following structure I-6:

Formula I-6

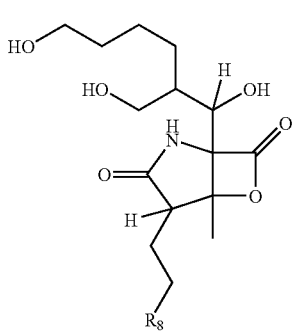

$R_8$ may include, for example, hydrogen, fluorine, chlorine, bromine and iodine.

The following is exemplary stereochemistry for a compound having the structure of Formula I-6:

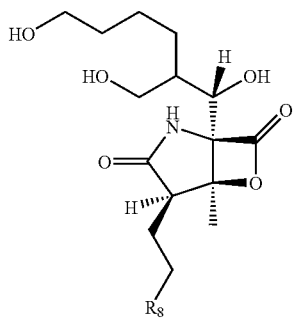

As another example, the compound of Formula I can be the following structure I-7:

Formula I-7

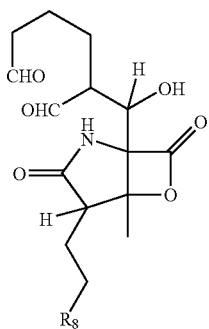

$R_8$ may include, for example, hydrogen, fluorine, chlorine, bromine and iodine.

The following is exemplary stereochemistry for a compound having the structure of Formula I-7:

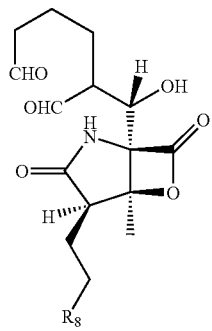

In other embodiments, at least one $R_4$ can be a cycloalkyl and $E_5$ can be an oxygen. An exemplary compound of Formula I can be the following structure I-8:

Formula I-8

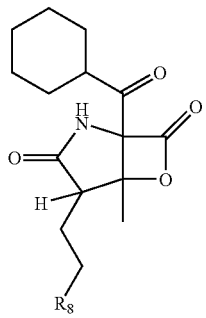

$R_8$ may include, for example, hydrogen (I-8A), fluorine (I-8B), chlorine (I-8C), bromine (I-8D) and iodine (I-8E).

The following is exemplary stereochemistry for a compound having the structure of Formula I-8:

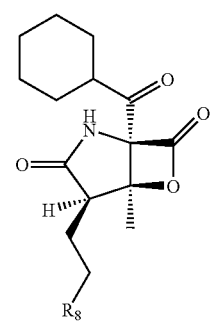

In some embodiments E5 can be an amine oxide, giving rise to an oxime. An exemplary compound of Formula I has the following structure I-9:

Formula I-9

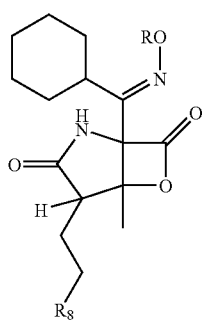

$R_8$ may include, for example, hydrogen, fluorine, chlorine, bromine and iodine; R can be hydrogen, and a substituted or unsubstituted alkyl, aryl, or heteroaryl, and the like.

The following is exemplary stereochemistry for a compound having the structure of Formula I-9:

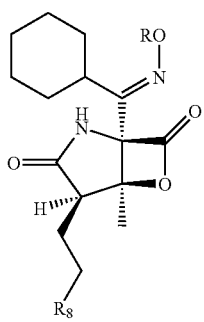

A further exemplary compound of Formula I has the following structure I-10:

Formula I-10

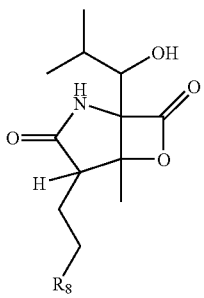

$R_8$ may include, for example, hydrogen, fluorine, chlorine, bromine and iodine.

The following is exemplary stereochemistry for a compound having the structure of Formula I-10:

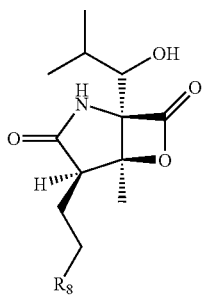

In some embodiments, $E_5$ can be $NH_2$. An exemplary compound of Formula I has the following structure I-11:

Formula I-11

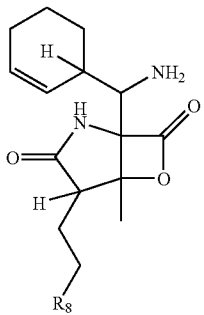

$R_8$ may include, for example, hydrogen, fluorine, chlorine, bromine and iodine.

The following is exemplary stereochemistry for a compound having the structure of Formula I-11:

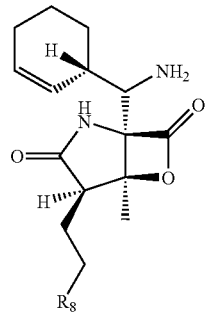

In some embodiments, at least one $R_4$ may include a cycloalkyl and $E_5$ can be $NH_2$. An exemplary compound of Formula I has the following structure I-12:

Formula I-12

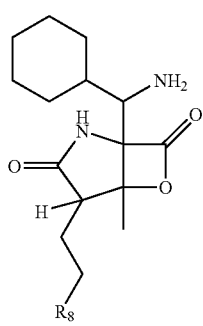

$R_8$ may include, for example, hydrogen, fluorine, chlorine, bromine and iodine.

The following is exemplary stereochemistry for a compound having the structure of Formula I-12:

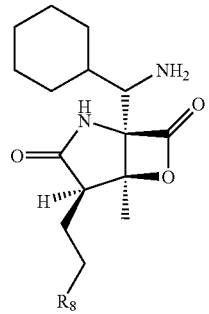

A further exemplary compound of Formula I has the following structure I-13:

Formula I-13

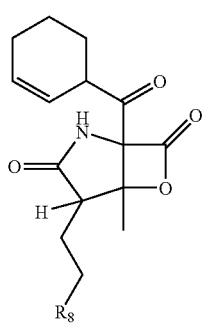

R₈ may include, for example, hydrogen (I-13A), fluorine (I-13B), chlorine (I-13C), bromine (I-13D) and iodine (I-13E).

The following is exemplary stereochemistry for a compound having the structure of Formula I-13:

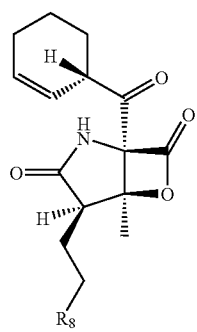

A still further exemplary compound of Formula I has the following structure I-14:

FORMULA I-14

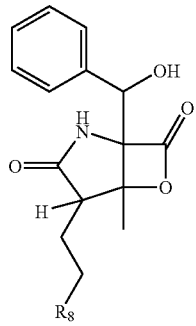

R₈ may include, for example, hydrogen, fluorine, chlorine, bromine and iodine.

The following is exemplary stereochemistry for a compound having the structure of Formula I-14:

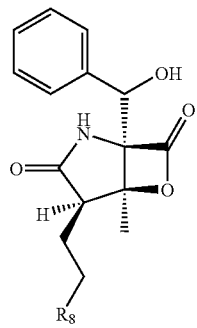

In some embodiments, the compounds of Formula I, may include as R₄ at least one cycloalkene, for example. Furthermore, in some embodiments, the compounds may include a hydroxy at E₅, for example. A further exemplary compound of Formula I has the following structure I-15:

Formula I-15

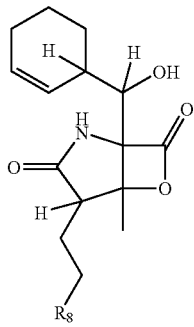

R₈ may include, for example, hydrogen, fluorine, chlorine, bromine and iodine.

Exemplary stereochemistry can be as follows:

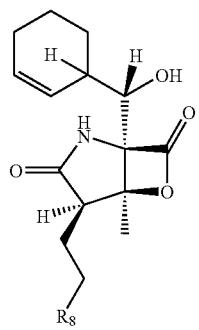

The following is exemplary stereochemistry for compounds having the structures I-16, I-17, I-18, and I-19, respectively:

I-16

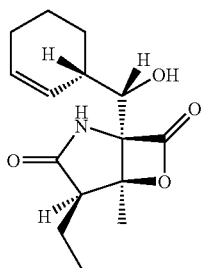

I-17

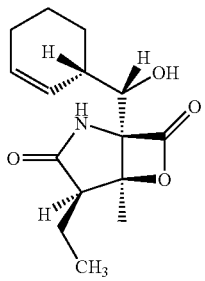

-continued

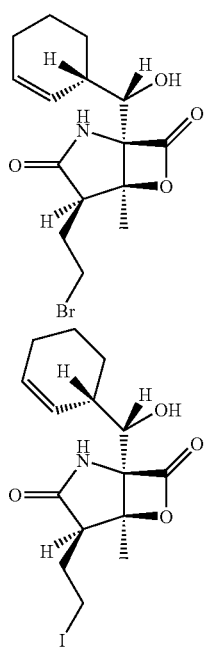

I-18

I-19

The compound of Formula I-16 is also known as salinosporamide A. The compounds of Formulae I-16, I-17, I-18 and I-19 can be obtained by fermentation, synthesis, or semi-synthesis and isolated/purified as set forth below. Furthermore, the compounds of Formulae I-16, I-17, I-18 and I-19 can be used, and are referred to, as "starting materials" to make other compounds described herein.

In some embodiments, the compounds of Formula I, may include a methyl group as $R_1$, for example. A further exemplary compound, Formula I-20, has the following structure and stereochemistry:

I-20

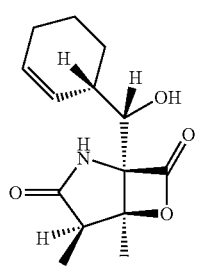

In some embodiments, the compounds of Formula I, may include hydroxyethyl as $R_1$, for example. A further exemplary compound, Formula I-21, has the following structure and stereochemistry:

I-21

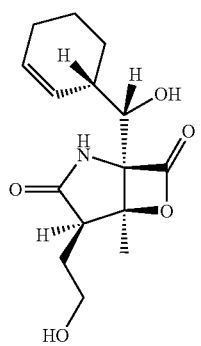

In some embodiments, the hydroxyl group of Formula I-21 can be esterified such that $R_1$ may include ethylpropionate, for example. An exemplary compound, Formula I-22, has the following structure and stereochemistry:

I-22

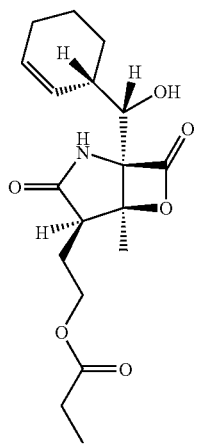

In some embodiments, the compounds of Formula I may include an ethyl group as $R_3$, for example. A further exemplary compound of Formula I has the following structure I-23:

I-23

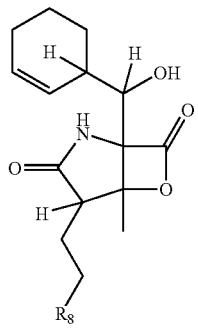

$R_8$ may include, for example, hydrogen, fluorine, chlorine, bromine and iodine. Exemplary stereochemistry can be as follows:

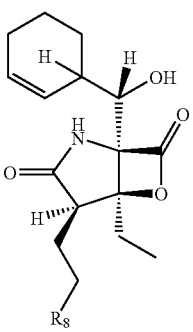

In some embodiments, the compounds of Formula I-23 may have the following structure and stereochemistry, exemplified by Formula I-24C, where $R_8$ is chlorine:

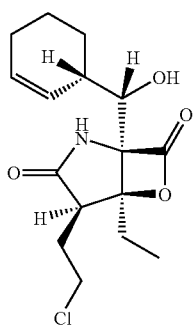
I-24C

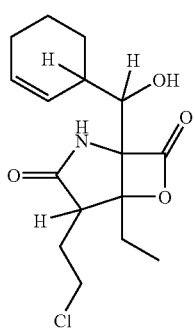
I-24C

In some embodiments, the compounds of Formula I-15 may have the following stereochemistry, exemplified by the compound of Formula I-25, where R_8 is chlorine:

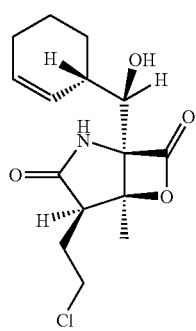
I-25

In some embodiments, the compound of Formula I-15 may have the following stereochemistry, exemplified by the compound of Formula I-26, where R_8 is chlorine:

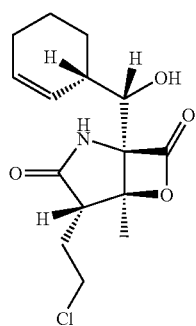
I-26

In some embodiments, the compound of Formula I may have the following structure and stereochemistry, exemplified by Formula I-27, where $R_1$ is ethyl:

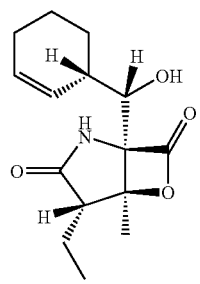
I-27

In some embodiments, the compound of Formula I may have the following structure and stereochemistry, exemplified by Formula I-28, where $R_1$ is methyl:

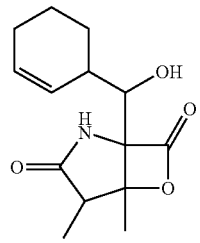
I-28

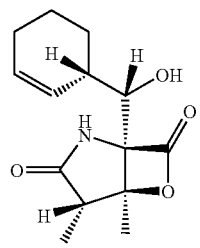
I-28

In some embodiments, the compounds of Formula I may include azidoethyl as $R_1$, for example. A further exemplary compound, Formula I-29, has the following structure and stereochemistry:

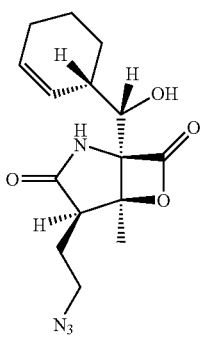
I-29

In some embodiments, the compounds of Formula I may include propyl as $R_1$, for example. A further exemplary compound, Formula I-30, has the following structure and stereochemistry:

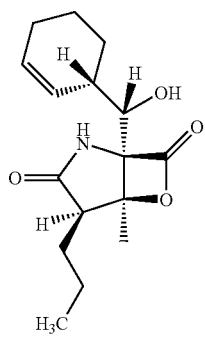

I-30

Still further exemplary compounds, Formulae I-31 and I-32, have the following structure and stereochemistry:

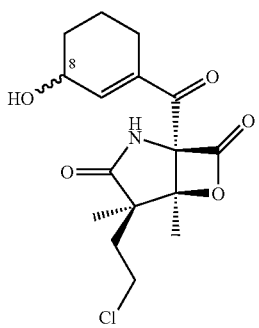

Formula I-31 and I-32

Other exemplary compounds, Formulae I-33, I-34, I-35 and I-36, have the following structure and stereochemistry:

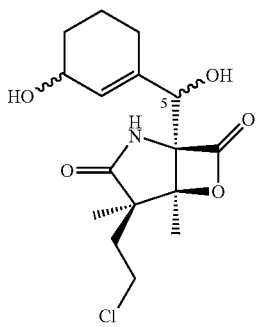

Formula I-33 and I-36

In some embodiments, the compound of Formula I may include cyanoethyl as $R_1$; for example, the compound of Formula I-37 has the following structure and stereochemistry:

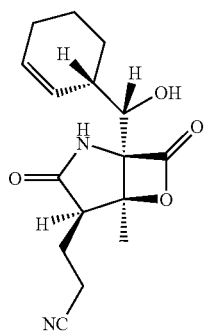

I-37

In another embodiment, the compound of Formula I may include ethylthiocyanate as $R_1$; for example, the compound of Formula I-38 has the following structure and stereochemistry:

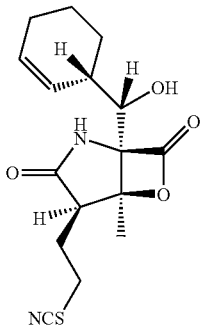

I-38

In some embodiments, the compounds of Formula I may include a thiol as $R_1$, for example. A further exemplary compound, Formula I-39, has the following structure and stereochemistry, where R=H, alkyl, aryl, or substituted alkyl or aryl:

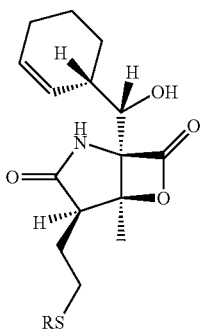

I-39

In a further exemplary compound, the sulfur of the compound of Formula I-39 can be oxidized to a sulfoxide (n=1) or sulfone (n=2), for example, as in the compound of Formula I-40:

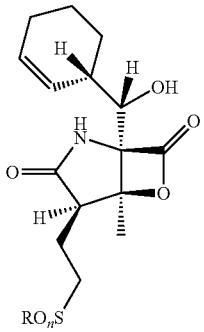

I-40

In some embodiments, the substituent $R_1$ of the compound of Formula I may include a leaving group, for example, a halogen, as in compounds I-18 or I-19, or another leaving group, such as a sulfonate ester. One example is the methane sulfonate (mesylate) of Formulae I-41A:

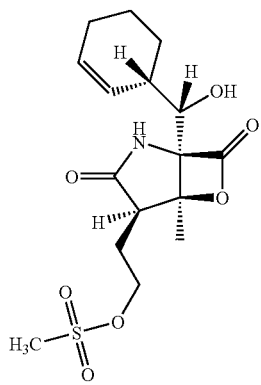

I-41A

Another embodiment is the tosylate of Formula I-41B

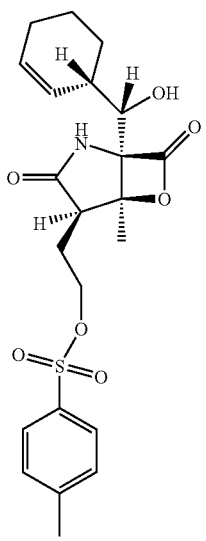

I-41B

In some embodiments, the substituent $R_1$ of the compound of Formula I may include electron acceptors. The electron acceptor can be, for example, a Lewis acid, such as a boronic acid or ester. An exemplary compound, Formula I-42, has the following structure and stereochemistry, where n=0, 1, 2, 3, 4, 5, or 6, for example, and where R=H or alkyl, for example:

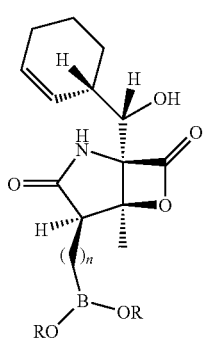

I-42

Further exemplary compounds of Formula I-42 are the compounds of Formula I-42A, where n=2 and R=H, and the compound of Formula I-42B, where n=1 and R=H:

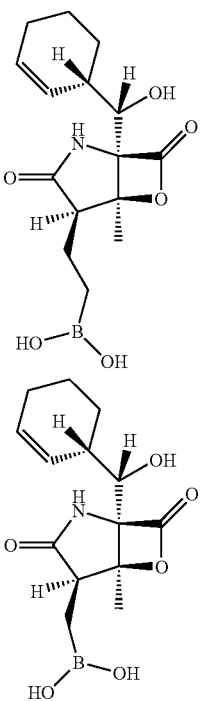

I-42A

I-42B

In some embodiments where the substituent $R_1$ of the compound of Formula I includes an electron acceptor, the electron acceptor can be, for example, a Michael acceptor. An exemplary compound, Formula I-43 has the following structure, where n=0, 1, 2, 3, 4, 5, 6, and where Z is an electron withdrawing group, for example, CHO, COR, COOR, $CONH_2$, CN, $NO_2$, SOR, $SO_2R$, etc:

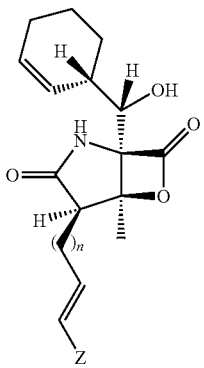

I-43

A further exemplary compound of Formula I-43 is the compound of Formula I-43A, where n=1 and Z=$CO_2CH_3$:

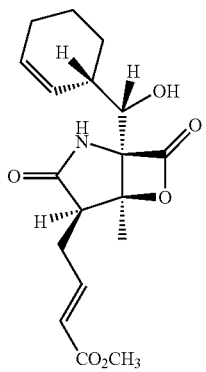

I-43A

In some embodiments, the compounds can be prodrug esters or thioesters of the compounds of Formula I. For example, the compound of Formula I-44 (a prodrug thioester of the compound of Formula I-16) has the following structure and stereochemistry:

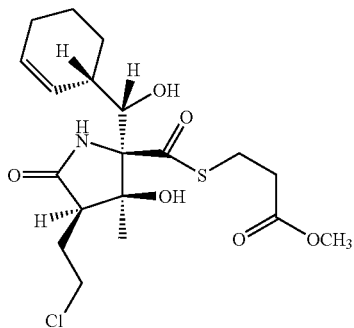

I-44

In some embodiments, the compounds of Formula I may include an alkenyl group as $R_1$, for example, ethylenyl. A further exemplary compound, Formula I-46, has the following structure and stereochemistry:

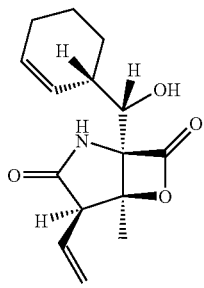

I-46

In some embodiments, the compounds can be prodrug esters or thioesters of the compounds of Formula I. For example, the compound of Formula I-47 (a prodrug thioester of the compound of Formula I-17) has the following structure and stereochemistry:

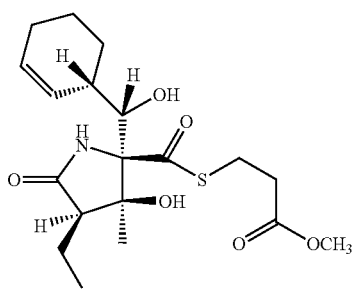

I-47

In some embodiments, the compounds can be prodrug esters or thioesters of the compounds of Formula I. For example, the compound of Formula I-48 has the following structure and stereochemistry:

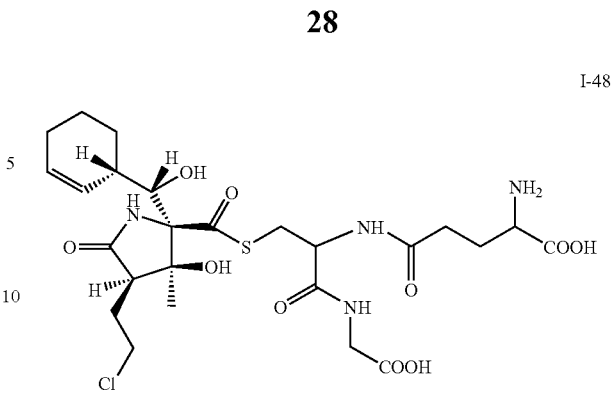

I-48

Other exemplary compound, Formula I-49 has the following structure and stereochemistry:

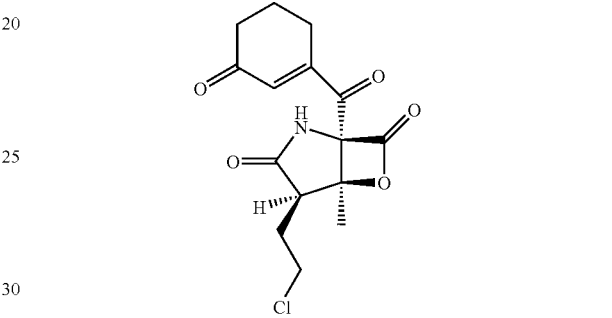

I-49

In some embodiments, the compound can be prodrug ester or thioester of the compounds of Formula I. For example, the compound of Formula I-50 (prodrug ester of the compound of Formula I-16) has the following structure and stereochemistry:

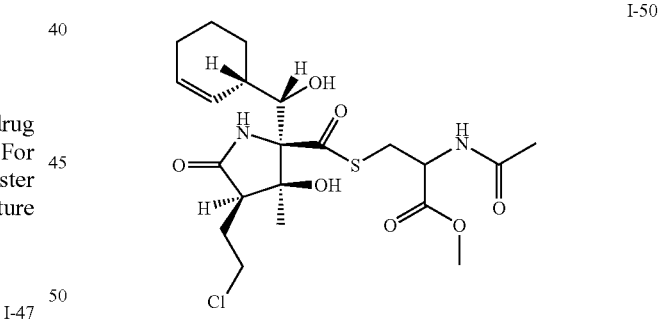

I-50

Certain embodiments also provide pharmaceutically acceptable salts and pro-drug esters or throesters of the compound of Formulae I, and provide methods of obtaining and purifying such compounds by the methods disclosed herein.

The term "pro-drug ester," especially when referring to a pro-drug ester of the compound of Formula I synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester- or thioester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)

methyl group. Other prodrugs can be prepared by preparing a corresponding thioester of the compound, for example, by reacting with an appropriate thiol, such as thiophenol, Cysteine or derivatives thereof, or propanethiol, for example. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is hereby incorporated by reference in its entirety.

The term "pharmaceutically acceptable salt," as used herein, and particularly when referring to a pharmaceutically acceptable salt of a compound, including Formulae I, and Formula I as produced and synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds synthesized by the method of this embodiment that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compound of Formulae I obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

It will be also appreciated that the phrase "compounds and compositions comprising the compound," or any like phrase, is meant to encompass compounds in any suitable form for pharmaceutical delivery, as discussed in further detail herein. For example, in certain embodiments, the compounds or compositions comprising the same may include a pharmaceutically acceptable salt of the compound.

The term "halogen atom," as used herein, means any one of the radio-stable atoms of column 7 of the Periodic Table of the Elements, i.e., fluorine, chlorine, bromine, or iodine, with bromine and chlorine being preferred.

The term "alkyl," as used herein, means any unbranched or branched, substituted or unsubstituted, saturated hydrocarbon, with $C_1$-$C_{24}$ preferred, and $C_1$-$C_6$ hydrocarbons being preferred, with methyl, ethyl, propyl, isopropyl, butyl, isobutyl, and tert-butyl, and pentyl being most preferred. Among the substituted, saturated hydrocarbons, $C_1$-$C_{24}$ are preferred, with $C_1$-$C_6$ mono- and di- and per-halogen substituted saturated hydrocarbons and amino-substituted hydrocarbons more preferred.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, thiocyanate, aryl, aryloxy, heteroaryl, heteroaryloxy, heterocyclic, heterocyclooxy, hydroxyamino, alkoxyamino, nitro, azido, boronic acid, boronic ester —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, —OSO-alkyl, —OSO-substituted alkyl, —OSO-aryl, —OSO-heteroaryl, —OSO$_2$-alkyl, —OSO$_2$-substituted alkyl, —OSO$_2$-aryl, and —OSO$_2$-heteroaryl. The other above-listed patents also provide standard definitions for the term "substituted" that are well-understood by those of skill in the art.

The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$-$C_6$ unbranched, mono-unsaturated and di-unsaturated, unsubstituted hydrocarbons being preferred, and mono-unsaturated, di-halogen substituted hydrocarbons being most preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g. oxygen, sulfur, or nitrogen atom, is in the ring along with at least one carbon atom. The term "heterocycle" or "heterocyclic" refer to any cyclic compound containing one or more heteroatoms. The substituted aryls, heterocycles and heteroaryls can be substituted with any substituent, including those described above and those known in the art.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring. The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, sec-butoxycarbonyl group, tert-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound may comprise at least 0.5%, 1%, 5%, 10%, or 20%, and most preferably at least 50% or 75% of the mass, by weight, of a given sample.

The terms "derivative," "variant," or other similar term refers to a compound that is an analog of the other compound.

Certain of the compounds of Formula I can be obtained and purified or can be obtained via semi-synthesis from purified compounds as set forth herein. Generally, without being limited thereto, the compounds of Formula I-15, preferably, Formulae I-16, I-17, I-18 and I-19, can be obtained synthetically or by fermentation. Exemplary fermentation procedures are provided below. Further, the compounds of Formula I-15, preferably, Formulae I-16, I-17, I-18 and I-19 can be used as starting compounds in order to obtain/synthesize various of the other compounds described herein. Exemplary non-limiting syntheses are provided herein.

Formula I-16

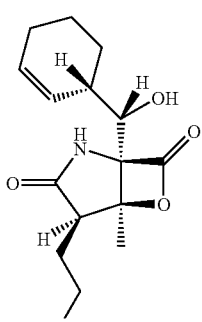

Formula I-17

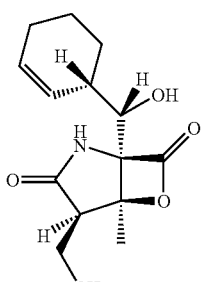

Formula I-18

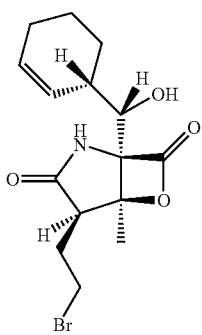

Formula I-19

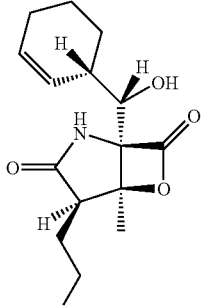

Formula I-16 may be produced through a high-yield saline fermentation (~350-400 mg/L) and modifications of the conditions have yielded new analogs in the fermentation extracts. Additional analogs can be generated through directed biosynthesis. Directed biosynthesis is the modification of a natural product by adding biosynthetic precursor analogs to the fermentation of producing microorganisms (Lam, et al., *J Antibiot* (Tokyo) 44:934 (1991), Lam, et al., *J Antibiot* (Tokyo) 54:1 (2001); which is hereby incorporated by reference in its entirety).

Exposing the producing culture to analogs of acetic acid, phenylalanine, valine, butyric acid, shikimic acid, and halogens, preferably, other than chlorine, can lead to the formation of new analogs. The new analogs produced can be easily detected in crude extracts by HPLC and LC-MS. For example, after manipulating the medium with different concentrations of sodium bromide, a bromo-analog, Formula I-18, was successfully produced in shake-flask culture at a titer of 14 mg/L.

A second approach to generate analogs is through biotransformation. Biotransformation reactions are chemical reactions catalyzed by enzymes or whole cells containing these enzymes. Zaks, A., *Curr Opin Chem Biol* 5:130 (2001). Microbial natural products are ideal substrates for biotransformation reactions as they are synthesized by a series of enzymatic reactions inside microbial cells. Riva, S., *Curr Opin Chem Biol* 5:106 (2001).

Given the structure of the described compounds, including those of Formula I-15, for example, the possible biosynthetic origins are acetyl-CoA, ethylmalonyl-CoA, phenylalanine and chlorine. Ethylmalonyl-CoA is derived from butyryl-CoA, which can be derived either from valine or crotonyl-CoA. Liu, et al., *Metab Eng* 3:40 (2001). Phenylalanine is derived from shikimic acid.

Alternatively, compositions such as Formula I-16 and its analogs may be produced synthetically, e.g., such as described in U.S. application Ser. No. 11/697,689, which is incorporated by reference in its entirety.

Production of Compounds of Formulae I-16, I-17, I-18, I-20, I-24C, I-26, I-27 and I-28

The production of compounds of Formulae I-16, I-17, I-18, I-20, I-24C, I-26, I-27 and I-28 can be carried out by cultivating strain CNB476 and strain NPS21184, a natural variant of strain CNB476, in a suitable nutrient medium under conditions described herein, preferably under submerged aerobic conditions, until a substantial amount of compounds are detected in the fermentation; harvesting by extracting the active components from the fermentation broth with a suitable solvent; concentrating the solvent containing the desired components; then subjecting the concentrated material to chromatographic separation to isolate the compounds from other metabolites also present in the cultivation medium.

The culture (CNB476) was deposited on Jun. 20, 2003 with the American Type Culture Collection (ATCC) in Rockville, Md. and assigned the ATCC patent deposition number PTA-5275. Strain NPS21184, a natural variant of strain CNB476, was derived from strain CNB476 as a single colony isolate. Strain NPS21184 has been deposited to ATCC on Apr. 27, 2005. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce the starting compounds of Formulae I-16, I-17, and I-18.

Fermentation of Strain CNB476 and Strain NPS21184

Production of compounds can be achieved at temperature conducive to satisfactory growth of the producing organism, e.g. from 16 degree C. to 40 degree C., but it is preferable to conduct the fermentation at 22 degree C. to 32 degree C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 400 rpm, preferably at 150 rpm to 250 rpm, for example. The production of the compounds can also be achieved by cultivating the production strain in a bioreactor, such as a fermentor system that is suitable for the growth of the production strain.

Growth of the microorganisms can be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources can be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like. Pharmaceutical Compositions In one embodiment, the compounds disclosed herein are used in pharmaceutical compositions. The compounds preferably can be produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents can be provided in the pharmaceutical composition. For example, sodium benzoate, ascorbic acid and esters of p-hydroxybenzoic acid can be added as preservatives. In addition, antioxidants and suspending agents can be used.

The compositions can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties.

Further disclosed herein are various pharmaceutical compositions well known in the pharmaceutical art for uses that include topical, intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2): 101-3 (1996)); ophthalmic ointments; ophthalmic suspensions, such as microparticulates, drug-containing small polymeric particles that are suspended in a liquid carrier medium (Joshi, A. 1994 *J Ocul Pharmacol* 10:29-45), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, 18$^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include anti-microbial preservatives and appropriate drug stabilizers. Pharmaceutical formulations for intraauricular delivery include suspensions and ointments for topical application in the ear. Common solvents for such aural formulations include glycerin and water.

When used as an anti-cancer compound, for example, the compounds of Formulae I or compositions including Formulae I can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the anti-cancer agent can be mixed with additional substances to enhance their effectiveness.

Methods of Administration

In an alternative embodiment, the disclosed chemical compounds and the disclosed pharmaceutical compositions are administered by a particular method as an anti-microbial. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the compositions that include the described compounds required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages can be between about 10 microgram/kg and 100 mg/kg body weight, preferably between about 100 microgram/kg and 10 mg/kg body weight. Alternatively dosages can be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above can be used in veterinary medicine.

Depending on the specific conditions being treated, such agents can be formulated and administered systemically or locally. A variety of techniques for formulation and administration can be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, can be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly can be administered using techniques well known to those of ordinary skill in the art. For example, such agents can be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration can be in the form of tablets, dragees, capsules, or solutions. The pharmaceutical compositions can be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods. The efficacy of a particular compound can be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction, and infectious diseases. Similarly, acceptable animal models can be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-cancer agent, the compounds disclosed herein can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, intradermally, or the like. Controlled release formulations, depot formulations, and infusion pump delivery are similarly contemplated.

The compositions disclosed herein in pharmaceutical compositions may also comprise a pharmaceutically acceptable carrier. Such compositions can be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions can be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the embodiment, as described above, can be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions can be formulated and administered either systemically or locally. A variety of techniques for formulation and administration can be found in Remington's Pharmaceutical Sciences, 18th ed., Mack Publishing Co., Easton, Pa. (1990).

To formulate the compounds of Formulae I as an anti-cancer agent, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing preferred ingredients, sweeteners, fragrances, colorants, preservatives and the like can be added to the administered formulation of the compound produced by the method of the embodiment, particularly when the compound is to be administered orally.

The compounds and compositions can be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound produced by the method of the embodiment may preferably be administered in the stated amounts continuously by, for example, an intravenous drip. Thus, for the example of a patient weighing 70 kilograms, the preferred daily dose of the active ingredient would be about 0.07 mg/day to about 700 gm/day, and more preferable, 7 mg/day to about 7 grams/day. Nonetheless, as will be understood by those of skill in the art, in certain situations it can be necessary to administer the anti-cancer compound of the embodiment in amounts that excess, or even far exceed, the above-stated, preferred dosage range to effectively and aggressively treat particularly advanced cancers or infections.

In the case of using the cancer produced by methods of the embodiment as a biochemical test reagent, the compound produced by methods of the embodiment inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the embodiment for use as an anticancer compound is generally in the range of about 1 to about 100 μg/ml, the most appropriate use amount varies depending on the type of cultured cell system and the purpose of use, as will be appreciated by persons of ordinary skill in the art. Also, in certain applications it can be necessary or preferred to persons of ordinary skill in the art to use an amount outside the foregoing range.

In one embodiment, the method of using a compound as an anti-cancer involves administering an effective amount of any of the compounds of Formulae I or compositions of those compounds. In a preferred embodiment, the method involves administering the compound represented by Formula I, to a patient in need of an anti-cancer agent, until the need is effectively reduced or more preferably removed.

As will be understood by one of skill in the art, "need" is not an absolute term and merely implies that the patient can benefit from the treatment of the anti-cancer agent in use. By "patient" what is meant is an organism that can benefit by the use of an anti-cancer agent. For example, any organism with cancer, such as, WM. In one embodiment, the patient's health may not require that an anti-cancer agent be administered, however, the patient may still obtain some benefit by the reduction of the level of cancer cells present in the patient, and thus be in need. In one embodiment, the anti-anti-cancer agent is effective against one type of cancer, but not against other types; thus, allowing a high degree of selectivity in the treatment of the patient. In choosing such an anti-cancer agent, the methods and results disclosed in the Examples can be useful. In still further embodiments, the anti-cancer agent is effective against a broad spectrum of cancers or all cancers. Examples of cancers, against which the compounds can be effective include WM, a colorectal carcinoma, a prostate carcinoma, a breast adenocarcinoma, a non-small cell lung carcinoma, an ovarian carcinoma, multiple myelomas, a melanoma, and the like.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

"Anti-cancer agent" refers to a compound or composition including the compound that reduces the likelihood of survival of a cancer cell. In one embodiment, the likelihood of survival is determined as a function of an individual cancer cell; thus, the anti-cancer agent will increase the chance that an individual cancer cell will die. In one embodiment, the likelihood of survival is determined as a function of a population of cancer cells; thus, the anti-cancer agent will increase the chances that there will be a decrease in the population of cancer cells. In one embodiment, anti-cancer agent means chemotherapeutic agent or other similar term.

A "chemotherapeutic agent" is a chemical compound useful in the treatment of a neoplastic disease, such as cancer. Examples of chemotherapeutic agents include alkylating agents, such as a nitrogen mustard, an ethyleneimine and a methylmelamine, an alkyl sulfonate, a nitrosourea, and a triazene, folic acid antagonists, anti-metabolites of nucleic acid metabolism, antibiotics, pyrimidine analogs, 5-fluorouracil, cisplatin, purine nucleosides, amines, amino acids, triazol nucleosides, corticosteroids, a natural product such as a vinca alkaloid, an epipodophyllotoxin, an antibiotic, an enzyme, a taxane, and a biological response modifier or antibodies to biological response modifiers or other agents; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gouadotropin-releasing hormone analog. Specific examples include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins, Melphalan, and other related nitrogen mustards. Also included in this definition are hormonal agents that act to regulate or inhibit hormone action on tumors, such as tamoxifen and onapristone.

The anti-cancer agent may act directly upon a cancer cell to kill the cell, induce death of the cell, to prevent division of the cell, and the like. Alternatively, the anti-cancer agent may indirectly act upon the cancer cell by limiting nutrient or blood supply to the cell, for example. Such anti-cancer agents are capable of destroying or suppressing the growth or reproduction of cancer cells, such as a colorectal carcinoma, a prostate carcinoma, a breast adenocarcinoma, a non-small cell lung carcinoma, an ovarian carcinoma, multiple myelomas, a melanoma, and the like.

In one embodiment, a described compound, preferably a compound having the Formulae I, including those as described herein, is considered an effective anti-cancer agent if the compound can influence 10% of the cancer cells, for example. In a more preferred embodiment, the compound is effective if it can influence 10 to 50% of the cancer cells. In an even more preferred embodiment, the compound is effective if it can influence 50-80% of the cancer cells. In an even more preferred embodiment, the compound is effective if it can influence 80-95% of the cancer cells. In an even more preferred embodiment, the compound is effective if it can influence 95-99% of the cancer cells. "Influence" is defined by the mechanism of action for each compound. For example, if a compound prevents the division of cancer cells, then influence is a measure of prevention of cancer cell division. Not all mechanisms of action need be at the same percentage of effectiveness. In an alternative embodiment, a low percentage effectiveness can be desirable if the lower degree of effectiveness is offset by other factors, such as the specificity of the compound, for example. Thus a compound that is only 10% effective, for example, but displays little in the way of harmful side-effects to the host, or non-harmful microbes or cells, can still be considered effective.

In one embodiment, the compounds described herein are administered simply to remove cancer cells and need not be administered to a patient. For example, the compounds can be administered ex vivo to a cell sample, such as a bone marrow or stem cell transplant to ensure that only non-cancerous cells are introduced into the recipient. After the compounds are administered they may optionally be removed. Whether or not this is an option will depend upon the relative needs of the situation and the risks associated with the compound, which in part can be determined as described in the Examples below.

The following non-limiting examples are meant to describe the preferred embodiments of the methods. Variations in the details of the particular methods employed and in the precise chemical compositions obtained will undoubtedly be appreciated by those of skill in the art.

EXAMPLES

Example 1

Fermentation of Compound of Formulae I-16, I-17, I-20, I-24C, I-26 and I-28 Using Strain CNB476

Strain CNB476 was grown in a 500-ml flask containing 100 ml of vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml each of the first seed culture was inoculated into three 500-ml flasks containing of 100 ml of the vegetative medium. The second seed cultures were incubated at 28 degree C. and 250 rpm on a rotary shaker for 2 days. Five ml each of the second seed culture was inoculated into thirty-five 500-ml flasks containing of 100 ml of the vegetative medium. The third seed cultures were incubated at 28 degree and 250 rpm on a rotary shaker for 2 days. Five ml each of the third seed culture was inoculated into four hundred 500-ml flasks containing 100 ml of the Production Medium A consisting of the following per liter of deionized water: starch, 10 g; yeast extract, 4 g; Hy-Soy, 4 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on roatry shakers for 1 day. Approximately 2 to 3 grams of sterile Amberlite XAD-7 resin were added to the production cultures. The production cultures were further incubated at 28 degree C. and 250 rpm on rotary shakers for 5 days and achieved a titer of Compound I-16 of about 200 mg/L. The culture broth was filtered through cheese cloth to recover the Amberlite XAD-7 resin. The resin was extracted with 2 times 6 liters ethyl acetate followed by 1 time 1.5 liters ethyl acetate. The combined extracts were dried in vacuo. The dried extract, containing 3.8 grams the compound of Formula I-16 and lesser quantities of compounds of formulae I-20 and I-24C, was then processed for the recovery of the compounds of Formula I-16, I-20, I-24C, I-26 and I-28.

Example 2

Fermentation of Compounds I-16, I-17, I-20, I-24C, I-26 and I-28 Using Strain NPS21184

Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Five ml each of the second seed culture was inoculated into 500-ml flask containing of 100 ml of the vegetative medium. The third seed cultures were incubated at 28 degree and 250 rpm on a rotary shaker for 2 days. Five ml each of the third seed culture was inoculated into 500-ml flask containing 100 ml of the Production Medium B consisting of the following per liter of deionized water: starch, 20 g; yeast extract, 4 g; Hy-Soy, 8 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on rotary shakers for 1 day. Approximately 2 to 3 grams of sterile Amberlite XAD-7 resin were added to the production culture. The production culture was further incubated at 28 degree C. and 250 rpm on rotary shaker for 4 days and achieved a titer of 350-400 mg/L for Compound I-16.

Alternatively, the production of the compounds can be achieved in a 42 L fermentor system using strain NPS21184. Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Twenty ml each of the second seed culture was inoculated into 2.8 L Fernbach flask containing of 400 ml of the vegetative medium. The third seed cultures were incubated at 28 degree and 250 rpm on a rotary shaker for 2 days. 1.2 L of the third seed culture was inoculated into a 42 L fermentor containing 26 L of Production Medium A. Production Medium B and Production Medium C, with the following composition, can also be used. Production Medium C consisting of the following per liter of deionized water: starch, 15 g; yeast extract 6 g; Hy-Soy, 6 g; ferric sulfate, 40 mg; potassium bromide, 100 mg; calcium carbonate, 1 g; and synthetic sea salt (Instant Ocean, Aquarium Systems), 30 g. The fermentor cultures were operated at the following parameters: temperature, 28 degree C.; agitation, 200 rpm; aeration, 13 L/min and back pressure, 4.5 psi. At 36 to 44 hours of the production cycle, approximately 600 grams of sterile Amberlite XAD-7 resin were added to the fermentor culture. The production culture was further incubated at the above operating parameters until day 4 of the production cycle. The aeration rate was lowered to 8 L/min. At day 5 of the production cycle, the fermentor culture achieved a titer of about 300 mg/L for Compound I-16. The culture broth was filtered through cheese cloth to recover the Amberlite XAD-7 resin. The resin was extracted with 2 times 4.5 L liters ethyl acetate followed by 1 time 1.5 liters ethyl acetate. The combined extracts were dried in vacuo. The dried extract was then processed for the recovery of the Compounds of Formulae I-16, I-17, I-20, I-24C, I-26 and I-28.

Example 3

Purification of Compound of Formulae I-16, I-20, I-24C, I-26 and I-28

The pure compounds of Formulae I-16, I-20 I-24C, I-26 and I-28 were obtained by flash chromatography followed by HPLC. Eight grams crude extract containing 3.8 grams of the compound of Formula I-16 and lesser quantities of I-20, I-24C, I-26 and I-28 was processed by flash chromatography using Biotage Flash40i system and Flash 40M cartridge (KP-Sil Silica, 32-63 μm, 90 grams). The flash chromatography was developed by the following step gradient:
1. Hexane (1 L)
2. 10% Ethyl acetate in hexane (1 L)
3. 20% Ethyl acetate in hexane, first elution (1 L)
4. 20% Ethyl acetate in hexane, second elution (1 L)
5. 20% Ethyl acetate in hexane, third elution (1 L)
6. 25% Ethyl acetate in hexane (1 L)
7. 50% Ethyl acetate in hexane (1 L)
8. Ethyl acetate (1 L)

Fractions containing the compound of Formula I-16 in greater or equal to 70% UV purity by HPLC were pooled and subject to HPLC purification, as described below, to obtain I-16, along with I-20 and I-24C, each as pure compounds

| Column | Phenomenex Luna 10u Silica |
|---|---|
| Dimensions | 25 cm × 21.2 mm ID |
| Flow rate | 25 ml/min |
| Detection | ELSD |
| Solvent | Gradient of 24% EtOAc/hexane for 19 min, 24% EtOAc/hexane to 100% EtOAc in 1 min, then 100% EtOAc for 4 min |

The fraction enriched in compound of Formula I-16 (described above; ~70% pure with respect to I-16) was dissolved in acetone (60 mg/ml). Aliquots (950 ul) of this solution were injected onto a normal-phase HPLC column using the conditions described above. Compound I-16 typically eluted after 14 minutes and compounds I-24C and I-26 co-eluted as a single peak at 11 min. When parent samples containing compounds I-17, I-20 and I-28 were processed, compound I-17 eluted at 22 minutes, while I-20 and I-28 co-eluted at 23 minutes during the 100% ethyl acetate wash. Fractions containing compound I-16 and minor analogs were pooled based on composition of compounds present, and evaporated under reduced pressure on a rotary evaporator. This process yielded pure Compound A, as well as separate fractions containing minor compounds I-20, I-24C, I-26 and I-28, which were further purified as described below.

Sample containing I-24C and I-26 generated from the process described above were further separated using reversed-phase preparative HPLC as follows. The sample containing I-24C (70 mg) was dissolved in acetonitrile at a concentration of 10 mg/ml, and 500 μl was loaded on an HPLC column of dimensions 21 mm i.d. by 15 cm length containing Eclipse XDB-C18 support. The solvent gradient increased linearly from 15% acetonitrile/85% water to 100% acetonitrile over 23 minutes at a flow rate of 14.5 ml/min. The solvent composition was held at 100% acetonitrile for 3 minutes before returning to the starting solvent mixture. Compound I-26 eluted at 17.5 minutes while compound I-24C eluted at 19 minutes under these conditions.

Crystalline I-26 was obtained using a vapor diffusion method. Compound I-26 (15 mg) was dissolved in 100 μl of acetone in a 1.5 ml v-bottom HPLC vial. This vial was then placed inside a larger sealed vessel containing 1 ml of pentane. Crystals suitable for X-ray crystallography experiments were observed along the sides and bottom of the inner vial after 48 hours of incubation at 4° C. Crystallography data was collected on a Bruker SMART APEX CCD X-ray diffractometer (F(000)=2656, $MO_{K\alpha}$ radiation, $\lambda$=0.71073 Å, $\mu$=0.264 $mm^{-1}$, T=100K) at the UCSD Crystallography Lab and the refinement method used was full-matrix least-squares on $F^2$. Crystal data NPI-2065: $C_{15}H_{20}ClNO_4$, MW=313.77, tetragonal, space group $P4(1)2(1)_2$, a=b=11.4901(3) Å, c=46.444(2) Å, $\alpha$=$\beta$=$\gamma$=90°, vol=6131.6(3) $Å^3$, Z=16, $\rho_{calcd}$=1.360 g $cm^{-3}$, crystal size, 0.30×0.15×0.07 $mm^3$, $\theta$ range, 1.75-26.00°, 35367 reflections collected, 6025 independent reflections ($R_{int}$=0.0480), final R indices (I>2σ(I)): $R_1$=0.0369, $wR_2$=0.0794, GOF=1.060.

In order to separate I-28 from I-20, a reverse-phase isocratic method was employed. Sample (69.2 mg) containing both compounds was dissolved in acetonitrile to a concentration of 10 mg/ml, and 500 μl was loaded on a reverse-phase HPLC column (ACE 5 C18-HL, 15 cm×21 mm ID) per injection. An isocratic solvent system of 27% acetonitrile/63% water at flow rate of 14.5 ml/min was used to separate compounds I-28 and I-20, which eluted after 14 and 16 minutes, respectively. Fractions containing compounds of interest were immediately evaporated under reduced pressure at room temperature on a rotary evaporator. Samples were then loaded onto a small column of silica and eluted with 10 ml of 70% hexane/30% acetone to remove additional impurities.

Samples generated from the preparative normal-phase HPLC method described above that contained I-20, but which were free of I-28 could also be triturated with 100% EtOAc to remove minor lipophilic impurities.

Compound of Formula I-16: UV (Acetonitrile/$H_2O$) $\lambda_{max}$ 225(sh) nm. Low Res. Mass: m/z 314 (M+H), 336 (M+Na).

Compound of Formula I-20: UV (Acetonitrile/$H_2O$) $\lambda_{max}$ 225(sh) nm. Low Res. Mass: m/z 266 (M+H); HRMS (ESI), m/z 266.1396 (M+H), $\Delta_{calc}$=1.2 ppm.

Compound of Formula I-24C: UV (Acetonitrile/$H_2O$) $\lambda_{max}$ 225(sh) nm. Low Res. Mass: m/z 328 (M+H), 350 (M+Na); HRMS (ESI), m/z 328.1309 (M+H), $\Delta_{calc}$=-2.0 ppm, $C_{16}H_{23}NO_4Cl$.

Compound of Formula I-26: UV (Acetonitrile/$H_2O$) $\lambda_{max}$ 225(sh) nm; HRMS (ESI), m/z 314.1158 (M+H), $\Delta_{calc}$=-0.4 ppm, $C_{15}H_{21}NO_4Cl$.

Compound of Formula I-28: UV (Acetonitrile/H$_2$O) $\lambda_{max}$ 225(sh) nm; HRMS (ESI), m/z 266.1388 (M+H), $\Delta_{calc}$=−1.8 ppm, C$_{14}$H$_{20}$NO$_4$.

Example 4

Fermentation of Compounds of Formulae I-17, I-18, and I-27

Strain CNB476 was grown in a 500-ml flask containing 100 ml of the first vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into a 500-ml flask containing 100 ml of the second vegetative medium consisting of the following per liter of deionized water: starch, 10 g; yeast extract, 4 g; peptone, 2 g; ferric sulfate, 40 mg; potassium bromide, 100 mg; calcium carbonate, 1 g; and sodium bromide, 30 g. The second seed cultures were incubated at 28° C. for 7 days on a rotary shaker operating at 250 rpm. Approximately 2 to 3 gram of sterile Amberlite XAD-7 resin were added to the second seed culture. The second seed culture was further incubated at 28° C. for 2 days on a rotary shaker operating at 250 rpm. Five ml of the second seed culture was inoculated into a 500-ml flask containing 100 ml of the second vegetative medium. The third seed culture was incubated at 28° C. for 1 day on a rotary shaker operating at 250 rpm. Approximately 2 to 3 gram of sterile Amberlite XAD-7 resin were added to the third seed culture. The third seed culture was further incubated at 28° C. for 2 days on a rotary shaker operating at 250 rpm. Five ml of the third culture was inoculated into a 500-ml flask containing 100 ml of the second vegetative medium. The fourth seed culture was incubated at 28° C. for 1 day on a rotary shaker operating at 250 rpm. Approximately 2 to 3 gram of sterile Amberlite XAD-7 resin were added to the fourth seed culture. The fourth seed culture was further incubated at 28° C. for 1 day on a rotary shaker operating at 250 rpm. Five ml each of the fourth seed culture was inoculated into ten 500-ml flasks containing 100 ml of the second vegetative medium. The fifth seed cultures were incubated at 28° C. for 1 day on a rotary shaker operating at 250 rpm. Approximately 2 to 3 grams of sterile Amberlite XAD-7 resin were added to the fifth seed cultures. The fifth seed cultures were further incubated at 28° C. for 3 days on a rotary shaker operating at 250 rpm. Four ml each of the fifth seed culture was inoculated into one hundred and fifty 500-ml flasks containing 100 ml of the production medium having the same composition as the second vegetative medium. Approximately 2 to 3 grams of sterile Amberlite XAD-7 resin were also added to the production culture. The production cultures were incubated at 28° C. for 6 day on a rotary shaker operating at 250 rpm. The culture broth was filtered through cheese cloth to recover the Amberlite XAD-7 resin. The resin was extracted with 2 times 3 liters ethyl acetate followed by 1 time 1 liter ethyl acetate. The combined extracts were dried in vacuo. The dried extract, containing 0.42 g of the compound Formula I-17 and 0.16 gram the compound of Formula I-18, was then processed for the recovery of the compounds.

Example 5

Purification of Compounds of Formula I-17, I-18 and I-27

The pure compounds of Formula I-17 and I-18 were obtained by reversed-phase HPLC as described below:

| Column | ACE 5 C18-HL |
|---|---|
| Dimensions | 15 cm × 21 mm ID |
| Flow rate | 14.5 ml/min |
| Detection | 214 nm |
| Solvent | Gradient of 35% Acetonitrile/65% H$_2$O to 90% Acetonitrile/10% H$_2$O over 15 min |

Crude extract (100 mg) was dissolved in 15 ml of acetonitrile. Aliquots (900 ul) of this solution were injected onto a reversed-phase HPLC column using the conditions described above. Compounds of Formulae I-17 and I-18 eluted at 7.5 and 9 minutes, respectively. Fractions containing the pure compounds were first concentrated using nitrogen to remove organic solvent. The remaining solution was then frozen and lyophilized to dryness.

An alternative purification method for Compound I-17 and I-18 was developed for larger scale purification and involved fractionation of the crude extract on a normal phase VLC column. Under these conditions, sufficient amounts of several minor metabolites were identified, including compound I-27. The crude extract (2.4 g) was dissolved in acetone (10 ml) and this solution adsorbed onto silica gel (10 cc) by drying in vacuo. The adsorbed crude extract was loaded on a normal phase silica VLC column (250 cc silica gel, column dimensions 2.5 cm diameter by 15 cm length) and washed with a step gradient of hexane/EtOAc, increasing in the percentage of hexane in steps of 5% (100 ml solvent per step). The majority of compound I-16 eluted in the 60% hexane/40% EtOAc wash while the majority of compound I-17 eluted in the 50% hexane/50% ethyl acetate wash. Final separation of the compounds was achieved using C18 HPLC chromatography (ACE 5µ C18-HL, 150 mm×21 mm ID) using an isocratic solvent system consisting of 35% ACN/65% H2O. Under these conditions, compound I-27 eluted at 11 minutes, compound I-17 eluted at 12.00 minutes, traces of compound A eluted at 23.5 minutes, and compound I-18 eluted at 25.5 minutes. The resulting samples were dried in vacuo using no heat to remove the aqueous solvent mixture. The spectroscopic data for these samples of compound I-16 and compound I-18 were found to be identical with those of samples prepared from earlier purification methods. The sample of compound I-18 was found to contain 8% of the lactone hydrolysis product and was further purified by washing through a normal phase silica plug (1 cm diameter by 2 cm height) and eluting using a solvent mixture of 20% EtOAc/80% Hexanes (25 ml). The resulting sample was found to contain pure compound I-18.

The fractions containing compound I-27 described above were further purified using normal phase semipreparative HPLC (Phenomenex Luna Si 10µ, 100 Å; 250×10 mm id) using a solvent gradient increasing from 100% hexane to 100% EtOAc over 20 minutes with a flowrate of 4 ml/min. Compound I-27 eluted as a pure compound after 11.5 minutes (0.8 mg, 0.03% isolated yield from dried extract weight).

Compound of Formula I-17: UV (Acetonitrile/H$_2$O) $\lambda_{max}$ 225(sh) nm. High Res. Mass (APCI): m/z 280.156 (M+H), $\Delta_{calc}$=2.2 ppm, C$_{15}$H$_{22}$NO$_4$.

Compound of Formula I-18: UV (Acetonitrile/H$_2$O) $\lambda_{max}$ 225(sh) nm. High Res. Mass (APCI): m/z 358.065 (M+H), $\Delta_{calc}$=−1.9 ppm, C$_{15}$H$_{21}$NO$_4$Br.

Compound I-27: UV (Acetonitrile/H$_2$O) $\lambda_{max}$ 225(sh) nm; MS (HR-ESI), m/z 280.1556 (M+H) $\Delta_{calc}$=2.7 ppm (C$_{15}$H$_{22}$NO$_4$); $^1$H NMR (DMSO-d$_6$).

Example 6

Preparation of Compound of Formula I-19 from I-16

A sample of compound of Formula I-16 (250 mg) was added to an acetone solution of sodium iodide (1.5 g in 10 ml) and the resulting mixture stirred for 6 days. The solution was then filtered through a 0.45 micron syringe filter and injected directly on a normal phase silica HPLC column (Phenomenex Luna 10u Silica, 25 cm×21.2 mm) in 0.95 ml aliquots. The HPLC conditions for the separation of compound formula I-19 from unreacted I-16 employed an isocratic HPLC method consisting of 24% ethyl acetate and 76% hexane, in which the majority of compound I-19 eluted 2.5 minutes before compound I-16. Equivalent fractions from each of 10 injections were pooled to yield 35 mg compound I-19. Compound I-19: UV (Acetonitrile/H$_2$O) 225 (sh), 255 (sh) nm; ESMS, m/z 406.0 (M+H); HRMS (ESI), m/z 406.0513 [M+H]$^+$, $\Delta_{calc}$=−0.5 ppm, C$_{15}$H$_{21}$NO$_4$I; $^1$H NMR in DMSO-d$_6$.

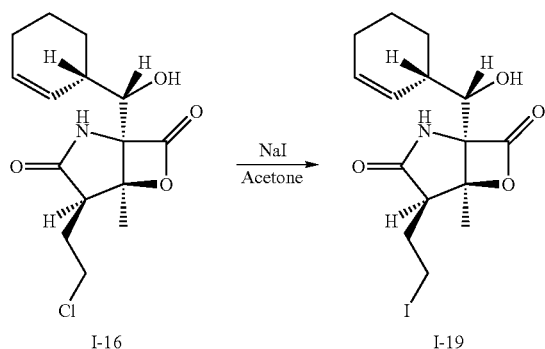

Example 7

Synthesis of the Compounds of Formulae I-2, I-3, and I-4

Compounds of Formulae I-2, I-3 and I-4 can be synthesized from compounds of Formulae I-16, I-17 and I-18, respectively, by catalytic hydrogenation.

Exemplary Depiction of Synthesis

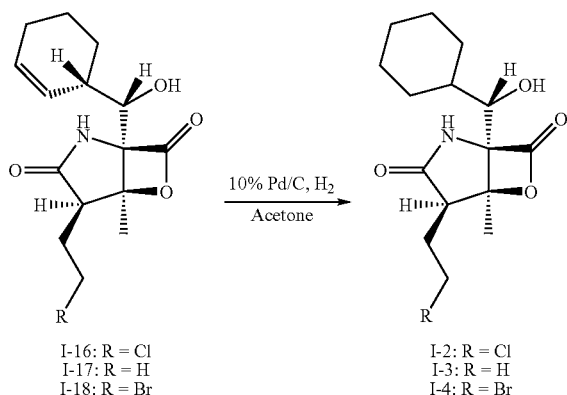

Example 7A

Catalytic Hydrogenation of Compound of Formula I-16

Compound of Formula I-16 (10 mg) was dissolved in acetone (5 mL) in a scintillation vial (20 mL) to which was added the 10% (w/w) Pd/C (1-2 mg) and a magnetic stirrer bar. The reaction mixture was stirred in a hydrogen atmosphere at room temperature for about 15 hours. The reaction mixture was filtered through a 3 cc silica column and washed with acetone. The filtrate was filtered again through 0.2 µm Gelman Acrodisc to remove any traces of catalyst. The solvent was evaporated off from filtrate under reduced pressure to yield the compound of Formula I-2 as a pure white powder: UV (acetonitrile/H$_2$O): $\lambda_{max}$ 225 (sh) nm.

Example 7B

Catalytic Hydrogenation of Compound of Formula I-17

Compound of Formula I-17 (5 mg) was dissolved in acetone (3 mL) in a scintillation vial (20 mL) to which was added the 10% (w/w) Pd/C (about 1 mg) and a magnetic stirrer bar. The reaction mixture was stirred in a hydrogen atmosphere at room temperature for about 15 hours. The reaction mixture was filtered through a 0.2 µm Gelman Acrodisc to remove the catalyst. The solvent was evaporated off from filtrate to yield the compound of Formula I-3 as a white powder which was purified by normal phase HPLC using the following conditions:

| | |
|---|---|
| Column: | Phenomenex Luna 10u Silica |
| Dimensions: | 25 cm × 21.2 mm ID |
| Flow rate: | 14.5 ml/min |
| ~~Detection:~~ | ~~ELSD~~ |
| Solvent: | 5% to 60% EtOAc/Hex for 19 min, 60 to 100% EtOAc in 1 min, then 4 min at 100% EtOAc |

Compound of Formula I-3 eluted at 22.5 min as a pure compound: UV (acetonitrile/H$_2$O): $\lambda_{max}$ 225 (sh) nm. Formula I-3: m/z 282 (M+H), 304 (M+Na).

Example 7C

Catalytic Hydrogenation of Compound of Formula I-18

3.2 mg of compound of Formula I-18 was dissolved in acetone (3 mL) in a scintillation vial (20 mL) to which was added the 10% (w/w) Pd/C (about 1 mg) and a magnetic stirrer bar. The reaction mixture was stirred in hydrogen atmosphere at room temperature for about 15 hours. The reaction mixture was filtered through a 0.2 µm Gelman Acrodisc to remove the catalyst. The solvent was evaporated off from filtrate to yield the compound of Formula I-4 as a white powder which was further purified by normal phase HPLC using the following conditions:

| | |
|---|---|
| Column: | Phenomenex Luna 10u Silica |
| Dimensions: | 25 cm × 21.2 mm ID |
| Flow rate: | 14.5 ml/min |
| Detection: | ELSD |
| Solvent: | 5% to 80% EtOAc/Hex for 19 min, 80 to 100% EtOAc in 1 min, then 4 min at 100% EtOAc |

Compound of Formula I-4 eluted at 16.5 min as a pure compound: UV (acetonitrile/H$_2$O): $\lambda_{max}$ 225 (sh) nm. Formula I-4: m/z 360 (M+H), 382 (M+Na).

In addition, high resolution mass spectrometry data were obtained for compounds I-2, I-3, and I-4. Compound I-2: HRMS (ESI), m/z 316.1305 [M+H]$^+$, $\Delta_{calc}$=−3.5 ppm, C$_{15}$H$_{23}$NO$_4$Cl. Compound I-3: HRMS (ESI), m/z 282.1706 [M+H]$^+$, $\Delta_{calc}$=0.3 ppm, C$_{15}$H$_{24}$NO$_4$. Compound I-4: HRMS (ESI), m/z 360.0798 [M+H]$^+$, $\Delta_{calc}$=−3.4 ppm, C$_{15}$H$_{23}$NO$_4$Br.

Example 8

Synthesis of the Compounds of Formulae I-5A and I-5B

Compounds of Formula I-5A and Formula I-5B can be synthesized from compound of Formula I-16 by epoxidation with mCPBA.

Compound of Formula I-16 (101 mg, 0.32 mmole) was dissolved in methylenechloride (30 mL) in a 100 ml of round bottom flask to which was added 79 mg (0.46 mmole) of meta-chloroperbenzoic acid (mCPBA) and a magnetic stir bar. The reaction mixture was stirred at room temperature for about 18 hours. The reaction mixture was poured onto a 20 cc silica flash column and eluted with 120 ml of CH$_2$Cl$_2$, 75 ml of 1:1 ethyl acetate/hexane and finally with 40 ml of 100% ethyl acetate. The 1:1 ethyl acetate/hexane fractions yield a mixture of diastereomers of epoxyderivatives, Formula I-5A and I-5B, which were separated by normal phase HPLC using the following conditions:

| Column | Phenomenex Luna 10u Silica |
|---|---|
| Dimensions | 25 cm × 21.2 mm ID |
| Flow rate | 14.5 ml/min |
| Detection | ELSD |
| Solvent | 25% to 80% EtOAc/Hex over 19 min, 80 to 100% EtOAc in 1 min, then 5 min at 100% EtOAc |

Compound Formula I-5A (major product) and I-5B (minor product) eluted at 21.5 and 19 min, respectively, as pure compounds. Compound I-5B was further chromatographed on a 3 cc silica flash column to remove traces of chlorobenzoic acid reagent.

Chemical Structures:

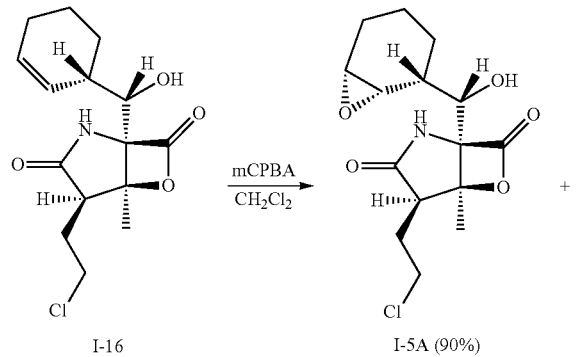

I-16    I-5A (90%)

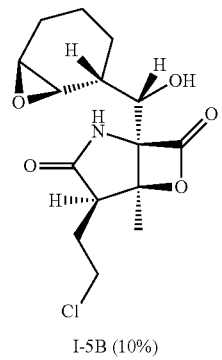

I-5B (10%)

Structural Characterization

Formula I-5A: UV (Acetonitrile/H$_2$O) $\lambda_{max}$ 225 (sh) nm. Low Res. Mass: m/z 330 (M+H), 352 (M+Na); HRMS (ESI), m/z 330.1099 [M+H]$^+$, $\Delta_{calc}$=−2.9 ppm, C$_{15}$H$_{21}$NO$_5$Cl.

Formula I-5B: UV (Acetonitrile/H$_2$O) $\lambda_{max}$ 225 (sh) nm. Low Res. Mass: m/z 330 (M+H), 352 (M+Na); HRMS (ESI), m/z 330.1105 [M+H]$^+$, $\Delta_{calc}$=−0.9 ppm, C$_{15}$H$_{21}$NO$_5$Cl.

Example 9

Synthesis of the Compounds of Formulae IV-1, IV-2, IV-3 and IV-4

Synthesis of Diol Derivatives (Formula IV-2)

Diols can be synthesized by Sharpless dihydroxylation using AD mix-α and β: AD mix-α is a premix of four reagents, K$_2$OsO$_2$(OH)$_4$; K$_2$CO$_3$; K$_3$Fe(CN)$_6$; (DHQ)$_2$-PHAL [1,4-bis(9-O-dihydroquinine)phthalazine] and AD mix-β is a premix of K$_2$OsO$_2$(OH)$_4$; K$_2$CO$_3$; K$_3$Fe(CN)$_6$; (DHQD)$_2$-PHAL [1,4-bis(9-O-dihydroquinidine)phthalazine] which are commercially available from Aldrich. Diol can also be synthesized by acid or base hydrolysis of epoxy compounds (Formula I-5A and I-5B) which may be different to that of products obtained in Sharpless dihydroxylation in their stereochemistry at carbons bearing hydroxyl groups Sharpless Dihydroxylation of Compounds I-16, I-17 and I-18

Any of the compounds of Formulae I-16, I-17 and I-18 can be used as the starting compound. In the example below, compound of Formula I-16 is used. The starting compound is dissolved in t-butanol/water in a round bottom flask to which is added AD mix-α or β and a magnetic stir bar. The reaction is monitored by silica TLC as well as mass spectrometer. The pure diols are obtained by usual workup and purification by flash chromatography or HPLC. The structures are confirmed by NMR spectroscopy and mass spectrometry. In this method both hydroxyl groups are on same side.

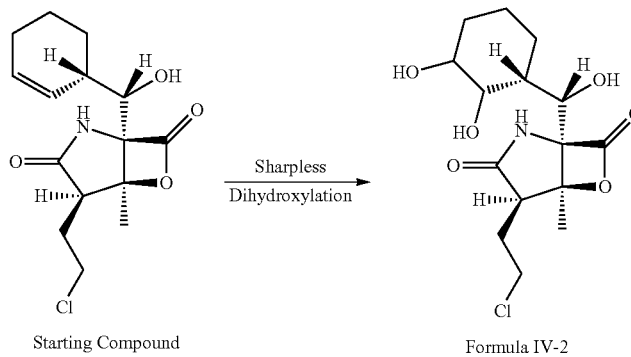
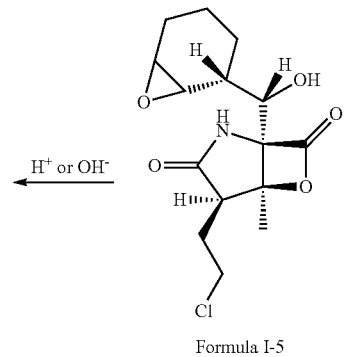

Starting Compound → Formula IV-2 ← Formula I-5

Sharpless Dihydroxylation    H⁺ or OH⁻

Nucleophilic Ring Opening of Epoxy Compounds (I-5):

The epoxy ring is opened with various nucleophiles like NaCN, NaN₃, NaOAc, HBr, HCl, etc. to create various substituents on the cyclohexane ring, including a hydroxyl substituent.

Examples

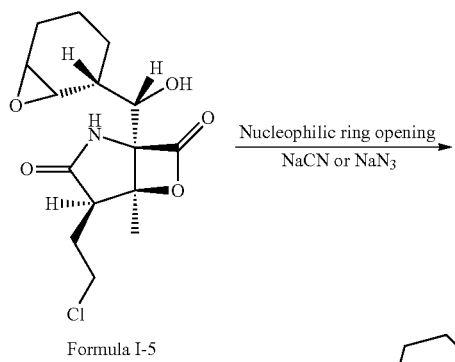

Formula I-5 → Nucleophilic ring opening NaCN or NaN₃ →

Compound of Formula I-5A (3.3 mg) was dissolved in acetonitrile (0.5 ml) in a 1 dram vial to which was added 5% HCl (500 ul) and a magnetic stir bar. The reaction mixture was stirred at room temperature for about an hour. The reaction was monitored by mass spectrometry. The reaction mixture was directly injected on normal phase HPLC to obtain compound of Formula IV-3C as a pure compound without any work up. The HPLC conditions used for the purification were as follows: Phenomenex Luna 10u Silica column (25 cm×21.2 mm ID) with a solvent gradient of 25% to 80% EtOAc/Hex over 19 min, 80 to 100% EtOAc in 1 min, then 5 min at 100% EtOAc at a flow rate of 14.5 ml/min. An ELSD was used to monitor the purification process. Compound of Formula IV-3C eluted at about 18 min (2.2 mg). Compound of Formula IV-3C: UV (Acetonitrile/H₂O) $\lambda_{max}$ 225 (sh) nm; ESMS, m/z 366 (M+H), 388 (M+Na); HRMS (ESI), m/z 366.0875 [M+H]⁺, $\Delta_{calc}$=0.0 ppm, $C_{15}H_{22}NO_5Cl_2$; ¹H NMR in DMSO-d₆. The stereochemistry of the compound of Formula IV-3C was determined based on coupling constants observed in the cyclohexane ring in 1:1 $C_6D_6$/DMSO-d₆.

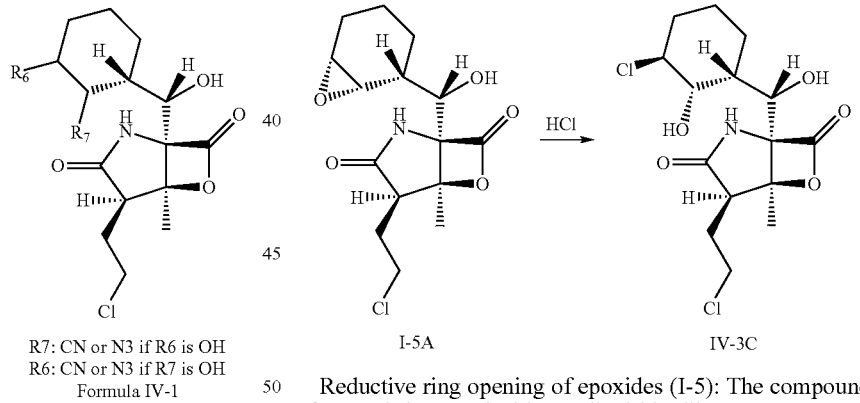

R7: CN or N3 if R6 is OH
R6: CN or N3 if R7 is OH
Formula IV-1

I-5A → HCl → IV-3C

The epoxy is opened with HCl to make Formula IV-3:

Reductive ring opening of epoxides (I-5): The compound of Formula is treated with metalhydrides like BH₃-THF complex to make compound of Formula IV-4.

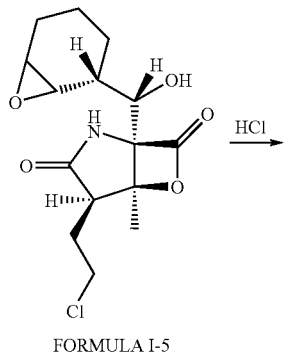

FORMULA I-5 → HCl → FORMULA IV-3

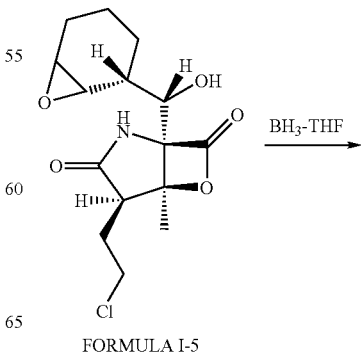

FORMULA I-5 → BH₃-THF →

FORMULA IV-4

I-16

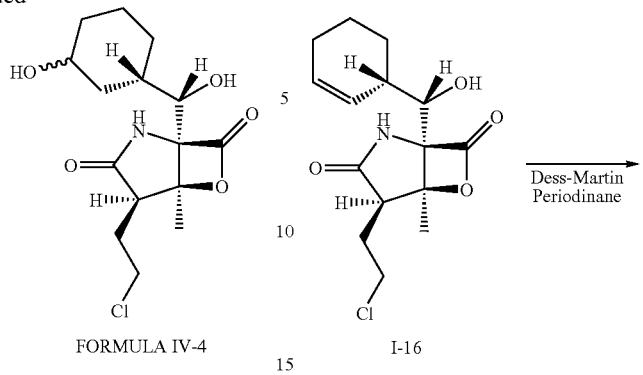

I-13C

I-8C

Example 10

Synthesis of the Compounds of Formulae I-13C and I-8C

Compound of Formula I-16 (30 mg) was dissolved in $CH_2Cl_2$ (6 ml) in a scintillation vial (20 ml) to which Dess-Martin Periodinane (122 mg) and a magnetic stir bar were added. The reaction mixture was stirred at room temperature for about 2 hours. The progress of the reaction was monitored by TLC (Hex:EtOAc, 6:4) and analytical HPLC. From the reaction mixture, the solvent volume was reduced to one third, absorbed on silica gel, poured on top of a 20 cc silica flash column and eluted in 20 ml fractions using a gradient of Hexane/EtOAc from 10 to 100%. The fraction eluted with 30% EtOAc in Hexane contained a mixture of rotamers of Formula I-13C in a ratio of 1.5:8.5. The mixture was further purified by normal phase HPLC using the Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula I-13C eluted at 13.0 and 13.2 mins as a mixture of rotamers with in a ratio of 1.5:8.5 (7 mg). Formula I-13C: UV (Acetonitrile/$H_2O$) $\lambda_{max}$ 226 (sh) & 300 (sh) nm; ESMS, m/z 312 (M+H)$^+$, 334 (M+Na)$^+$; HRMS (ESI), m/z 312.1017 [M+H]$^+$, $\Delta_{calc}$=4.5 ppm, $C_{15}H_{19}NO_4Cl$; $^1$H NMR in DMSO-$d_6$.

The rotamer mixture of Formula I-13C (4 mg) was dissolved in acetone (1 ml) in a scintillation vial (20 ml) to which a catalytic amount (0.5 mg) of 10% (w/w) Pd/C and a magnetic stir bar were added. The reaction mixture was stirred in a hydrogen atmosphere at room temperature for about 15 hours. The reaction mixture was filtered through a 0.2 μm Gelman Acrodisc to remove the catalyst. The solvent was evaporated from the filtrate to yield compound of Formula I-8C as a colorless gum which was further purified by normal phase HPLC using a Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula I-8C (1 mg) eluted at 13.5 min as a pure compound. Formula I-8C: UV (Acetonitrile/$H_2O$) $\lambda_{max}$ 225 (sh) nm; ESMS, m/z 314 (M+H)$^+$, 336 (M+Na)$^+$; HRMS (ESI), m/z 314.1149 [M+H]$^+$, $\Delta_{calc}$=3.3 ppm, $C_{15}H_{21}NO_4Cl$; $^1$H NMR in DMSO-$d_6$.

Example 11

Synthesis of the Compound of Formula I-25 from I-13C

The rotamer mixture of Formula I-13C (5 mg) was dissolved in dimethoxy ethane (monoglyme; 1.5 ml) in a scintillation vial (20 ml) to which water (15 μl (1% of the final solution concentration)) and a magnetic stir bar were added. The above solution was cooled to −78° C. on a dry ice-acetone bath, and a sodium borohydride solution (3.7 mg of $NaBH_4$ in 0.5 ml of monoglyme (created to allow for slow addition)) was added drop-wise. The reaction mixture was stirred at −78° C. for about 14 minutes. The reaction mixture was acidified using 2 ml of 4% HCl solution in water and extracted with $CH_2Cl_2$. The organic layer was evaporated to yield mixture of compound of formulae I-25 and I-16 in a 9.5:0.5 ratio as a white solid, which was further purified by normal phase HPLC using a Phenomenex Luna 10u Silica column (25 cm×21.2 mm ID). The mobile phase was 24% EtOAc/76% Hexane, which was held isocratic for 19 min, followed by a linear gradient of 24% to 100% EtOAc over 1 min, and held at 100% EtOAc for 3 min; the flow rate was 25 ml/min. An ELSD was used to monitor the purification process. Compound of formula I-25 (1.5 mg) eluted at 11.64 min as a pure compound. Compound of Formula I-25: UV (Acetonitrile/$H_2O$) $\lambda_{max}$ 225 (sh) nm; ESMS, m/z 314 (M+H)$^+$, 336 (M+Na)$^+$; HRMS (ESI), m/z 314.1154 [M+H]$^+$, $\Delta_{calc}$=−0.6 ppm, $C_{15}H_{21}NO_4Cl$; $^1$H NMR in DMSO-$d_6$.

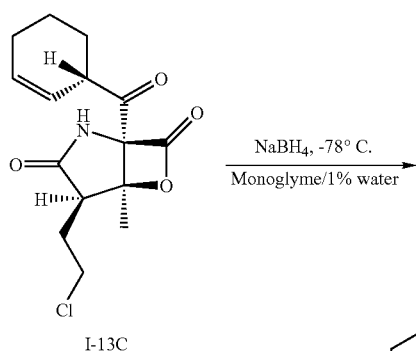

I-13C

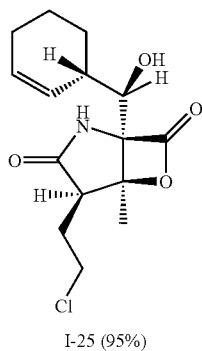

I-25 (95%)

Example 12

Synthesis of the Compounds of Formulae I-31, I-32 and I-49 from I-13C; and Compounds of Formulae I-33, I-34, I-35 and I-36 from I-31 and I-32

A rotamer mixture of the Compound of Formula I-13C (20 mg) was dissolved in acetone (4 ml) in a scintillation vial (20 ml) to which a catalytic amount (3 mg) of 10% (w/w) Pd/C and a magnetic stir bar were added. The reaction mixture was stirred at room temperature for about 15 hours. The reaction mixture was filtered through a 0.2 μm Gelman Acrodisc to remove the catalyst. The solvent was evaporated from the filtrate to yield a mixture of diastereomers of hydroxy derivatives of Formulae I-31 and I-32 (1:1) and a minor compound I-49, which were separated by reversed phase HPLC using Ace 5u C18 column (150 mm×22 mm ID) with a solvent gradient of 90% to 30% $H_2O$/Acetonitrile over 15 min, 70 to 100% Acetonitrile over 5 min, holding at 100% Acetonitrile for 4 min, at a flow rate of 14.5 ml/min. A diode array detector was used to monitor the purification process. Compound I-31 (2 mg), I-32 (2 mg) and I-49 (0.2 mg) eluted at 10.6, 10.8 and 11.54 min, respectively, as pure compounds. I-31: UV (Acetonitrile/$H_2O$) $\lambda_{max}$ 250 (sh) nm; ESMS m/z 328.1 $(M+H)^+$ & 350.0 $(M+Na)^+$. I-32: UV (Acetonitrile/$H_2O$) $\lambda_{max}$ 250 (sh) nm; ESMS, m/z 328.1 $(M+H)^+$ & 350.0 $(M+Na)^+$. I-49: UV (Acetonitrile/$H_2O$) $\lambda_{max}$ 250 (sh) and 320 nm; ESMS, m/z 326.0 $(M+H)^+$, 343.1 $(M+H_2O)^+$ & 348.0 $(M+Na)^+$.

In an alternate method, compounds I-31, I-32 and I-49 were separated by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process.

The ketone of the compounds of formula I-31 and I-32 can be reduced by using sodium borohydride at 0 to −10° C. in monoglyme solvent for about 14 minutes. The reaction mixture can be acidified using 4% HCl solution in water and extracted with $CH_2Cl_2$. The organic layer can be evaporated to yield the mixtures of compounds of formulae I-33, I-34, I-35 and I-36 which can be separated by chromatographic methods.

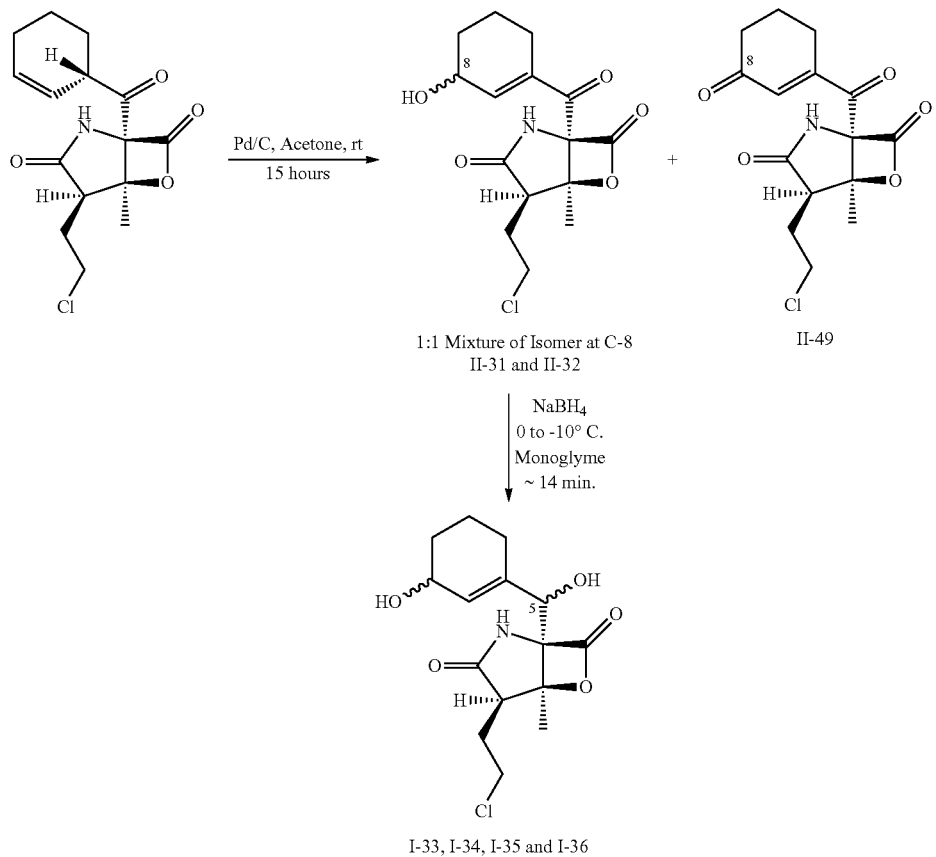

I-33, I-34, I-35 and I-36

Example 13

Synthesis of the Compound of Formulae I-21 from I-19

Acetone (7.5 ml) was vigorously mixed with 5 N NaOH (3 ml) and the resulting mixture evaporated to a minimum volume in vacuo. A sample of 100 μl of this solution was mixed with compound of Formula I-19 (6.2 mg) in acetone (1 ml) and the resulting biphasic mixture vortexed for 2 minutes. The reaction solution was immediately subjected to preparative C18 HPLC. Conditions for the purification involved a linear gradient if 10% acetonitrile/90% water to 90% acetonitrile/10% water over 17 minutes using an Ace 5μ C18 HPLC column of dimensions 22 mm id by 150 mm length. Compound of Formula I-21 eluted at 9.1 minutes under these conditions to yield 0.55 mg compound. Compound of Formula I-21: UV (Acetonitrile/$H_2O$) 225 (sh), ESMS, m/z 296.1 (M+H); $^1$H NMR in DMSO-$d_6$.

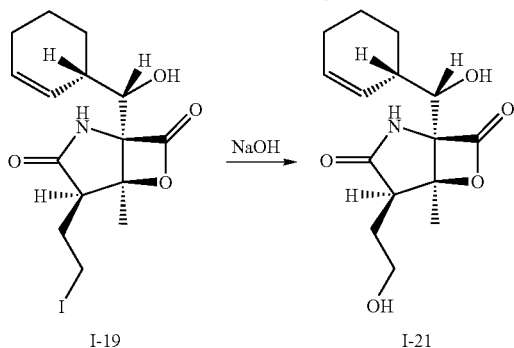

Example 14

Synthesis of the Compound of Formulae I-22 from I-19

A sample of 60 mg sodium propionate was added to a solution of compound of Formula I-19 (5.3 mg) in DMSO (1 ml) and the mixture sonicated for 5 minutes, though the sodium propionate did not completely dissolve. After 45 minutes, the solution was filtered through a 0.45μ syringe filter and purified directly using HPLC. Conditions for the purification involved a linear gradient if 10% acetonitrile/90% water to 90% acetonitrile/10% water over 17 minutes using an Ace 5μ C18 HPLC column of dimensions 22 mm id by 150 mm length. Under these conditions, compound of Formula I-22 eluted at 12.3 minutes to yield 0.7 mg compound (15% isolated yield). UV (Acetonitrile/$H_2O$) 225 (sh), ESMS, m/z 352.2 (M+H); HRMS (ESI), m/z 352.1762 [M+H]$^+$, $\Delta_{calc}$=0.6 ppm, $C_{18}H_{26}NO_6$; $^1$H NMR in DMSO-$d_6$.

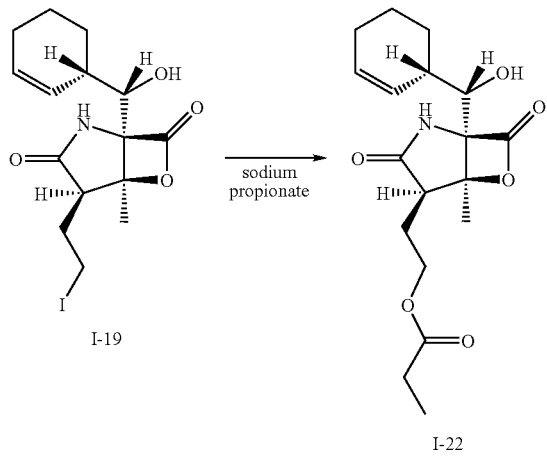

Example 15

Synthesis of the Compound of Formula I-29 from I-19

A sample of $NaN_3$ (80 mg) was dissolved in DMSO (1 ml) and transferred to a vial containing Compound I-19 (6.2 mg) which was contaminated with approximately 10% Compound I-16. The solution was incubated at room temperature for 1 hr prior to purification on C18 HPLC (ACE 5μ C18-HL, 150 mm×21 mm ID) using a solvent gradient of 10% acetonitrile/90% $H_2O$ to 90% acetonitrile/10% $H_2O$ over 17 minutes. Using this method, the desired azido derivative I-29 co-eluted with Compound I-16 contaminant at 12.5 minutes (4.2 mg, 85% yield). A 2.4 mg portion of compound I-29 was further purified using additional C18 HPLC chromatography (ACE 5μ C18-HL, 150 mm×21 mm ID) using an isocratic solvent gradient consisting of 35% acetonitrile/65% $H_2O$. Under these conditions compound I-29 eluted after 20 minutes, while Compound I-16 eluted after 21.5 minutes. The resulting sample consisted of 1.1 mg Compound I-29 was used for characterization in biological assays.

Compound I-29: UV (Acetonitrile/$H_2O$) 225 (sh), ESMS, m/z 321.1 (M+H); $^1$H NMR in DMSO-$d_6$.

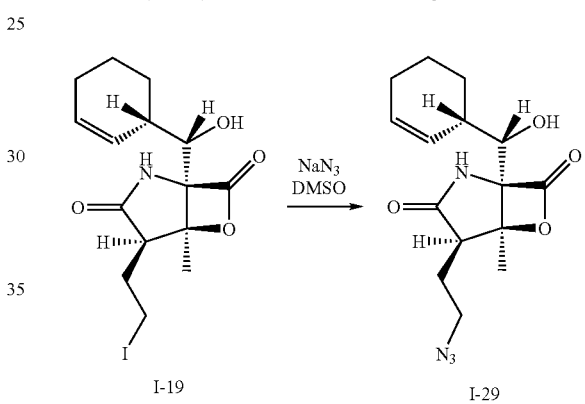

Example 16

Synthesis of the Compounds of Formulae I-37 and I-38 from I-19

The compounds of Formulae I-37 and I-38 can be prepared from the compound of Formula I-19 by cyano-de-halogenation or thiocyanato-de-halogenation, respectively. Compound I-19 can be treated with NaCN or KCN to obtain compound I-37. Alternatively, Compound I-19 can be treated with NaSCN or KSCN to obtain compound I-38.

Synthesis of the compound of Formula I-38 from I-19:

The compound of formula I-19 (10.6 mg, 0.02616 mmol) was dissolved in 1.5 ml of acetone in a scintillation vial (20 ml) to which sodium thiocyanate (10.0 mg, 0.1234 mmol), triethylamine (5 μl, 0.03597 mmol) and a magnetic stir bar were added. The reaction mixture was stirred at room temperature for 72 hours. The reaction mixture was concentrated in vacuo to yield the compound I-38. Compound I-38 was purified by normal phase HPLC using a Phenomenex Luna 10μ Silica column (25 cm×21.2 mm ID) with a solvent gradient of 0 to 95% $H_2O$/Acetonitrile over 21 min, at a flow rate of 14.5 ml/min. Diode array detector was used to monitor the purification process. Compound I-38 (3.0 mg, 34% yield) eluted at 18.0 min as a pure compound. I-38: UV Acetonitrile/$H_2O$ $\lambda_{max}$ 203 (sh) nm; ESMS m/z 337.1 (M+H)+& 359.1 (M+Na)$^+$.

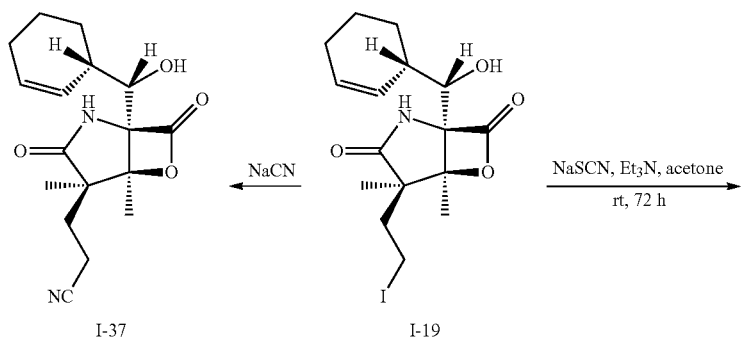

Example 17

Synthesis of the Compound of Formula I-39 from I-19

Thiols and thioethers of the Formula I-39 can be formed by dehalogenation of the compound of Formula I-19. Thiols (R=H) can be formed by treatment of Compound I-19 with NaSH, for example, while thioethers (R=alkyl) can be formed by treatment of Compound I-19 with salts of thiols, or alternatively, by treatment with thiols themselves by running the reaction in benzene in the presence of DBU.

Example 19

Synthesis of the Compound of Formula I-41A from I-21

The compound of the Formula I-41A can be prepared by treatment of the compound of Formula I-21 (or a protected derivative of I-21, where the C-5 alcohol or lactam NH are protected, for example) with methyl sulfonyl chloride (mesyl chloride) in pyridine, for example, or by treatment with mesyl chloride in the presence of triethylaminde. Other sulfonate esters can be similarly prepared.

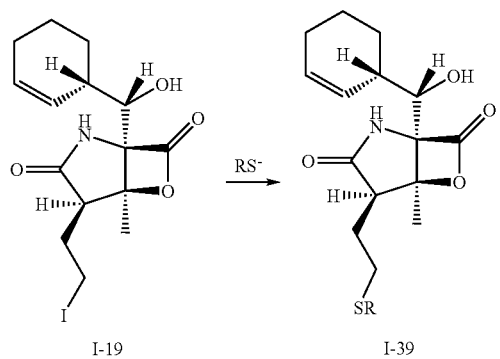

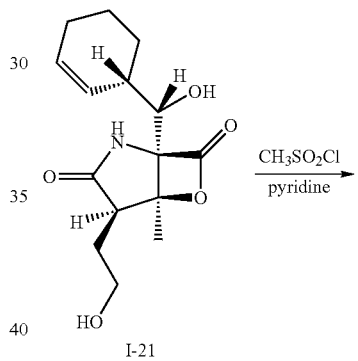

Example 18

Synthesis of the Compound of Formula I-40 from I-39

Sulfoxides (n=1) and sulfones (n=2) of the Formula I-40 can be formed by oxidation of thioethers of the Formula I-39, for example, with hydrogen peroxide or other oxidizing agents.

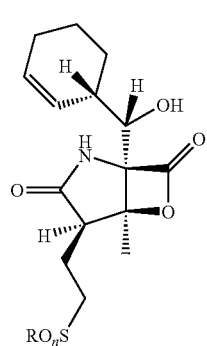

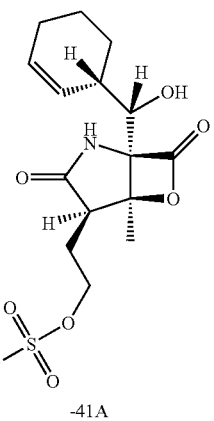

Example 20

Synthesis of the Compound of Formula I-46 from I-19 OR I-41A

The alkene of the Formula I-46 can be prepared by dehydroiodination of the compound of Formula I-19, or by hydromesyloxy elimination of the compound of Formula I-41A, for example, by treatment with base.

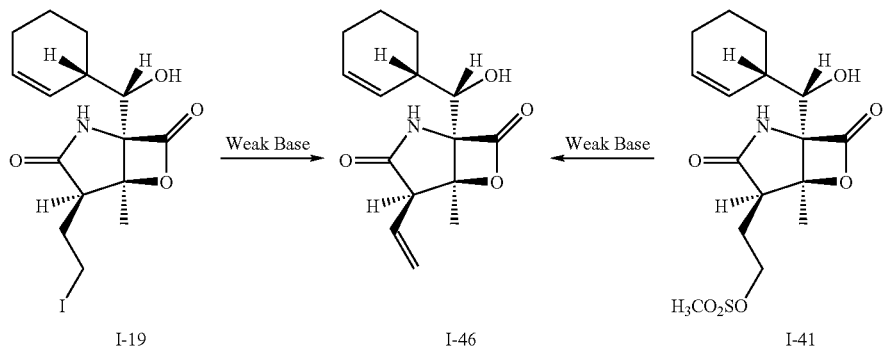

Example 21

Synthesis of the Compound of Formula I-42A

Synthesis of boronic acids or esters, for example, the compound of the Formula I-42A, can be achieved as outlined in the retrosynthetic scheme below. Hydroboration of the alkene of Formula I-46 gives the corresponding alkyl borane, which can be converted to the corresponding boronic acid or ester, for example, the compound of the Formula I-42A.

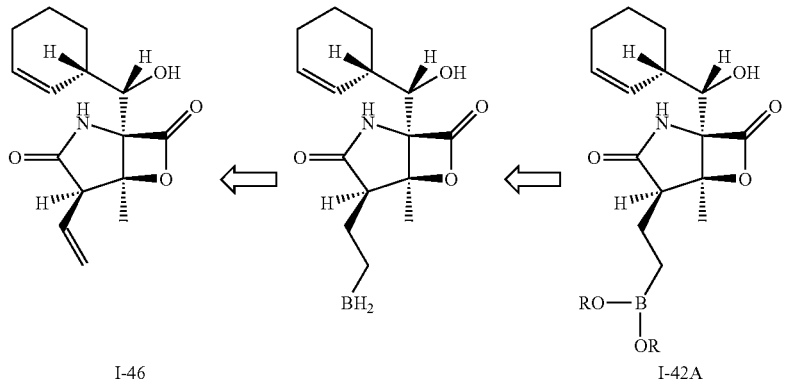

Example 22

Synthesis of the Compound of Formula I-43A

The compound of the Formula I-43A can be prepared by treatment of the compound of Formula I-19 with triphenyl phosphine to make a phosphorus ylide, which can be treated with various aldehydes, for example, glyoxylic acid methyl ester, to make Formula I-43A.

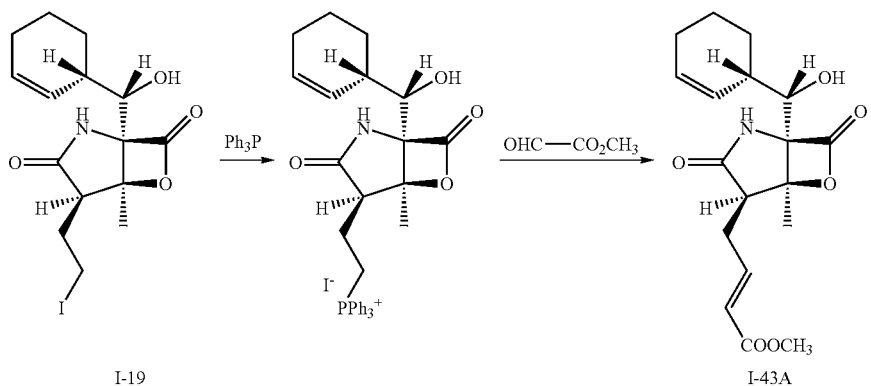

Example 23

Synthesis of the Compound of Formula I-30 from I-19

A portion of CuI (100 mg) was placed in a 25 ml pear bottom flask and flushed with Ar gas for 30 minutes. Ar gas flow was maintained through the flask throughout the course of the reaction. The vessel was cooled to −78° C. prior to addition of dry THF (5 ml) followed by the immediate dropwise addition of a solution of methyllithium in dry THF (5.0 ml, 1.6 M) with vigorous stirring. A solution of Compound I-19 in dry THF (12 mg Compound I-19, 1 ml THF) was added slowly to the clear dialkylcuprate solution and the resulting mixture stirred at −78° C. for 1 hr. The reaction was quenched by washing the THF solution through a plug of silica gel (1 cm diameter by 2 cm length) along with further washing using a solution of 50% EtOAc/50% hexanes (50 ml). The combined silica plug washes were dried in vacuo and subjected to further C18 HPLC purification in 2 injections (ACE 5μ C18-HL, 150 mm×21 mm ID) using an isocratic solvent gradient consisting of 35% acetonitrile/65% $H_2O$. Compound I-30 eluted under these conditions at 23.5 minutes and yielded 2.4 mg material (27% isolated yield) at 90.8% purity as measured by analytical HPLC. An alternative normal phase purification method can be utilized using Phenomenex Luna 10μ Silica column (25 cm×21.2 mm ID) with a solvent gradient consisting of 100% hexanes/ethyl acetate to 0% hexanes over 20 minutes. Compound I-30 eluted under these conditions at 16.5 minutes and yielded 3.0 mg material (41% isolated yield) at 97.1% purity as measured by analytical HPLC.

Compound I-30: UV (Acetonitrile/$H_2O$) 225 (sh), ESMS, m/z 294.1 (M+H); HRMS (ESI), m/z 294.1696 $[M+H]^+$, $\Delta_{calc}$=−3.2 ppm, $C_{16}H_{24}NO_4$; $^1$H NMR in DMSO-d$_6$.

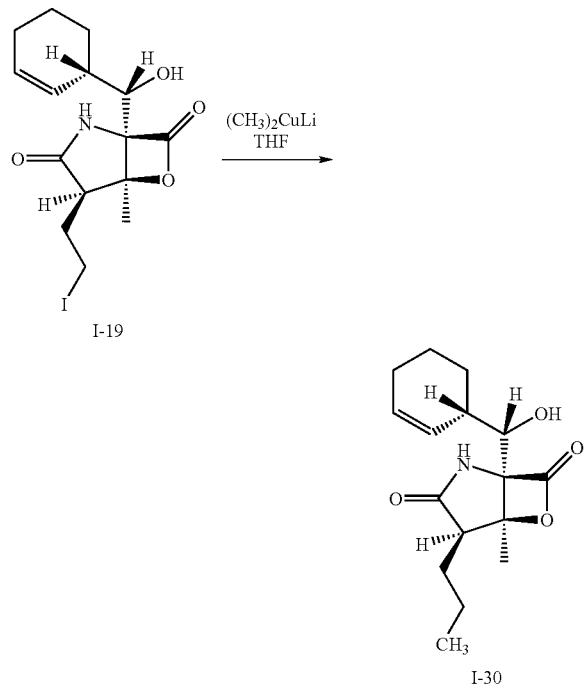

Compound I-30 can also be obtained by saline fermentation of strain CNB476. In one example, CNB476 was transferred to 500-mL flasks containing 100 mL production medium consisting of the following per liter of deionized water: starch, 10 g; yeast extract, 4 g; Hy-Soy, 4 g; ferric sulfate, 40 mg; potassium bromide, 100 mg; calcium carbonate, 1 g; and synthetic sea salt, 30 g. The production cultures were incubated at 28° C. and 250 rpm for 1 day. Approximately 2 g of sterile Amberlite XAD-7 resin was added to the production cultures. The production cultures were further incubated for 5 days. The resin was recovered from the broth and extracted with ethyl acetate. The extract was dried in vacuo. The dried extract (8 g) was then processed for the recovery of Compound I-30.

The crude extract was processed by flash chromatography using a Biotage Flash system. The flash chromatography was developed by the following step gradient: i) Hexanes (1 L); 1) 10% EtOAc in hexanes (1 L); Ii) 20% EtOAc in hexanes, first elution (1 L); iv) 20% EtOAc in hexanes, second elution (1 L); v) 20% EtOAc in hexanes, third elution (1 L); vi) 25% EtOAc in hexanes (1 L); vI) 50% EtOAc in hexanes (1 L); vIi) EtOAc (1 L). Fractions containing Compound I-30 was further purified by normal phase HPLC using an isocratic solvent system of 24% EtOAc/hexanes followed by a 100% EtOAc. Compound I-30 eluted 22 minutes into the isocratic portion of the run.

Fractions enriched in Compound I-30 were further processed by normal phase HPLC using a 27 minute linear gradient from 15% hexanes/85% EtOAc to 100% EtOAc. Compound I-30 eluted after 15 min.

Example 24

Synthesis of the Compound of Formulae I-44 and VI-1A from I-16

The compound of Formula I-16 (30 mg, 0.096 mmol) was dissolved in $CH_2Cl_2$ (9 ml) in a scintillation vial (20 ml) to which triethylamine (40 μl, 0.29 mmol), methyl-3-mercapto propionate (thiol, 250 μl) and a magnetic stir bar were added. The reaction mixture was stirred at room temperature for about 4 hours. The solvent was evaporated from the reaction mixture to yield a mixture of compounds of Formulae I-44 and VI-1A (19:1), which were separated by reversed phase HPLC using Ace 5u C18 column (150 mm×22 mm ID) with a solvent gradient of 35% to 90% $H_2O$/Acetonitrile over 17 min, 90 to 100% Acetonitrile over 1 min, holding at 100% Acetonitrile for 1 min, at a flow rate of 14.5 ml/min. Diode array detector was used to monitor the purification process. Compounds I-44 (20 mg) and VI-1A (1 mg) eluted at 11.68 and 10.88 min, respectively, as pure compounds. Compound I-44: UV (Acetonitrile/$H_2O$) $\lambda_{max}$ 240 (sh) nm; ESMS m/z 434.0 $(M+H)^+$ & 456.0 $(M+Na)^+$. Compound VI-1A: UV (Acetonitrile/$H_2O$) $\lambda_{max}$ 220 (sh) nm; ESMS, m/z 398.0 $(M+H)^+$ & 420.0 $(M+Na)^+$.

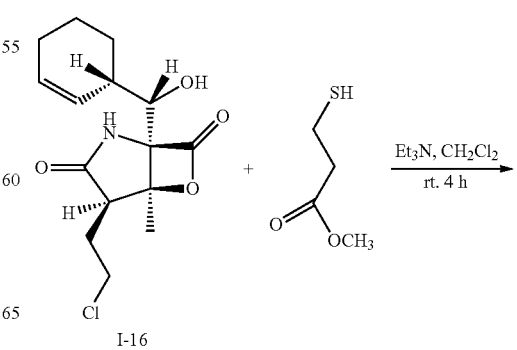

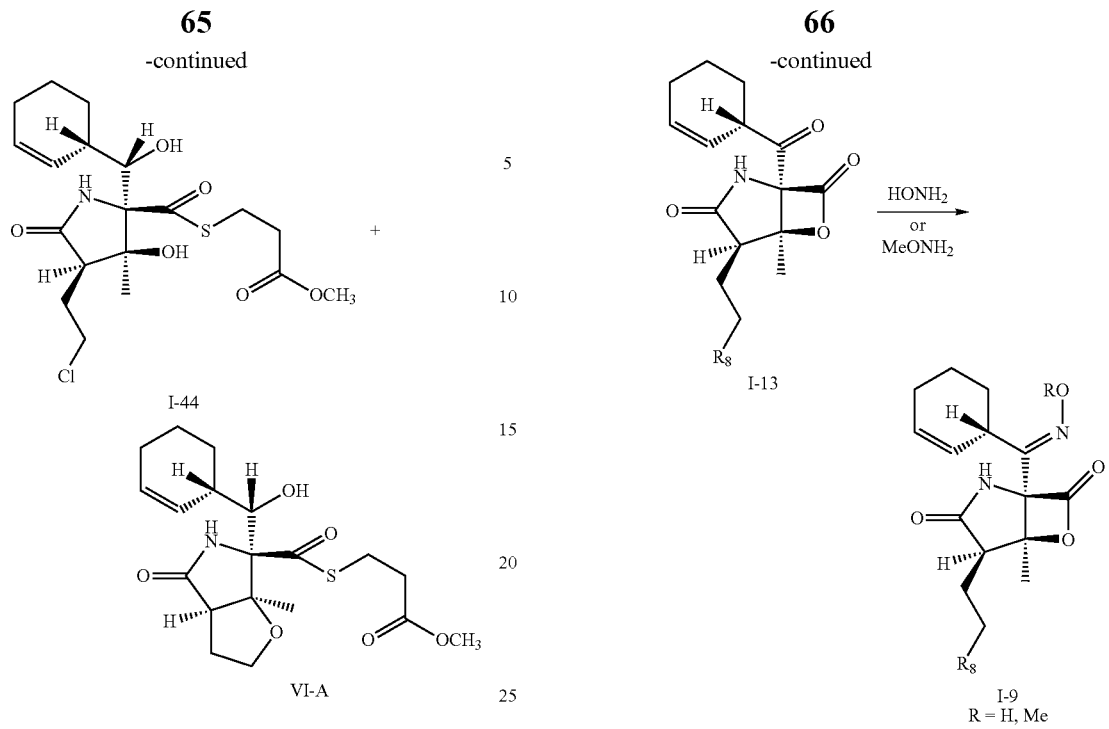

Example 25

Oxidation of Secondary Hydroxyl Group in Compounds of Formulae I-16, I-17 and I-18 and Reaction with Hydroxy or Methoxy Amines Any of the compounds of Formulae I-16, I-17 and I-18 can be used as the starting compound. The secondary hydroxyl group in the starting compound is oxidized using either of the following reagents: pyridinium dichromate (PDC), pyridinium chlorochromate (PCC), Dess-Martin periodinane or oxalyl chloride (Swern oxidation) (Ref: Organic Syntheses, collective volumes I-VII). Preferably, Dess-Martin periodinane can be used as a reagent for this reaction. (Ref: Fenteany G. et al. Science, 1995, 268, 726-73). The resulting keto compound is treated with hydroxylamine or methoxy amine to generate oximes.

Examples

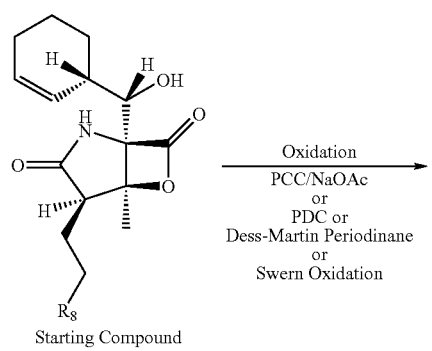

Example 26

Reductive Amination of Keto-Derivative

The keto derivatives, for example Formula I-8 and I-13, are treated with sodium cyanoborohydride (NaBH$_3$CN) in the presence of various bases to yield amine derivatives of the starting compounds which are subsequently hydrogenated with 10% Pd/C, H$_2$ to reduce the double bond in the cyclohexene ring.

Example

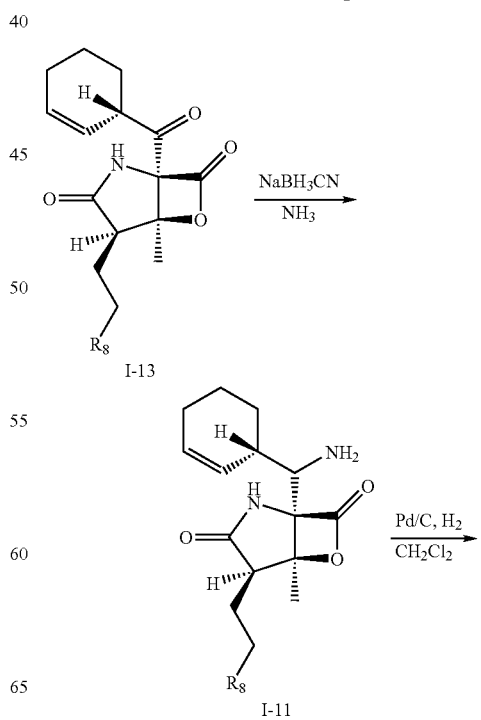

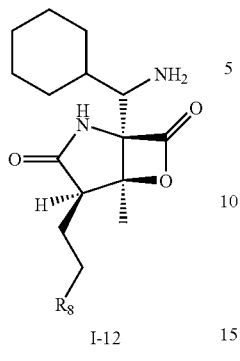

I-12

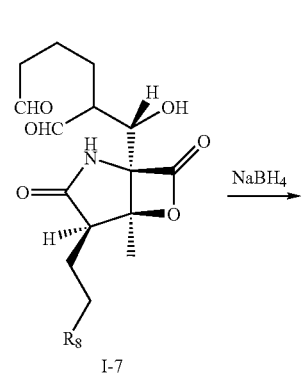

I-7

Example 27

Cyclohexene Ring Opening

Any compound of Formulae I-16, I-17 and I-18 can be used as a starting compound. The Starting Compounds can be protected, for example, at the alcohol and/or at the lactam nitrogen positions, and treated with $OsO_4$ and $NaIO_4$ in THF—$H_2O$ solution to yield dial derivatives which are reduced to the alcohol with $NaBH_4$. The protecting groups can be removed at the appropriate stage of the reaction sequence to produce I-7 or I-6.

Example

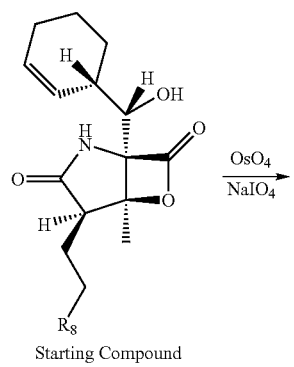

Starting Compound

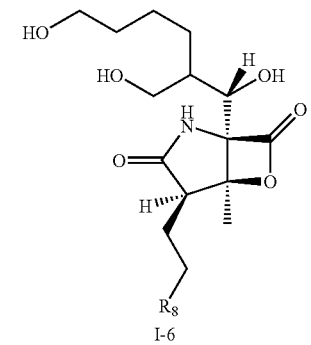

I-6

Example 28

Dehydration of Alcohol Followed by Aldehyde Formation at Lactone-Lactam Ring Junction A starting compound of any of Formulae I-16, I-17 or I-18 is dehydrated, for example, by treatment with mesylchloride in the presence of base, or, for example, by treatment with Burgess reagent or other dehydrating agents. The resulting dehydrated compound is treated with $OsO_4$, followed by $NaIO_4$, or alternatively by ozonolysis, to yield an aldehyde group at the lactone-lactam ring junction.

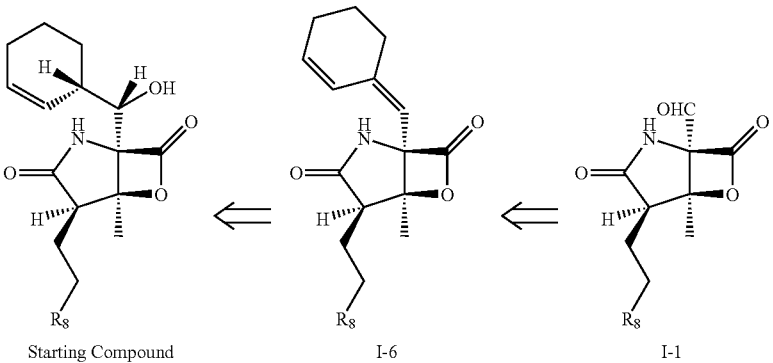

Starting Compound    I-6    I-1

Example 29
Oxidation of the Cyclohexene Ring to Produce Cyclohexadienes or a Phenyl Ring A Starting Compound, such as the ketone of Formula I-13C, is treated with Pd/C to produce a cyclohexadiene derivative. The new double bond can be at any position of the cyclohexene ring. The ketone can be reduced, for example, with sodium borohydride, to obtain the corresponding secondary alcohol(s). Alternatively, the cyclohexadiene derivative can be further treated, for example with DDQ, to aromatize the ring to a phenyl group. Similarly, the ketone can be reduced, for example, with sodium borohydride, to obtain the corresponding secondary alcohol(s).

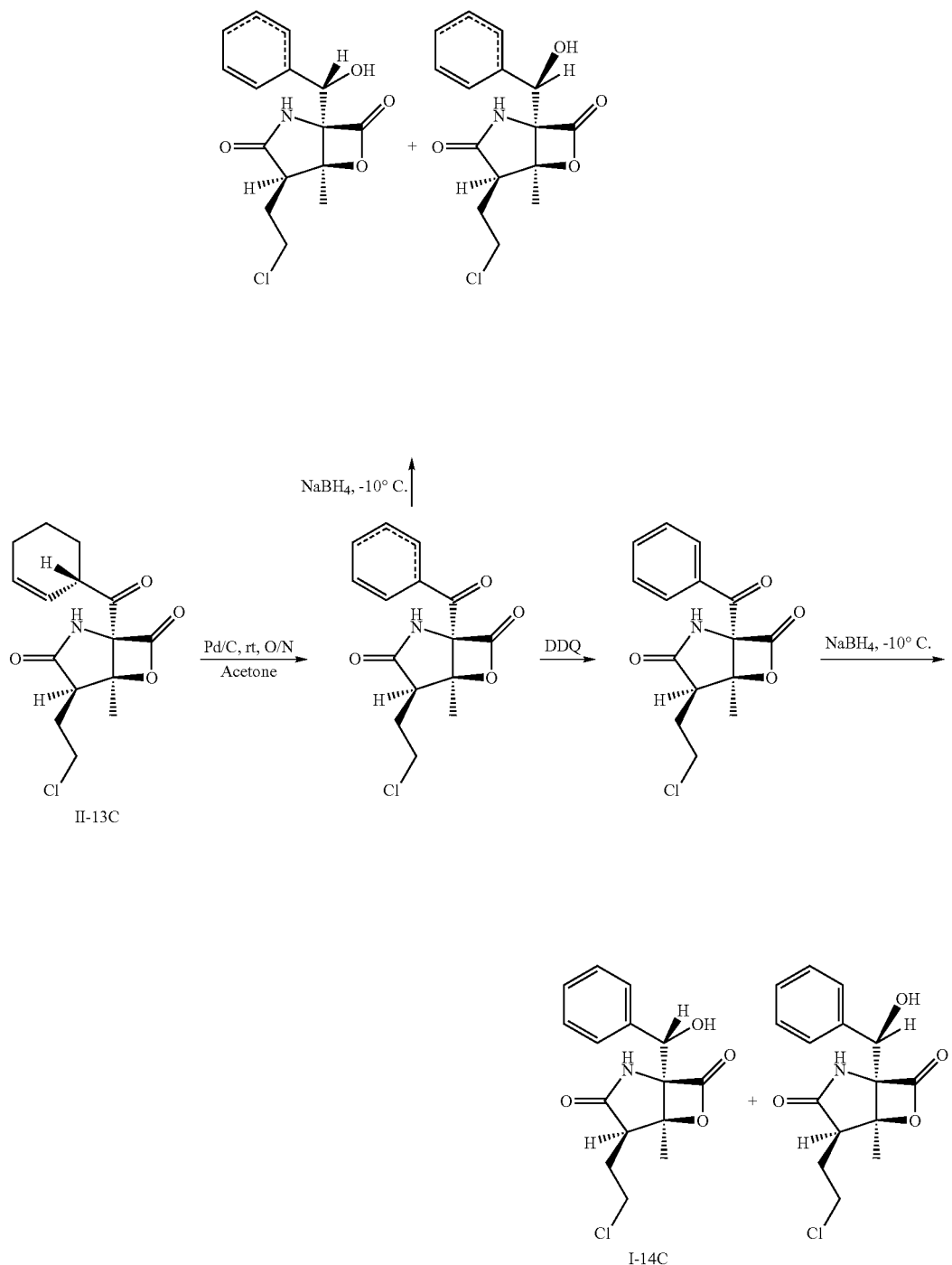

As an alternate method, the starting compound, such as the compound of Formula I-49, can be treated, for example with TMSCl to produce cyclohexadiene derivative. The cyclohexadiene derivative can be further treated, for example with DDQ, to aromatize the ring to a phenyl group. The OTMS on the phenyl group can be removed, for example, with acid or base. Similarly, the ketone can be reduced, for example, with sodium borohydride, to obtain the corresponding secondary alcohol(s).

further purified by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process. Compound I-47 (15 mg) eluted at 10.98 min as pure compound. Compound I-47: UV (Acetonitrile/$H_2O$) $\lambda_{max}$ 240 (sh) nm; ESMS m/z 400.1 $(M+H)^+$ & 422.1 $(M+Na)^+$.

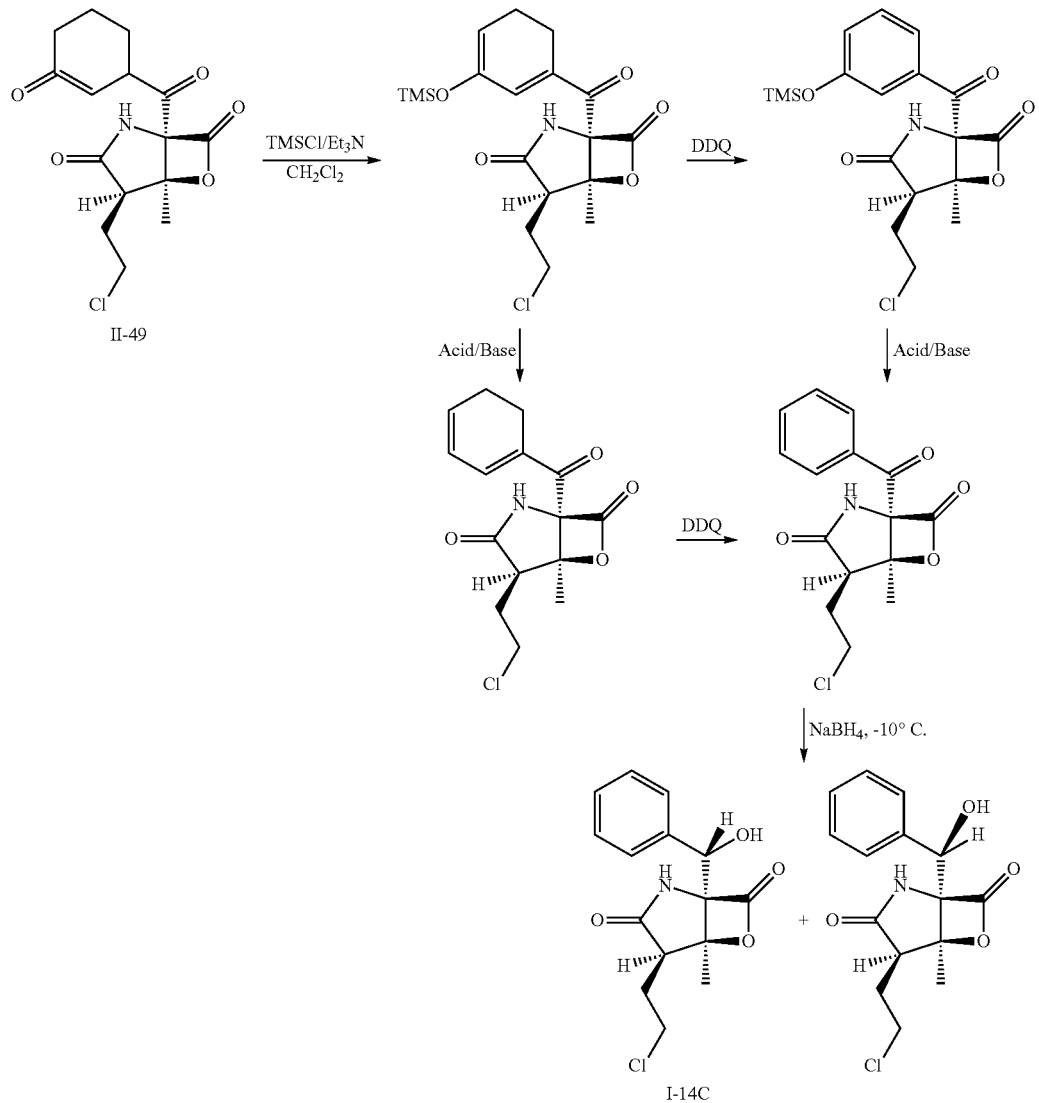

Example 30

Synthesis of the Compound of Formula I-47 from I-17

The compound of Formula I-17 (25 mg, 0.0896 mmol) was dissolved in $CH_2Cl_2$ (9 ml) in a scintillation vial (20 ml) to which triethylamine (38 μl, 0.27 mmol), methyl-3-mercapto propionate (thiol, 250 μl) and a magnetic stir bar were added. The reaction mixture was stirred at room temperature for about 4 hours. The solvent was evaporated from the reaction mixture to yield the compound of Formulae I-47, which was

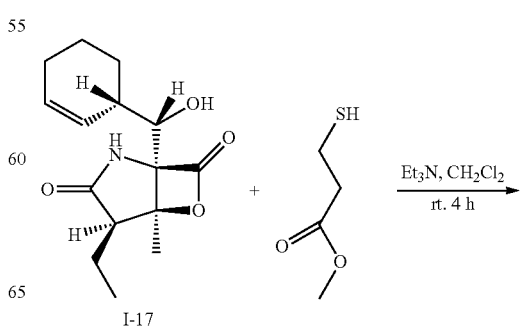

-continued

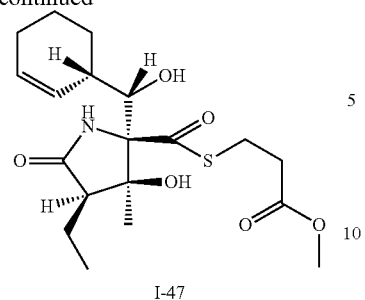

I-47

Example 31

Synthesis of the Compound of Formulae I-48 and VI-1B from I-16

The compound of Formula I-16 (15 mg, 0.048 mmol) was dissolved in 1:1 ratio of ACN/DMSO (8 ml) in a scintillation vial (20 ml) to which triethylamine (40 μl, 0.29 mmol), Glutathione (44.2 mg, 0.144 mmol) and a magnetic stir bar were added. The reaction mixture was stirred at room temperature for about 3 hours. The solvent was evaporated from the reaction mixture to yield the compound of Formula I-48, which was purified by reversed phase HPLC using Ace 5u C18 column (150 mm×22 mm ID) with a solvent gradient of 10% to 70% H$_2$O/Acetonitrile over 15 min, 70 to 100% Acetonitrile over 5 min, holding at 100% Acetonitrile for 4 min, at a flow rate of 14.5 ml/min. Diode array detector was used to monitor the purification process. Compound I-48 (10 mg) eluted as a pure compound at 8.255 min. Compound I-48: UV (Acetonitrile/H$_2$O) λ$_{max}$ 235 (sh) nm; ESMS m/z 621.0 (M+H)$^+$. Compound I-48 was unstable in solution and converted to compound VI-1B which appeared as a mixture of I-48 and VI-1B in the ratio of 7:3. Compound VI-1B: UV (Acetonitrile/H$_2$O) λ$_{max}$ 235 (sh) nm; ESMS, m/z 585.2 (M+H)$^+$.

-continued

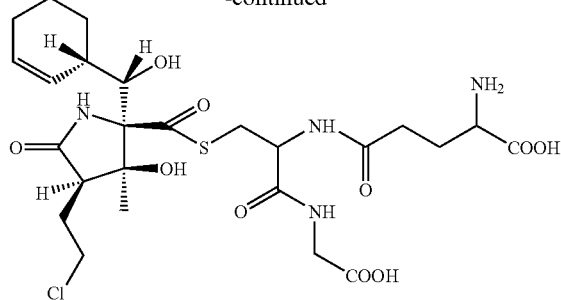

II-48

↓ -HCl

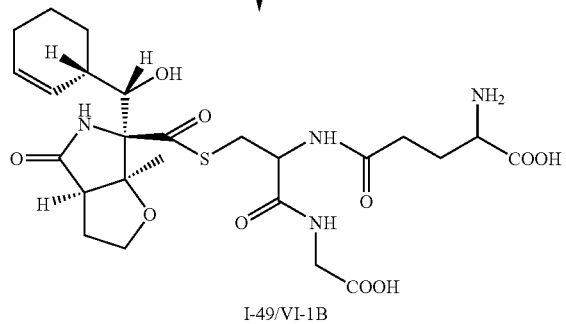

I-49/VI-1B

Example 32

Synthesis of the Compound of Formula I-50 and VI-1C from I-16

The compound of Formula I-16 (10 mg, 0.032 mmol) was dissolved in CH$_2$Cl$_2$ (9 ml) in scintillation vial (20 ml) to which triethylamine (26.5 μl, 0.192 mmol), N-Acetyl-L-Cysteine methyl ester (17 mg, 0.096 mmol) and a magnetic stir bar were added. The reaction mixture was stirred at room temperature for about 4 hours. The solvent was evaporated from the reaction mixture to yield the mixture of compounds of Formulae I-50 and VI-1C, which were further purified by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process. Compounds I-50 (2 mg) and VI-1C (0.2 mg) were eluted at 10.39 and 10.57 min, respectively as pure compounds. Compound I-50: UV (Acetonitrile/H$_2$O) λ$_{max}$ 230 (sh) nm; ESMS m/z 491.1 (M+H)$^+$ & 513.0 (M+Na)$^+$. Compound VI-1C: UV (Acetonitrile/H$_2$O) λ$_{max}$ 215 (sh) nm; ESMS m/z 455.1 (M+H)$^+$ & 577.0 (M+Na)$^+$

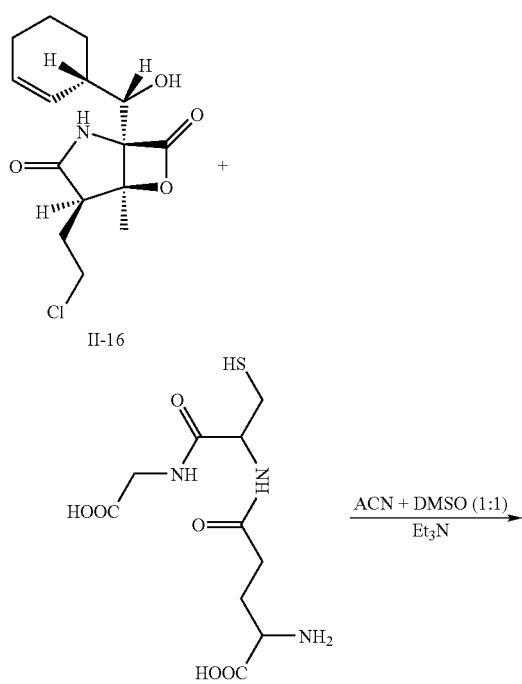

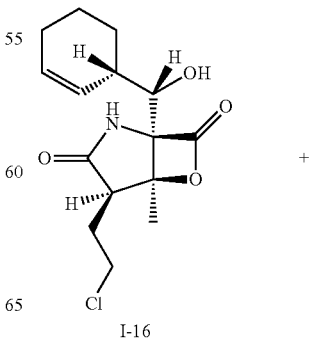

I-16

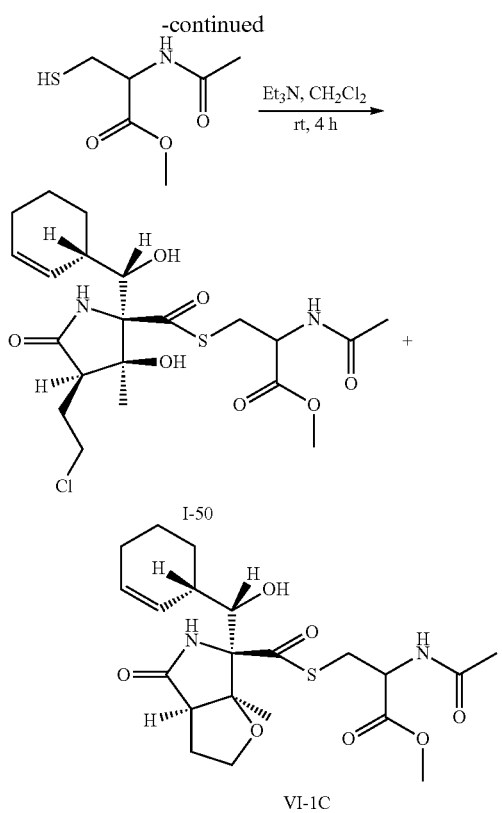

Example 33

Formulation to be Administered Orally or the Like

A mixture obtained by thoroughly blending 1 g of a compound obtained and purified by the method of the embodiment, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

Example 34

Salinosporamide a Inhibits DNA Synthesis and Induces Cytotoxicity of WM Cells

Figure 1B:
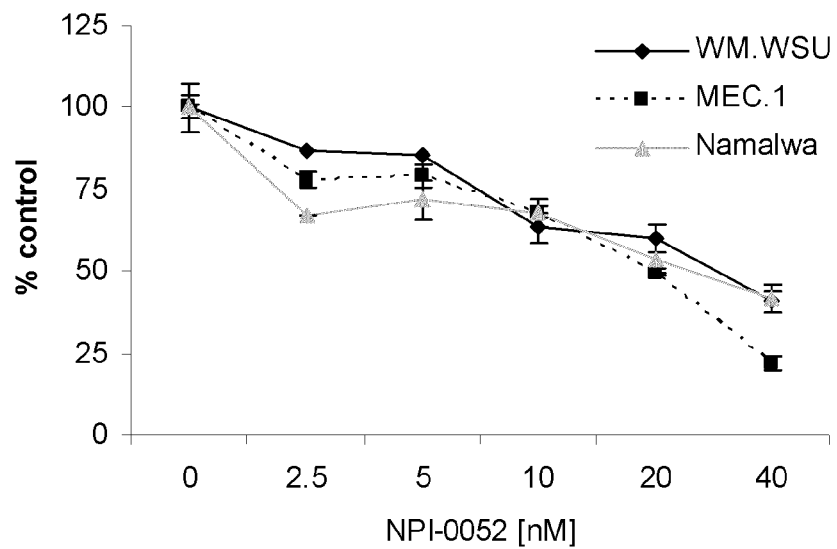
FIG. 1B is a graph showing thymidine uptake assay. Several IgM-secreting cell lines, WM-WSU (♦), MEC-1 (■), Namalwa were cultured with salinosporamide A (2.5-40 nM) for 48 hours.

WM and IgM-secreting cell lines were cultured for 48 hours in the presence of salinosporamide A (Formula I-16) (2.5-40 nM). As shown in FIG. 1A, salinosporamide A inhibited BCWM. 1 proliferation, as measured by [$^3$H]-thymidine uptake assay, with an $IC_{50}$ of 15 nM. salinosporamide A demonstrated similar activity on all cell lines tested, with $IC_{50}$ between 20 and 30 nM at 48 hours (FIG. 1B).

Figure 1C:
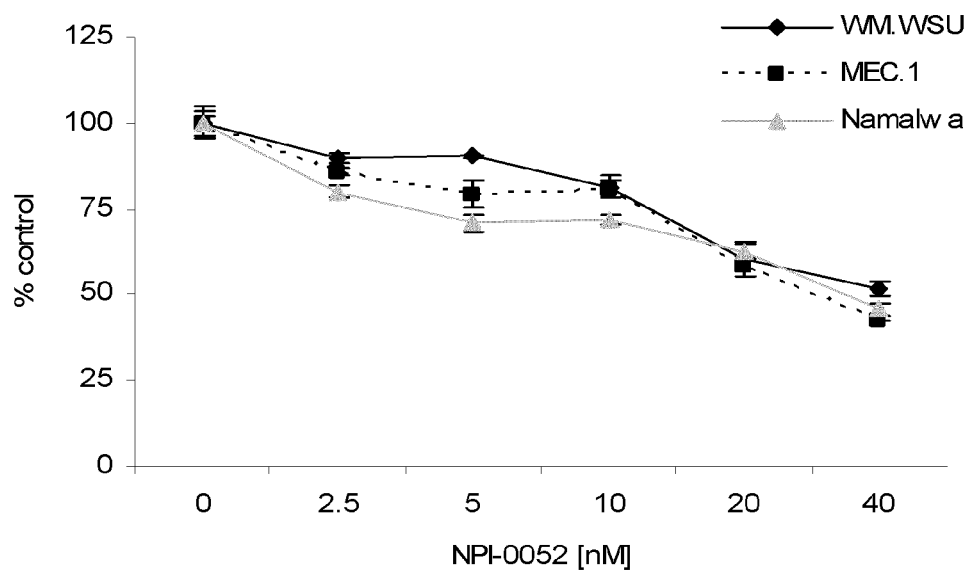
FIG. 1C is a graph showing several IgM secreting cell lines, WM-WSU, MEC-1, Namalwa were cultured with salinosporamide A for 48 hours. Cytotoxicity was assessed by MTT assay.
Figure 1D:
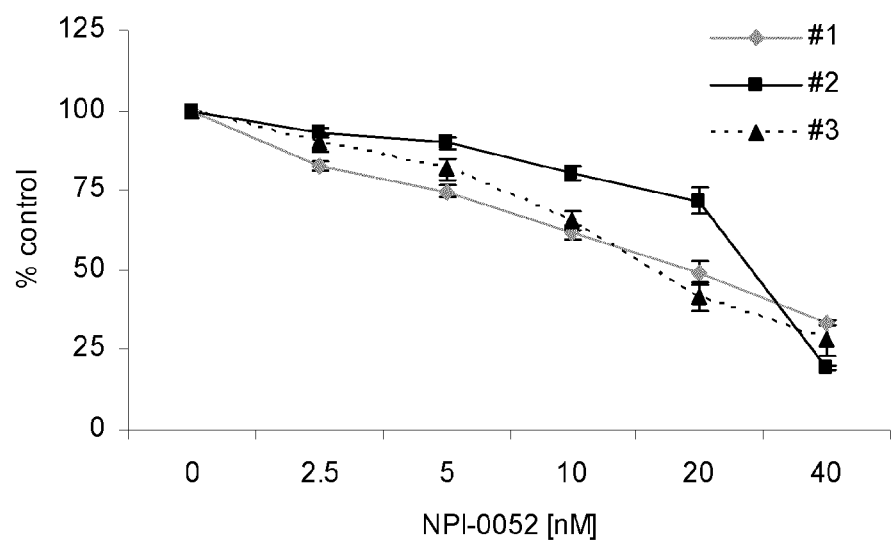
FIG. 1D is a graph showing freshly isolated bone marrow CD19+ tumor cells from 3 patients with WM were cultured with salinosporamide A (2.5-40 nM [E]; 2.5-80 nM [F]). Cytotoxicity was assessed by MTT assay.

The cytotoxic effect of salinosporamide A (2.5-40 nM) on cell lines and WM patient cells by MTT assay was studied. salinosporamide A decreased survival of BCWM.1 cells ($IC_{50}$, 18 nM; FIG. 1A) and other IgM-secreting cell lines ($IC_{50}$ 30-40 nM; FIG. 1C). Similarly, salinosporamide A induced cytotoxicity in primary CD19$^+$ cells isolated from three patients with WM ($IC_{50}$ 20-30 nM; FIG. 1D). In contrast, salinosporamide A had no cytotoxic effect on PBMCs from 3 healthy volunteers (data not shown). These results demonstrate that salinosporamide A triggers significant cytotoxicity in tumor cell lines and patient WM cells, without toxicity in normal PBMCs.

Example 35

Salinosporamide a Induces Apoptosis in WM Cells

Figure 1E:
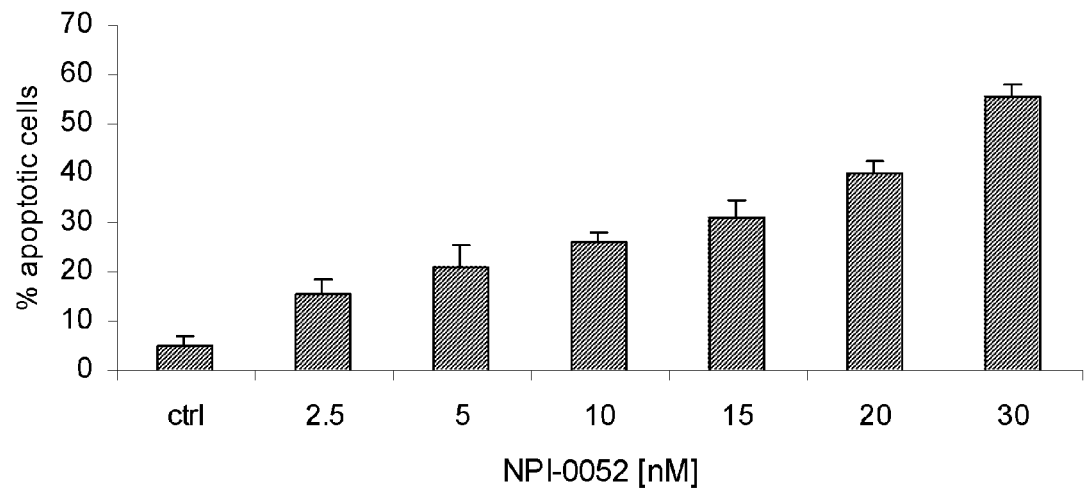
FIG. 1E is a graph showing BCWM. 1 cultured with salinosporamide A for 48 hours at doses that range from 2 to 30 nM and the percentage of cells undergoing apoptosis was studied by Apo2.7 staining.

The molecular mechanisms whereby salinosporamide A induces cytotoxicity in WM cells was examined. The results demonstrate that salinosporamide A induced dose-dependent apoptosis, as evidenced by Apo2.7 staining in flow cytometry analysis. The percentage of apoptotic BCWM.1 cells increased from 5% (untreated) to 21.2% and 40% after 48 hours of treatment with salinosporamide A 5 nM and 20 nM respectively (FIG. 1E). Similar data were obtained on other IgM secreting cell lines (data not shown).

Figure 1F:
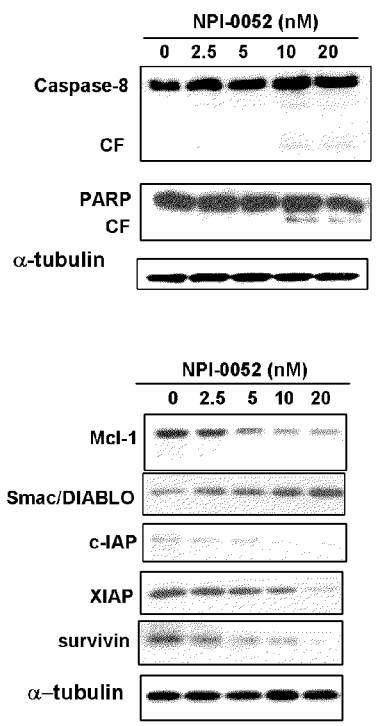
FIG. 1F is a western blot showing BCWM.1 cells cultured with salinosporamide A (2.5-20 nM) for 12 hours. Whole cell lysates were subjected to Western blotting using anti-caspase 8, -PARP, -Mcl-1, -Smac/DIABLO, -cIAP, -XIAP, -survivin, and -α-tubulin antibodies.

Mechanisms whereby salinosporamide A induces apoptosis in WM was determined, and it was demonstrated that salinosporamide A induced caspase-8 and PARP cleavage in a dose-dependent manner (FIG. 1F), without affecting caspase-3 and -9 (data not shown). Moreover salinosporamide A induced down-modulation of the anti-apoptotic protein Mcl-1, with an increased release of the second mitochondria-derived activator of caspases (Smac/DIABLO) from the mitochondria to the cytosol (FIG. 1F). It has been reported that Smac/DIABLO can abrogate the protective effects of inhibitors of apoptosis proteins (IAPs), such as X-linked inhibitor of apoptosis (XIAP).[26] Therefore, BCWM.1 cells were treated with salinosporamide A (2.5-20 Nm) for 12 hours and demonstrated that salinosporamide A down-regulated the expression of XIAP in a dose-dependent manner, accompanied by an inhibition of other IAPs members, such as c-IAP and survivin (FIG. 1F).

Example 36

Figure 2A:
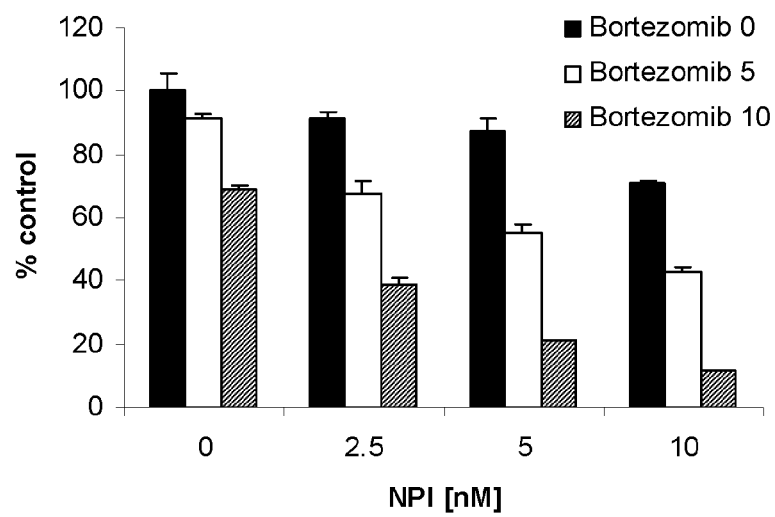
FIG. 2A is a graph showing BCWM.1 cells cultured with salinosporamide A (2.5, 5 and 10 nM) for 48 hours, in the presence or absence of bortezomib (5 and 10 nM). Cytotoxicity was assessed by MTT assay.
Figure 2B:
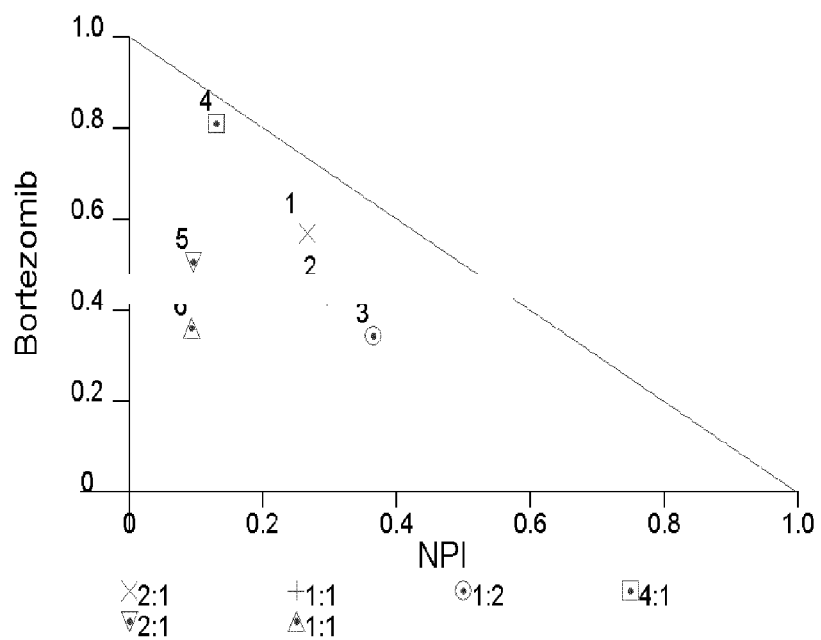
FIG. 2B is a graph showing a representative isobologram of salinosporamide A associated to bortezomib with the CalcuSyn software demonstrating synergy for the combination.
Figure 2C:
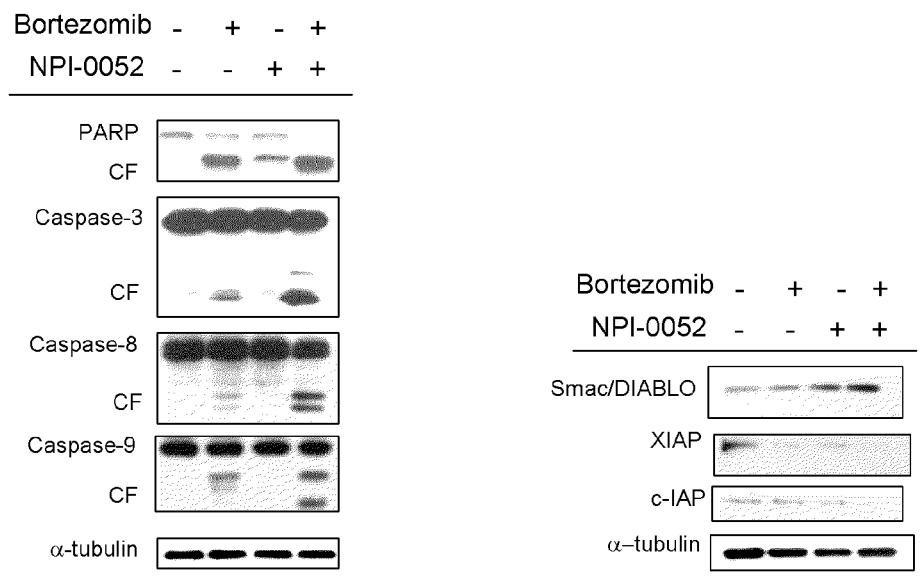
FIG. 2C is a chart showing indexes (C.I.) and fractions affected (FA) of the combinations of salinosporamide A and bortezomib. All experiments were repeated in triplicate.

Salinosporamide A and Bortezomib Synergistically Induce Cytotoxicity of WM Cells Two proteasome inhibitors, salinosporamide A and bortezomib, were investigated to determine whether the combination could be synergistic in inducing cytotoxicity in WM cells. BCWM.1 cells were cultured with salinosporamide A (2.5-10 nM) for 48 hours, in the presence or absence of bortezomib (5-10 nM). salinosporamide A showed a significant cytotoxic effect when combined with bortezomib in BCWM.1 cells, as demonstrated using MTT assay at 48 hours (FIG. 2A). salinosporamide A (5 nM) induced cytotoxicity in 12.4% of BCWM.1 cells, which was increased to 39.8% and 69.4% in the presence of bortezomib at 5 nM (Combination Index, CI: 0.72) and 10 nM (CI: 0.6), respectively, indicating synergism. Isobologram analysis, fractions affected and the combination indexes for each of these combinations are summarized in FIG. 2B-C. Similar data were observed on IgM secreting cell lines and primary CD19$^+$ cells (data not shown).

Figure 2D:
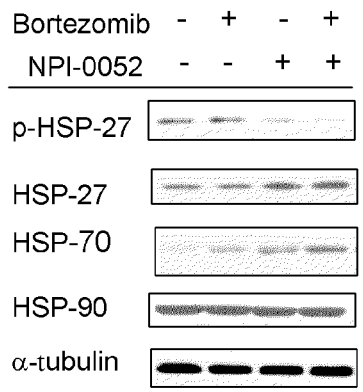
FIG. 2D is a picture showing BCWM.1 cultured with salinosporamide A (10 nM) in presence or absence of bortezomib (10 nM) for 12 hours. Whole cell lysates were subjected to Western blotting using anti-caspase-8, -9, -3, -PARP, -Smac/DIABLO, -cIAP, -XIAP, -survivin, -p-HSP27, -HSP27, -HSP70, -HSP90 and α-tubulin antibodies.

To better define the mechanisms of salinosporamide A/bortezomib-induced cytotoxicity, the effect of salinosporamide A (10 nM), either alone or in combination with bortezomib 10 nM, on BCWM.1 cells using immunoblotting after 12 hours treatment was investigated. It was demonstrated that PARP cleavage was significantly higher using the combination compared to the effect of each agent alone. To further dissect whether apoptosis is mediated through the intrinsic or extrinsic pathways, the effect of salinosporamide A, bortezomib and the combination on caspases-3, 8 and 9 was investigated. As shown in FIG. 2D, it was demonstrated that single agent salinosporamide A induced mild capsase-8 cleavage without affecting caspase-3 and 9 cleavage, while bortezomib induced-9 and -3 cleavage, while the combination of salinosporamide A and bortezomib induced significant caspase-3, -8 and -9 cleavage.

In addition, the effect of bortezomib and salinosporamide A on Smac and XIAP was investigated and as shown in FIG. 2D, it was demonstrated that the combination of the two proteasome inhibitors induced higher release of Smac/DIABLO and a significant decrease of XIAP, more than the effect of each agent alone. Similarly, it was demonstrated that the IAP member, c-IAP was strongly downregulated by the combination versus single agent treatment (FIG. 2D). In addition, it was shown that salinosporamide A down-regulates HSP-27 phosphorylation which in turn leads to increase in the release of Smac/DIABLO from the mitochondria and the induction of caspase-9 cleavage. In parallel it was shown that an upregulation of HSP70, while HSP-90 expression was not modulated (FIG. 2D).

Example 37

Figure 3A:
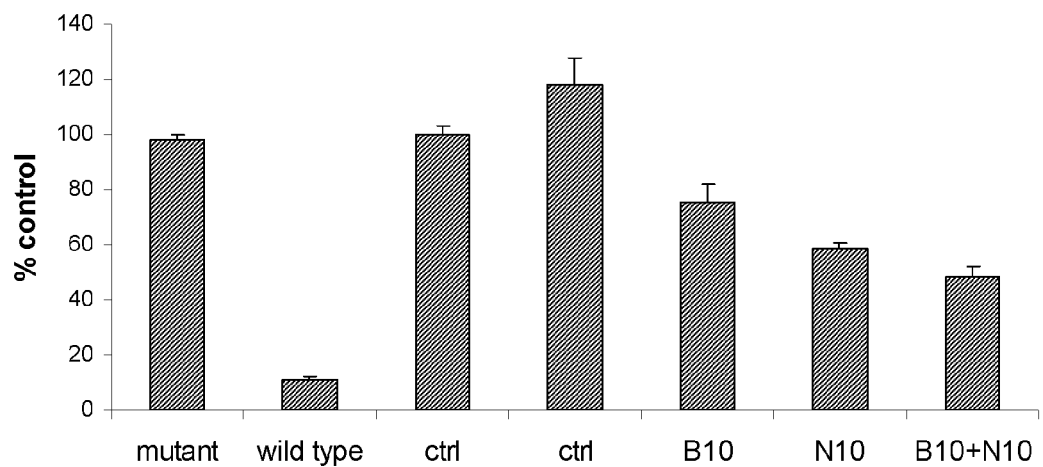
FIG. 3A is a graph showing BCWM.1 cells cultured with either salinosporamide A (10 nM), bortezomib (10 nM), or the combination for 4 hours, then human TNF-α (10 ng/mL) was added for the last 20 minutes. NF-κBp65 transcription factor-binding to its consensus sequence on the plate-bound oligonucleotide was studied from nuclear extract. Wild type and mutant are wild type and mutated consensus competitor oligonucleotides, respectively. All results represent means (±sd) of triplicate experiments.
Figure 3B:
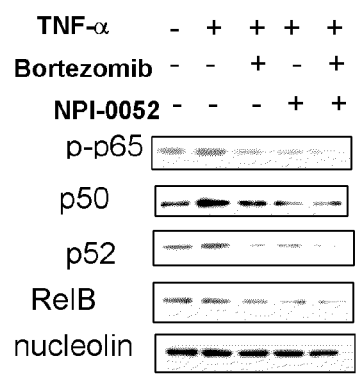
FIG. 3B is a picture showing BCWM.1 cells cultured with either salinosporamide A (10 nM), bortezomib (10 nM), or the combination for 4 hours, and TNF-α (10 ng/mL) was added for the last 20 minutes. Cytoplasmic and nuclear extracts were subjected to western blotting using anti-p-NF-κBp65, -NF-κBp50, -NF-κBp52 IkBα, -RelB, -p-IκB, -IκB, -nucleolin and -α-tubulin antibodies.
Figure 3C:
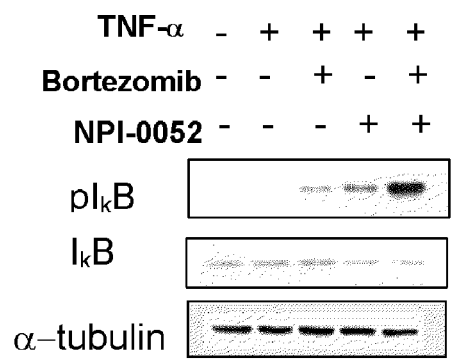
FIG. 3C is a picture showing BCWM.1 cells cultured with either salinosporamide A (10 nM), bortezomib (10 nm), or the combination for 4 hours, and TNF-α (10 ng/mL) was added for the last 20 minutes. Cytoplasmic and nuclear extracts were subjected to western blotting using anti-p-NF-κBp65, -NF-κBp50, -NF-κBp52 IkBα, -RelB, -p-IκB, -IκB, -nucleolin and -α-tubulin antibodies.
Figure 3D:
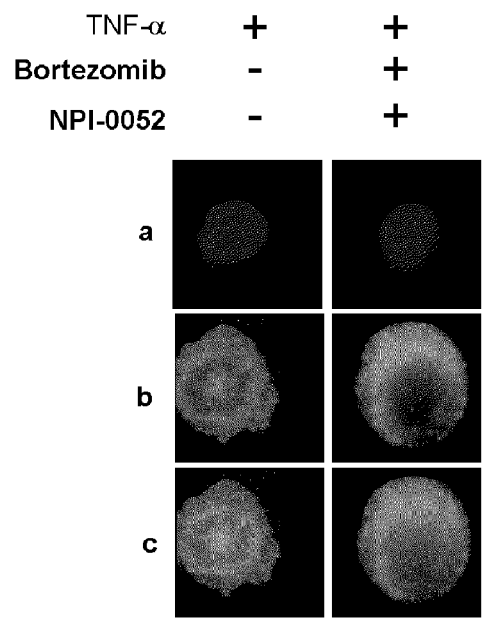
FIG. 3D is a picture showing BCWM.1 cells cultured with salinosporamide A (10 nM) and bortezomib (10 nM) for 4 hours, or control medium, and TNF-α (10 ng/mL) was added for the last 20 minutes. Immunocytochemical analysis was assessed as described in Materials and Methods.

Salinosporamide A and Bortezomib Synergistically Inhibit NF-κB Activation in WM Cells The effect of salinosporamide A either alone or in combination with bortezomib on the NF-κBp65 DNA binding activity was investigated, studying nuclear extracts from treated cells using the Active Motif assay. It was shown that TNF-α treatment induced NF-κB recruitment to the nucleus in BCWM.1 cells, which was inhibited by salinosporamide A more than bortezomib, and more significantly by the combination of the two proteasome inhibitors (FIG. 3A). In addition, immunoblotting from nuclear extracts demonstrated that p65 phosphorylation and p50NF-κB expression were inhibited by salinosporamide A, either alone or in combination with bortezomib, more than bortezomib used as single agent (FIG. 3B). Phospho-p65 translocation from the cytoplasmic compartment to the nucleus was inhibited by the combination of bortezomib and salinosporamide A, resulting in a significant increase in p-p65 expression in the cytoplasmic compartment as shown by immunofluorescence (FIG. 3D). Immunoblotting from nuclear extracts showed that two proteasome inhibitors used in combination inhibited the expression of p52 and RelB, which are mostly activated through the non-canonical pathway (FIG. 3B).[28] Moreover, each agent alone, and more significantly their combination up-regulated the phosphorylation of the inhibitor protein IκB, as shown in FIG. 3C. Taken together, these data demonstrate that the combination of the two proteasome inhibitors regulate both canonical and non-canonical pathways of NF-κB in WM.

Example 38

Figure 4A:
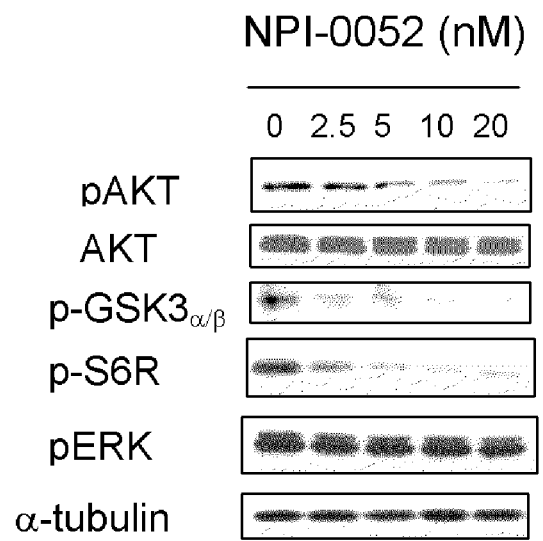
FIG. 4A is a picture showing BCWM.1 cultured with salinosporamide A (2.5-20 nM) for 6 hours. Whole cell lysate were subjected to Western blotting using anti-p-Akt, -Akt, -p-GSK3α/β, -p-S6R, -p-ERK, and -α-tubulin antibodies.
Figure 4B:
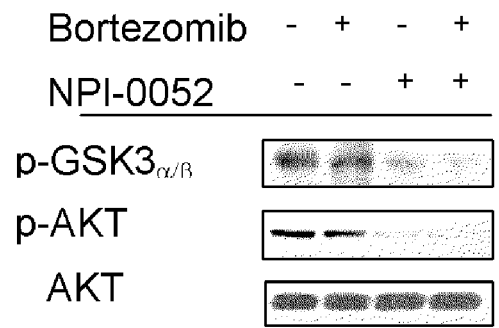
FIG. 4B is a picture showing In vitro Akt kinase assay. BCWM.1 cells cultured with control media or salinosporamide A (2.5-20 nM) for 6 hours. Whole cell lysates were immunoprecipitated with anti-Akt antibody. Then the immunoprecipitate was washed and subjected to in vitro kinase assay according to manufacturer's protocol. Western blotting used anti-p-GSK3α/β and anti-Akt antibodies.
Figure 4C:
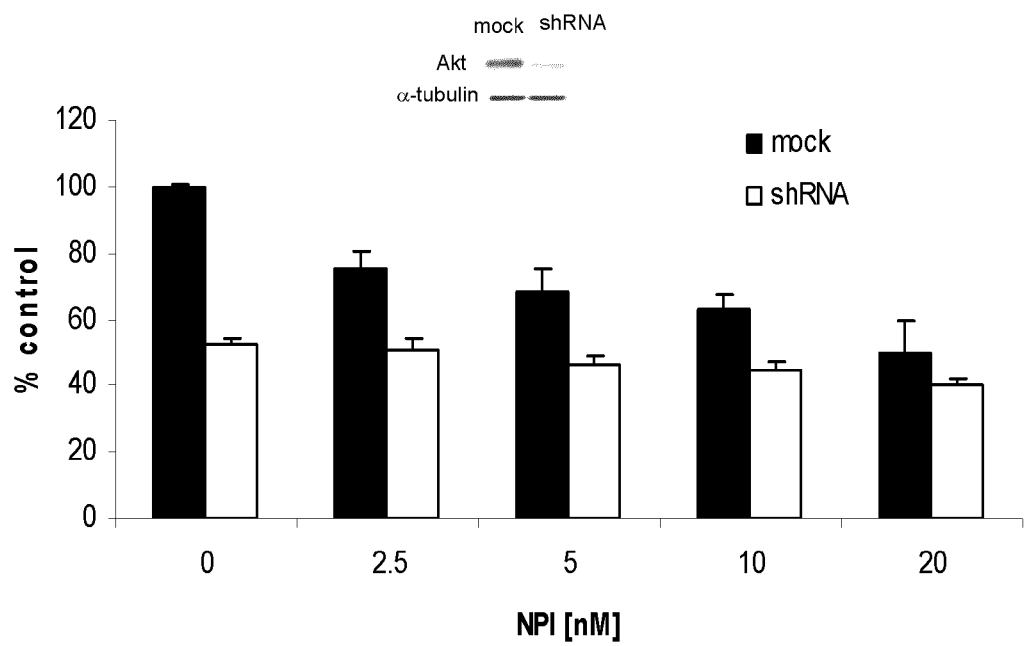
FIG. 4C is a graph showing BCWM.1 cells transduced with Akt shRNA for 48 hours. Mock: control plasmid. BCWM.1 transfected cells or BCWM.1 control cells were treated with salinosporamide A (2.5-20 nM) for 48 hours. Cytotoxicity was assessed by MTT assay. Whole cell lysates were subjected to western blotting using anti-p-Akt, -Akt, and α-tubulin antibodies.

Salinosporamide A and Bortezomib Synergistically Inhibit PI3K/ATK Pathway in WM Cells Whether salinosporamide A could affect PI3K/Akt signaling pathway in WM cells was investigated. BCWM.1 cells were treated with increasing doses of salinosporamide A (2.5-20 nM) for 6 hours. As shown in FIG. 4A, salinosporamide A inhibited phosphorylation of Akt (ser473), and downstream $GSK3_{\alpha/\beta}$ and ribosomal protein S6 in a dose dependent manner, with no activity on the phosphorylation of the MAP kinase ERK1/2 (thr202/tyr204). The effect of salinosporamide A (10 nM), alone or combined with bortezomib (10 nM), on Akt kinase activity, using an in vitro Akt kinase assay was then investigated. It was shown that salinosporamide A decreased phosphorylation of $GSK3\alpha/\beta$ fusion protein, while bortezomib did not modulate Akt phosphorylation. The combination of salinosporamide A and bortezomib showed significant inhibition of Akt activity, indicating a possible mechanism of synergy where salinosporamide A overcomes Akt-dependent bortezomib resistance (FIG. 4B). To further validate the role of the Akt pathway in salinosporamide A-dependent cytotoxicity, an Akt knockdown BCWM.1 cell line established using lentivirus infection was used and it was demonstrated that in the absence of Akt, the cytotoxic effect of salinosporamide A was abrogated (FIG. 4C), indicating that Akt plays an essential role in the cytotoxic activity of salinosporamide A and that this could be an important differential effect between the two proteasome inhibitors and a mechanism of synergy between them in WM.

Example 39

Figure 4D:
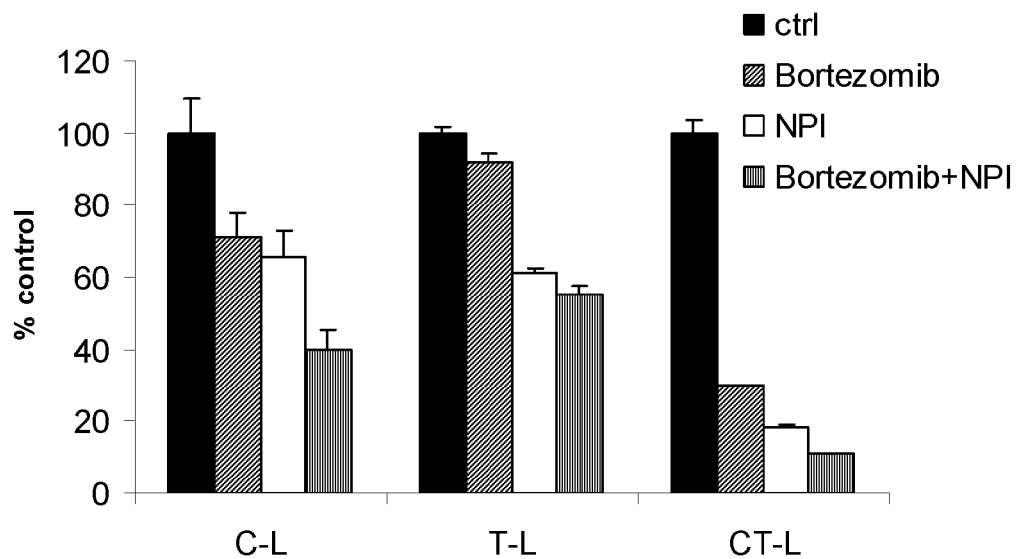
FIG. 4D is a graph showing BCWM.1 cells or primary CD19+ tumor cells from 2 patients with WM (FIG. 4E i, ii, iii) were incubated for 4 hours in the presence of diluent or 10 nM salinosporamide A, bortezomib 10 nM, or bortezomib+salinosporamide A. The chymotrypsin-like (CT-L), trypsin-like (T-L), and caspase-like (C-L) activity of the 20S proteasome of BCWM.1 was determined by measurement of fluorescence generated from the cleavage of the fluorogenic substrates suc-LLVY-amc, boc-LRR-amc, and z-LLE-amc, respectively.

Salinosporamide A Inhibits the Three Proteolytic Activities within the 20S Proteasome Cells were treated with salinosporamide A (10 nM) either alone or in combination with bortezomib (10 nm), for 4 hours, and the chymotrypsin-like (CT-L), caspase-like (CL) and trypsin-like (T-L) activities were measured using distinct fluorogenic peptides specific for each enzymatic activity.[22] As shown in FIG. 4D, bortezomib induced 29%, 5% and 69% reduction of the C-L, T-L and CT-L activities, respectively; compared to salinosporamide A which induced 34.3%, 38.7% and 81% reduction of the C-L, T-L and CT-L activities, respectively. Interestingly, the inhibition of the C-L activity significantly increased to 60% when salinosporamide A and bortezomib were used in combination (FIG. 4D). Similar data were obtained on $CD19^+$ primary cells (FIG. 4Ei-Ii).

Example 40

The Combination of Salinosporamide A and Bortezomib Overcomes Resistance Induced by the Bone Marrow Microenvironment and IL-6

Figure 5A:
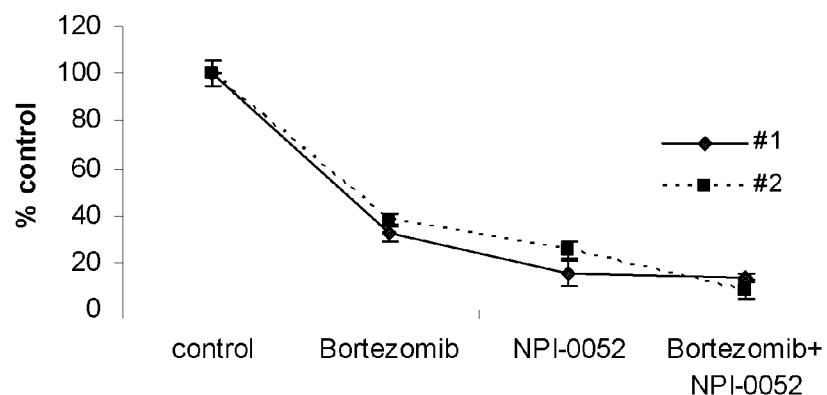
FIG. 5A is a graph showing BCWM.1 cells cultured with control media, and with salinosporamide A (2.5-20 nM), with and without bortezomib (10 nM) for 48 hours, in the presence or absence of BMSCs. Cell proliferation was assessed using [$^3$H]-thymidine uptake assay. All data represent mean (±sd) of triplicate experiment.
Figure 5A:
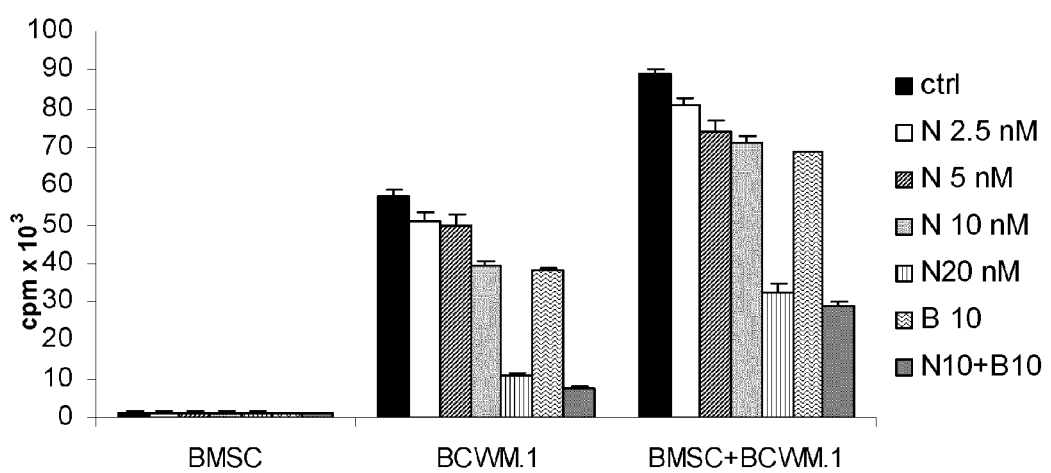

Whether salinosporamide A, alone or in combination with bortezomib, inhibits WM cells growth in the context of the BM milieu was investigated. BCWM.1 cells were cultured with salinosporamide A (2.5-20 nM) and/or bortezomib (10 nM) in the presence or absence of BMSCs, for 48 hours. The viability of BMSCs, assessed by MTT was not affected by salinosporamide A treatment (data not shown). Using $[^3H]$-TdR uptake assay, adherence of BCWM.1 cells to BMSCs triggered an increase of 55% in proliferation, which was inhibited by salinosporamide A in a dose-dependent manner. This effect was significantly enhanced by the combination with bortezomib (FIG. 5A), confirming that the combination of the two proteasome inhibitors enhanced the antitumor activity of each drug used as a single agent, even in presence of BMSCs.

Figure 5B:
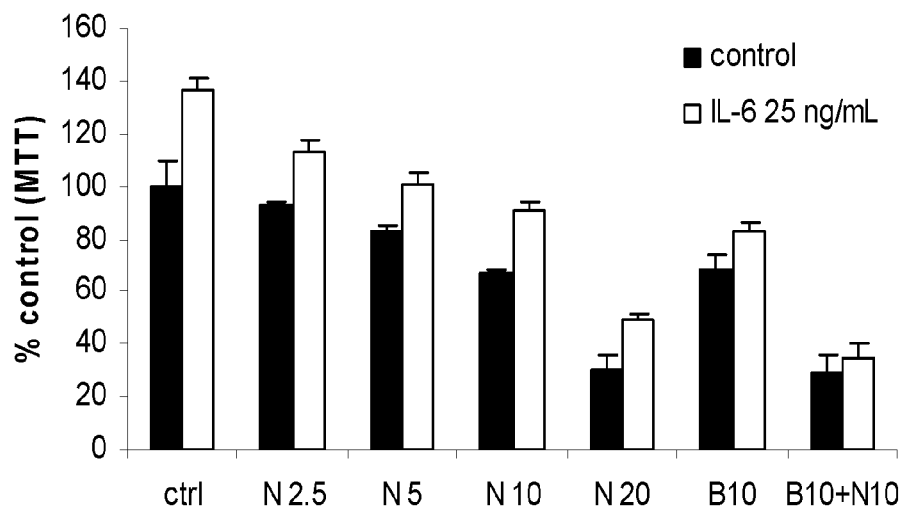
FIG. 5B is a graph showing BCWM.1 cultured with control media or salinosporamide A (2.5-20 nM), with and without bortezomib (10 nM) for 48 hours, in presence or absence of IL-6 (25 ng/mL) (10 µM). Proliferation was assessed by thymidine uptake assay.
Figure 5C:
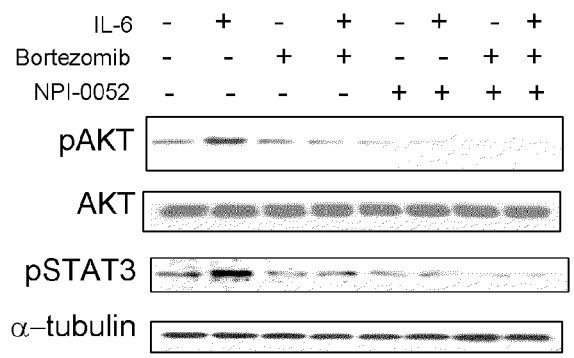
FIG. 5C is a western blot showing BCWM.1 cells cultured with control media or salinosporamide A (10 nM) with and without bortezomib (10 nM) for 8 hours. Cells were then stimulated with IL-6 (25 ng/mL) for 10 minutes. Whole cell lysates were subjected to western blotting using anti-p-AKT, anti-AKT, anti-p-STAT3 and anti-α-tubulin.
Figure 5D:
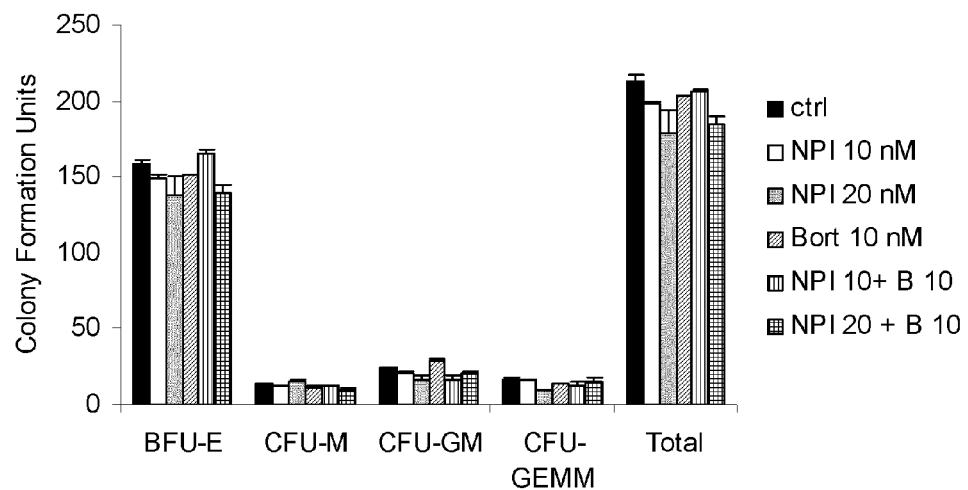
FIG. 5D is a graph showing colony-forming cell assay. Negative fraction after CD19$^+$ selection of bone marrow mononuclear cells was cultured using methylcellulose semisolid technique in absence or presence of salinosporamide A (10 nM, 20 nM) either alone or in combination with bortezomib 10 nM, and BFU-E, CFU-GM, CFU-M and CFU-GEMM were counted at day 14$^{th}$. All experiments have been done in triplicate.

The effect of the two proteasome inhibitors on cytotoxicity of WM cells in the presence of IL-6 was also investigated. Whether the addition of recombinant IL-6 (25 ng/mL) can overcome the cytotoxic effect of salinosporamide A and bortezomib on WM cells was tested. As shown in FIG. 5B, IL-6 induced proliferation of BCWM.1 cell, and the addition of salinosporamide A (2.5-20 nM), bortezomib (10 nM), or the combination inhibited IL-6-induced proliferation of BCWM.1 cells, indicating that salinosporamide A, alone or more significantly in combination with bortezomib, overcomes resistance induced by IL-6. In addition, IL-6 induced phosphorylation of Akt and STAT-3. salinosporamide A and bortezomib inhibited IL-6-triggered Akt and STAT-3 phosphorylation, which were more significantly down-regulated with the combination of salinosporamide A and bortezomib (FIG. 5C). Whether the two proteasome inhibitors, used as single agent or in combination, could also target non-malignant hematopoietic cells was investigated. It was found that salinosporamide A (10 nM, 20 nM), bortezomib (10 nM) and the combination did not affect the growth of BM hematopoietic progenitor cells as shown using colony-formation assay (FIG. 5D).

Example 41

Figure 6A:
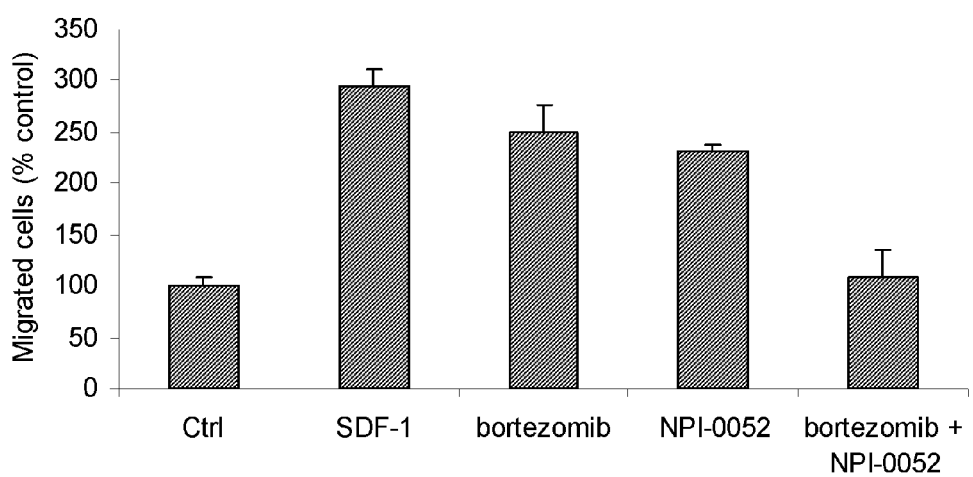
FIG. 6A is a graph showing Transwell migration assay showing inhibition of migration of BCWM.1 in the presence of salinosporamide A (2.5-20 nM), bortezomib (10 nM), or salinosporamide A (10 nM) in combination with bortezomib (10 nM). SDF-1 30 nM was placed in the lower chambers and induced migration as compared to control with no SDF-1 (Ctrl, control). SDF-1 was placed in the lower chambers of the salinosporamide A/bortezomib-treated wells.
Figure 6B:
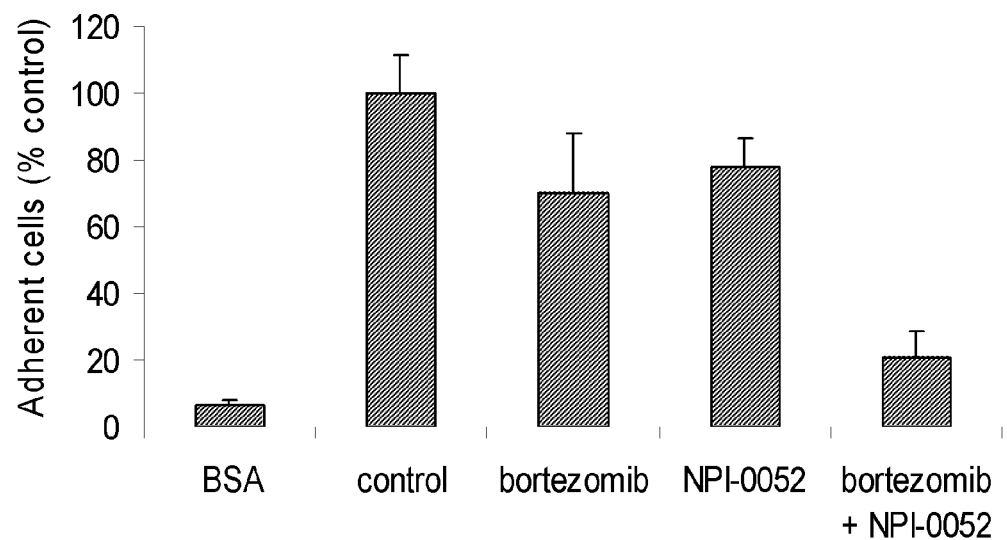
FIG. 6B is a graph showing an adhesion assay with BCWM.1 cells in the presence or absence of salinosporamide A (10 nM), either alone or in combination with bortezomib (10 nM). BCWM.1 cells demonstrated increased adhesion in fibronectin-coated wells (control) as compared to BSA-coated wells (BSA, bovine serum albumin). All data represent mean (±sd) of triplicate experiments.
Figure 6C:
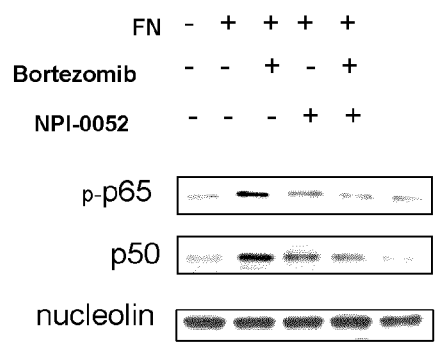
FIG. 6C is a picture showing BCWM.1 cells cultured with control media or salinosporamide A (10 nM) with and without bortezomib (10 nM) for 4 hours, in presence or absence of fibronectin (FN). Nuclear extracts were subjected to western blotting using anti-p-p65, -p50, and -nucleolin antibodies.
Figure 6D:
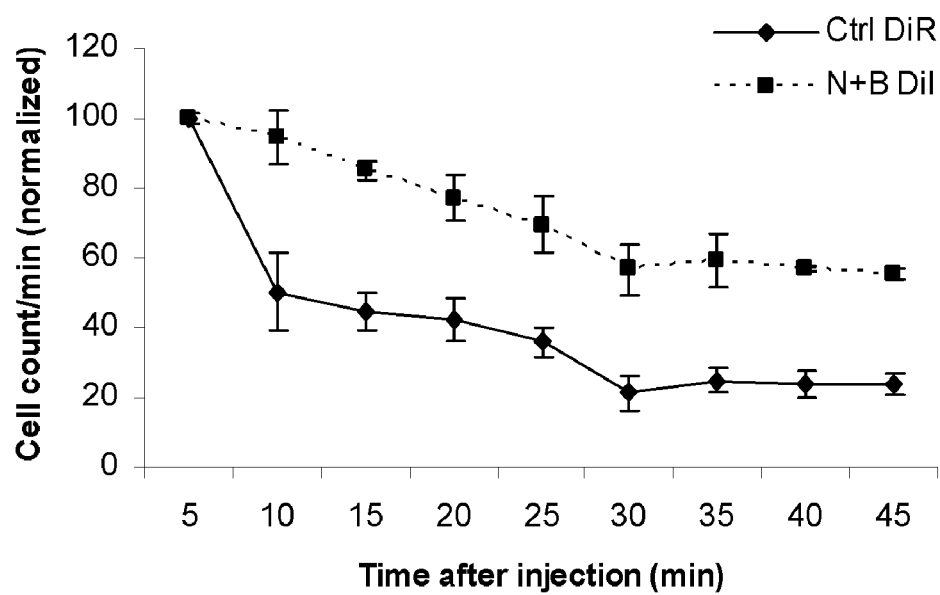
FIG. 6D is a graph showing in vivo flow cytometry. DiI-labeled treated cells and DiR-labeled untreated cells were injected in the tail vein of 2 BALB/c mice. Cells were counted every 5 min for 45 minutes as described in Material and Methods.

Salinosporamide A and Bortezomib Inhibit Migration and Adhesion of WM Cells In Vitro and Homing In Vivo It was demonstrated that stromal derived factor-1 (SDF-1), one of the important regulators of migration in B-cells, induced migration in BCWM.1 cells at 30 nM SDF-1. To study the effect of salinosporamide A on the migration of WM cells, BCWM.1 cells were incubated with salinosporamide A (10 nM), either alone or in combination with bortezomib (10 nM), for 4 hours (these doses and duration of incubation did not induce apoptosis in WM cells as confirmed by trypan blue and Apo2.7 staining by flow cytometry, data not shown). Cells were then subjected to migration as previously described in Alsayed Y, Ngo H, Runnels J., et al. Mechanisms of regulation of CXCR4/SDF-1 (CXCL12)-dependent migration and homing in multiple myeloma. Blood. 2007; 109:2708-2717, which is incorporated by reference in its entirety. salinosporamide A slightly inhibited WM cells migration towards SDF-1, which was significantly inhibited when salinosporamide A was used in combination with bortezomib. In combination with bortezomib induced significant inhibition of BCWM.1 cells migration (FIG. 6A).

salinosporamide A induced significant inhibition of adhesion to fibronectin when used in combination with bortezomib (FIG. 6B). Therefore, the effect of salinosporamide A and bortezomib on NF-κB activity in the presence or absence of fibronectin was examined. As shown in FIG. 6C, FN induced a significant increase in p65 phosphorylation and p50NF-κB expression, which were inhibited by salinosporamide A, bortezomib, and more significantly by the two drugs in combination.

DI-labeled BCWM.1 cells treated with salinosporamide A (10 nM, 4 hours), alone or in combination with bortezomib (5 nM), or DiR-labeled untreated BCWM.1 cells used as control were injected in the tail vein of BALB/c mice, followed by in vivo flow cytometry every 5 minutes for 45 minutes after injection. Neither salinosporamide A nor bortezomib used as single agents significantly inhibited homing of WM cells to the bone marrow, as demonstrated by a rapid decrease of circulating BCWM.1 cells which was observed in the untreated cells as well as on cells treated with salinosporamide A or bortezomib (data not shown). It was demonstrated that pretreatment of BCWM.1 with salinosporamide A in combination with bortezomib resulted in a significant inhibition of homing with a decrease of 45% of cells in the circulation at 45 minutes compared to a decreased of 77% obtained in the untreated cells, suggesting that when the two proteasome inhibitors were used together there is an inhibition in the homing of WM cells to the bone marrow (FIG. 5D).

The examples described above are set forth solely to assist in the understanding of the embodiments. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications can be made to the embodiments disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed can be resorted to by those skilled in the art, and that such modifications and variations are considered to be falling within the scope of the embodiments of the invention.

What is claimed is:

1. A method of treating resistant Waldenstrom's Macroglobulinemia comprising administering to an animal a compound having the structure of Formula I, or a pharmaceutically acceptable salt or pro-drug ester thereof:

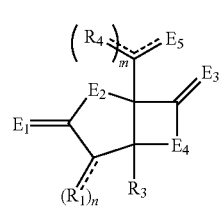

Formula I wherein $R_1$, $R_3$, and $R_4$ are separately selected from the group consisting of a hydrogen, a halogen, a mono-substituted, a poly-substituted or an unsubstituted moiety of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;
wherein m is equal to 1 or 2;
wherein n is equal to 1 or 2;

wherein each of $E_1$, $E_2$, $E_3$ and $E_4$ is a substituted or unsubstituted heteroatom; and wherein $E_5$ is selected from the group consisting of OH, O, $OR_{10}$, S, $SR_{11}$, $SO_2R_{11}$, NH, $NH_2$, NOH, NHOH, $NR_{12}$, and $NHOR_{13}$.

2. The method of claim 1, wherein $R_{10-13}$ are selected from the group consisting of hydrogen and a substituted or unsubstituted moiety of any of the following: $C_{1-24}$ alkyl, aryl, and heteroaryl.

3. The method of claim 1, wherein the animal is a mammal.

4. The method of claim 1, wherein the animal is a human.

5. The method of claim 1, wherein the animal is a rodent.

6. The method of claim 1, further comprising co-administering a chemotherapeutic agent.

7. The method of claim 6, wherein the chemotherapeutic agent is selected from the group consisting of Adriamycin, Doxorubicin, 5-Fluorouracil, Cytosine arabinoside ("Ara-C"), Cyclophosphamide, Thiotepa, Busulfan, Cytoxan, Taxol, Taxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins, Melphalan, tamoxifen and onapristone.

8. The method of claim 6, wherein the chemotherapeutic agent is a proteasome inhibitor.

9. The method of claim 8, wherein the proteasome inhibitor is bortezomib.

10. The method of claim 8, wherein the proteasome inhibitor is carfilzomib.

11. The method of claim 6, wherein the chemotherapeutic agent is a histone deacetylase inhibitor.

12. The method of claim 11, wherein the compound having the structure of Formula I and the histone deacetylase inhibitor work in a synergistic manner to treat Waldenstrom's Macroglobulinemia.

13. The method of claim 11, wherein the histone deacetylase inhibitor is selected from the group consisting of MS-275, APHA compound 8, Apicidin, (−)-Depudecin, sodium butyrate, Scriptaid, Sirtinol, Trichostatin A, Valproic acid (VPA) and Vorinostat (suberoylanilide hydroxamic acid (SAHA)).

14. The method of claim 6, wherein the chemotherapeutic agent is a vascular disrupting agent.

15. The method of claim 14, wherein the vascular disrupting agent is NPI-2358.

16. The method of claim 14, wherein the vascular disrupting agent is combratostatin CA4P.

17. A method of treating resistant Waldenstrom's Macroglobulinemia comprising administering to an animal a compound having the structure of Formula I-15, or a pharmaceutically acceptable salt or pro-drug ester thereof:

I-15

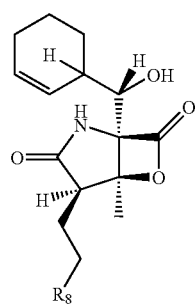

wherein $R_8$ is hydrogen, fluorine, chlorine, bromine or iodine.

18. The method of claim 17, wherein the compound is:

I-16

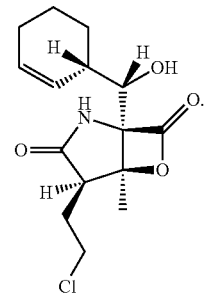

19. The method of claim 17, wherein the animal is a mammal.

20. The method of claim 17, wherein the animal is a human.

21. The method of claim 17, wherein the animal is a rodent.

22. The method of claim 17, further comprising co-administering a chemotherapeutic agent.

23. The method of claim 22, wherein the chemotherapeutic agent is selected from the group consisting of Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins, Melphalan, tamoxifen and onapristone.

24. The method of claim 22, wherein the chemotherapeutic agent is a proteasome inhibitor.

25. The method of claim 24, wherein the proteasome inhibitor is bortezomib.

26. The method of claim 24, wherein the proteasome inhibitor is carfilzomib.

27. The method of claim 22, wherein the chemotherapeutic agent is a histone deacetylase inhibitor.

28. The method of claim 27, wherein the compound having the structure of Formula I and the histone deacetylase inhibitor work in a synergistic manner to treat Waldenstrom's Macroglobulinemia.

29. The method of claim 27, wherein the histone deacetylase inhibitor is selected from the group consisting of MS-275, APHA compound 8, Apicidin, (−)-Depudecin, sodium butyrate, Scriptaid, Sirtinol, Trichostatin A, Valproic acid (VPA) and Vorinostat (suberoylanilide hydroxamic acid (SAHA)).

30. The method of claim 22, wherein the chemotherapeutic agent is a vascular disrupting agent.

31. The method of claim 30, wherein the vascular disrupting agent is NPI-2358.

32. The method of claim 30, wherein the vascular disrupting agent is combratostatin CA4P.

33. A method of inhibiting the growth of a resistant Waldenstrom's Macroglobulinemia cell comprising contacting the cell with a compound having the structure of Formula I, or a pharmaceutically acceptable salt or pro-drug ester thereof:

Formula I

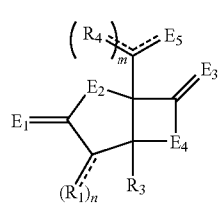

wherein $R_1$, $R_3$, and $R_4$ are separately selected from the group consisting of a hydrogen, a halogen, a mono-substituted, a poly-substituted or an unsubstituted moiety of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;
wherein m is equal to 1 or 2;
wherein n is equal to 1 or 2;
wherein each of $E_1$, $E_2$, $E_3$ and $E_4$ is a substituted or unsubstituted heteroatom; and
wherein $E_5$ is selected from the group consisting of OH, O, $OR_{10}$, S, $SR_{11}$, $SO_2R_{11}$, NH, $NH_2$, NOH, NHOH, $NR_{12}$, and $NHOR_{13}$.

34. A method of inhibiting the growth of a resistant Waldenstrom's Macroglobulinemia cell comprising contacting the cell with a compound having the structure of Formula I-15, or a pharmaceutically acceptable salt or pro-drug ester thereof:

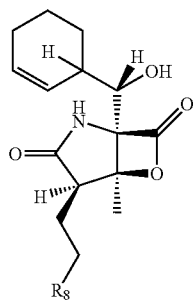

wherein $R_8$ is hydrogen, fluorine, chlorine, bromine or iodine.

35. The method of claim 34, wherein the compound is:

II-16

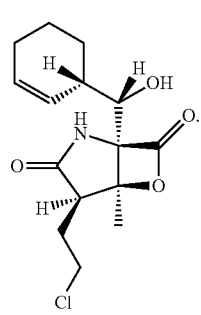

36. A method of inducing apoptosis of a resistant Waldenstrom's Macroglobulinemia cell comprising contacting the cell with a compound having the structure of Formula I, and a pharmaceutically acceptable salt or pro-drug ester thereof:

Formula I

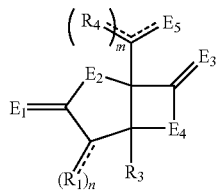

wherein $R_1$, $R_3$, and $R_4$ are separately selected from the group consisting of a hydrogen, a halogen, a mono-substituted, a poly-substituted or an unsubstituted moiety of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;
wherein m is equal to 1 or 2;
wherein n is equal to 1 or 2;
wherein each of $E_1$, $E_2$, $E_3$ and $E_4$ is a substituted or unsubstituted heteroatom; and
wherein $E_5$ is selected from the group consisting of OH, O, $OR_{10}$, S, $SR_{11}$, $SO_2R_{11}$, NH, $NH_2$, NOH, NHOH, $NR_{12}$, and $NHOR_{13}$.

37. A method of inducing apoptosis of a resistant Waldenstrom's Macroglobulinemia cell comprising contacting the cell with a compound having the structure of Formula I-15 and a pharmaceutically acceptable salt or pro-drug ester thereof:

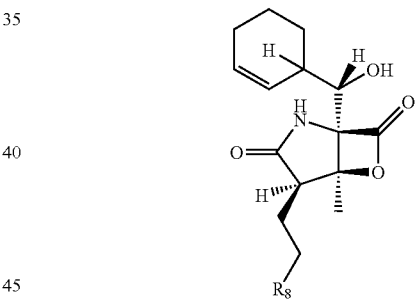

wherein $R_8$ is hydrogen, fluorine, chlorine, bromine or iodine.

38. The method of claim 37, wherein the compound is:

I-16

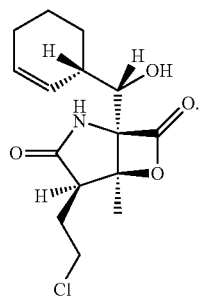

* * * * *